US009867841B2

(12) United States Patent
Magnani

(10) Patent No.: US 9,867,841 B2
(45) Date of Patent: Jan. 16, 2018

(54) COMPOUNDS, COMPOSITIONS AND METHODS USING E-SELECTIN ANTAGONISTS FOR MOBILIZATION OF HEMATOPOIETIC CELLS

(71) Applicant: GLYCOMIMETICS, INC., Gaithersburg, MD (US)

(72) Inventor: John L. Magnani, Gaithersburg, MD (US)

(73) Assignee: GLYCOMIMETICS, INC., Rockville, MD (US)

( * ) Notice: Subject to any disclaimer, the term of this patent is extended or adjusted under 35 U.S.C. 154(b) by 0 days.

(21) Appl. No.: 14/650,102

(22) PCT Filed: Dec. 5, 2013

(86) PCT No.: PCT/US2013/073258
§ 371 (c)(1),
(2) Date: Jun. 5, 2015

(87) PCT Pub. No.: WO2014/089269
PCT Pub. Date: Dec. 6, 2014

(65) Prior Publication Data
US 2016/0184339 A1    Jun. 30, 2016

Related U.S. Application Data

(60) Provisional application No. 61/734,924, filed on Dec. 7, 2012, provisional application No. 61/784,206, filed on Mar. 14, 2013.

(51) Int. Cl.
| | |
|---|---|
| *A61K 31/7034* | (2006.01) |
| *A61K 31/7052* | (2006.01) |
| *A61K 31/7056* | (2006.01) |
| *A61K 31/765* | (2006.01) |
| *A61K 31/7048* | (2006.01) |
| *A61K 45/06* | (2006.01) |

(52) U.S. Cl.
CPC ...... *A61K 31/7034* (2013.01); *A61K 31/7048* (2013.01); *A61K 31/7052* (2013.01); *A61K 31/7056* (2013.01); *A61K 31/765* (2013.01); *A61K 45/06* (2013.01)

(58) Field of Classification Search
None
See application file for complete search history.

(56) References Cited

U.S. PATENT DOCUMENTS

| | | |
|---|---|---|
| 4,471,057 A | 9/1984 | Koprowski et al. |
| 4,851,511 A | 7/1989 | Hakomori et al. |
| 4,859,769 A | 8/1989 | Karlsson et al. |
| 4,876,199 A | 10/1989 | Hakamori |
| 4,925,796 A | 5/1990 | Bergh et al. |
| 4,946,830 A | 8/1990 | Pulverer et al. |
| 5,143,712 A | 9/1992 | Brandley et al. |
| 5,151,360 A | 9/1992 | Handa et al. |
| 5,211,937 A | 5/1993 | Brandley et al. |
| 5,268,364 A | 12/1993 | Kojima et al. |
| 5,304,640 A | 4/1994 | Lasky et al. |
| 5,352,670 A | 10/1994 | Venot et al. |
| 5,369,096 A | 11/1994 | Yamada et al. |
| 5,412,123 A | 5/1995 | Rao et al. |
| 5,444,050 A | 8/1995 | Kogan et al. |
| 5,464,778 A | 11/1995 | Cummings et al. |
| 5,464,815 A | 11/1995 | Chamow et al. |
| 5,470,843 A | 11/1995 | Stahl et al. |
| 5,484,891 A | 1/1996 | Lasky et al. |
| 5,486,536 A | 1/1996 | Ward et al. |
| 5,519,008 A | 5/1996 | Rao et al. |
| 5,527,785 A | 6/1996 | Bevilacqua et al. |
| 5,538,724 A | 7/1996 | Butcher et al. |
| 5,559,103 A | 9/1996 | Gaeta et al. |
| 5,576,305 A | 11/1996 | Ratcliffe |
| 5,580,858 A | 12/1996 | Ippolito et al. |
| 5,580,862 A | 12/1996 | Rosen et al. |
| 5,589,465 A | 12/1996 | Ishida et al. |
| 5,604,207 A | 2/1997 | DeFrees et al. |
| 5,618,785 A | 4/1997 | Heavner et al. |
| 5,622,937 A | 4/1997 | Kogan et al. |

(Continued)

FOREIGN PATENT DOCUMENTS

| | | |
|---|---|---|
| DE | 2434953 | 2/1975 |
| EP | 319253 A2 | 6/1989 |

(Continued)

OTHER PUBLICATIONS

Abraham, W.M. et al.,"Selectin Blockade Prevents Antigen-induced Late Bronchial Response and Airway Hyperresponsiveness in Allergic Sheep," Am J. Respir Crit Care Med. 159: 1205-1214, 1999.
Acord, J. et al.,"A rapid microplate method for quantifying inhibition of bacterial adhesion to eukaryotic cells," Journal of Microbiological Methods 60: 55-62, 2005.
Adams, E. W. et al., "Oligosaccharide and Glycoprotein Microarrays as Tools in HIV Glycobiology: Glycan-Dependent gp120/Protein Interactions," Chemistry & Biology 11:875-881; Jun. 2004.
Aggoune et al., "The Vascular Niche Is Involved in Regulating Leukemic Stem Cells in Murine Chronic Myelogenous Leukemia" Blood, 124(21):516, Dec. 6, 2014.
Arakaki, R. et al., "T134, a Small-Molecule CXCR4 Inhibitor, Has no Cross-Drug Resistance with AMD3100, a CXCR4 Antagonist with a Different Structure," Journal of Virology 73(2):1719-1723, Feb. 1999.
Arshad, S. et al., "Primary prevention of asthma and allergy," J. Allergy Clin. Immunol., 116: 3-14 (2005).
Arshad, S. et al., "Primary prevention of asthma and atopy during childhood by allergen aviodance in infancy: a randomised controlled study," Thorax., 58:489-493 (2003).

(Continued)

*Primary Examiner* — Traviss C McIntosh, III
(74) *Attorney, Agent, or Firm* — Finnegan, Henderson, Farabow, Garrett & Dunner, LLP

(57) ABSTRACT

Methods are provided herein for use of E-selectin antagonists for mobilizing cells, such as hematopoietic cells, hematopoietic stem cells and progenitor cells, white blood cells, and malignant cells, and hematopoietic tumor cells from the bone marrow. More specifically, methods are provided for using E-selectin antagonists including, for example, glycomimetic compounds, antibodies, aptamers, and peptides for mobilizing cells from the bone marrow to the peripheral vasculature and tissues.

13 Claims, 15 Drawing Sheets

(56) References Cited

U.S. PATENT DOCUMENTS

| | | |
|---|---|---|
| 5,632,991 A | 5/1997 | Gimbrone, Jr. |
| 5,639,734 A | 6/1997 | Esko et al. |
| 5,646,123 A | 7/1997 | Ippolito et al. |
| 5,646,248 A | 7/1997 | Sawada et al. |
| 5,648,344 A | 7/1997 | Brandley et al. |
| 5,654,282 A | 8/1997 | Tang et al. |
| 5,654,412 A | 8/1997 | Srivastava et al. |
| 5,658,880 A | 8/1997 | Dasgupta et al. |
| 5,663,151 A | 9/1997 | Martel et al. |
| 5,679,321 A | 10/1997 | Dasgupta et al. |
| 5,679,644 A | 10/1997 | Rao et al. |
| 5,686,426 A | 11/1997 | Martel et al. |
| 5,693,621 A | 12/1997 | Toepfer et al. |
| 5,695,752 A | 12/1997 | Rosen et al. |
| 5,710,023 A | 1/1998 | Collins et al. |
| 5,710,123 A | 1/1998 | Heavner et al. |
| 5,723,583 A | 3/1998 | Seed et al. |
| 5,728,685 A | 3/1998 | Abbas et al. |
| 5,739,300 A | 4/1998 | Toepfer et al. |
| 5,747,463 A | 5/1998 | Marinier et al. |
| 5,750,508 A | 5/1998 | Dasgupta et al. |
| 5,753,617 A | 5/1998 | Heavner et al. |
| 5,753,631 A | 5/1998 | Paulson et al. |
| 5,763,413 A | 6/1998 | Numata et al. |
| 5,763,582 A | 6/1998 | Rao et al. |
| 5,789,385 A | 8/1998 | Anderson et al. |
| 5,789,573 A | 8/1998 | Baker et al. |
| 5,795,958 A | 8/1998 | Rao et al. |
| 5,811,404 A | 9/1998 | De Frees et al. |
| 5,811,405 A | 9/1998 | Toepfer et al. |
| 5,817,742 A | 10/1998 | Toepfer et al. |
| 5,817,807 A | 10/1998 | Bridger et al. |
| 5,827,817 A | 10/1998 | Larsen et al. |
| 5,827,837 A | 10/1998 | Bevilacqua et al. |
| 5,830,871 A | 11/1998 | Wong et al. |
| 5,837,689 A | 11/1998 | Anderson et al. |
| 5,837,690 A | 11/1998 | Rao et al. |
| 5,840,679 A | 11/1998 | Larsen et al. |
| 5,854,218 A | 12/1998 | DeFrees |
| 5,856,300 A | 1/1999 | Rittershaus et al. |
| 5,858,983 A | 1/1999 | Seed et al. |
| 5,858,994 A | 1/1999 | Kretzschmar et al. |
| 5,880,091 A | 3/1999 | Cummings et al. |
| 5,916,910 A | 6/1999 | Lai |
| 5,919,768 A | 7/1999 | Korgan et al. |
| 5,919,769 A | 7/1999 | Tsukida et al. |
| 5,962,422 A | 10/1999 | Nagy et al. |
| 5,976,540 A | 11/1999 | Rittershaus et al. |
| 5,977,080 A | 11/1999 | Rosen et al. |
| 5,985,852 A | 11/1999 | Nagy et al. |
| 5,994,402 A | 11/1999 | Rotstein et al. |
| 6,001,819 A | 12/1999 | Simon et al. |
| 6,001,988 A | 12/1999 | Parma et al. |
| 6,033,665 A | 3/2000 | Yednock |
| 6,037,333 A | 3/2000 | Panjwani |
| 6,043,348 A | 3/2000 | Lawman et al. |
| 6,110,897 A | 8/2000 | Unverzagt et al. |
| 6,111,065 A | 8/2000 | Heavner et al. |
| 6,120,751 A | 9/2000 | Unger |
| 6,121,233 A | 9/2000 | Magnani et al. |
| 6,124,267 A | 9/2000 | McEver et al. |
| 6,133,239 A | 10/2000 | Handa et al. |
| 6,133,240 A | 10/2000 | Taylor et al. |
| 6,136,790 A | 10/2000 | Toepfer et al. |
| 6,169,077 B1 | 1/2001 | Oehrlein |
| 6,177,547 B1 | 1/2001 | Cummings et al. |
| 6,187,754 B1 | 2/2001 | Oehrlein |
| 6,193,973 B1 | 2/2001 | Tuttle |
| 6,193,979 B1 | 2/2001 | Rittershaus et al. |
| 6,197,752 B1 | 3/2001 | Schmidt et al. |
| 6,225,071 B1 | 5/2001 | Cummings et al. |
| 6,235,309 B1 | 5/2001 | Nagy et al. |
| 6,280,932 B1 | 8/2001 | Parma et al. |
| 6,287,556 B1 | 9/2001 | Portnoy et al. |
| 6,309,639 B1 | 10/2001 | Cummings et al. |
| 6,372,712 B1 | 4/2002 | Briesewitz |
| 6,387,884 B1 | 5/2002 | Magnani et al. |
| 6,391,857 B1 | 5/2002 | Magnani et al. |
| 6,407,135 B1 | 6/2002 | Lai et al. |
| 6,465,434 B1 | 10/2002 | Magnani et al. |
| 6,492,332 B1 | 12/2002 | Demopulos et al. |
| 6,503,885 B1 | 1/2003 | Kiso et al. |
| 6,506,770 B1 | 1/2003 | Bridger et al. |
| 6,515,117 B2 | 2/2003 | Ellsworth et al. |
| 6,528,487 B1 | 3/2003 | Heavner et al. |
| 6,569,998 B2 | 5/2003 | Cummings et al. |
| 6,592,872 B1 | 7/2003 | Klimpel et al. |
| 6,683,056 B2 | 1/2004 | Washburn et al. |
| 6,756,391 B2 | 6/2004 | Bridger et al. |
| 6,844,175 B2 | 1/2005 | Bistrup et al. |
| 6,872,714 B1 | 3/2005 | Schols |
| 6,875,738 B1 | 4/2005 | Clark-Lewis et al. |
| 6,887,842 B1 | 5/2005 | Briesewitz |
| 6,921,531 B2 | 7/2005 | Briesewitz |
| 6,943,239 B2 | 9/2005 | Holgersson et al. |
| 6,967,093 B2 | 11/2005 | Bistrup et al. |
| 7,060,685 B2 | 6/2006 | Magnani et al. |
| 7,087,212 B2 | 8/2006 | Cantrell et al. |
| 7,160,872 B2 | 1/2007 | Bridger et al. |
| 7,226,949 B2 | 6/2007 | Crooks et al. |
| 7,300,656 B2 | 11/2007 | Ashkenazi et al. |
| 7,361,644 B2 | 4/2008 | Magnani et al. |
| 7,390,784 B2 | 6/2008 | Briesowitz |
| 7,414,065 B2 | 8/2008 | Bridger et al. |
| 7,422,733 B2 | 9/2008 | Ranganathan et al. |
| 7,449,176 B2 | 11/2008 | Ashkenazi et al. |
| 7,517,980 B2 | 4/2009 | Magnani et al. |
| 7,563,760 B2 | 7/2009 | Larsen et al. |
| 7,709,486 B2 | 5/2010 | Bridger et al. |
| 7,728,117 B2 | 6/2010 | Magnani et al. |
| 7,741,312 B2 | 6/2010 | Magnani et al. |
| 7,951,816 B2 | 5/2011 | Kokubo et al. |
| 7,964,569 B2 | 6/2011 | Ernst et al. |
| 7,989,601 B2 | 8/2011 | Magnani et al. |
| 8,026,222 B2 | 9/2011 | Magnani et al. |
| 8,039,442 B2 | 10/2011 | Magnani |
| 8,258,290 B2 | 9/2012 | Magnani et al. |
| 8,361,975 B2 | 1/2013 | Magnani |
| 8,410,066 B2 | 4/2013 | Magnani |
| 8,518,896 B2 | 8/2013 | Magnani et al. |
| 8,530,448 B2 | 9/2013 | Magnani et al. |
| 8,633,303 B2 | 1/2014 | Magnani et al. |
| RE44,778 E | 2/2014 | Magnani et al. |
| 8,895,510 B2 | 11/2014 | Magnani |
| 8,921,328 B2 | 12/2014 | Ernst et al. |
| 9,109,002 B2 * | 8/2015 | Magnani ............ C07H 15/207 |
| 9,254,322 B2 | 2/2016 | Levesque et al. |
| 9,486,497 B2 | 11/2016 | Levesque et al. |
| 9,534,009 B2 | 1/2017 | Magnani |
| 2001/0046970 A1 | 11/2001 | Nagy et al. |
| 2001/0051370 A1 | 12/2001 | Bistrup et al. |
| 2002/0031508 A1 | 3/2002 | Wagner et al. |
| 2002/0040008 A1 | 4/2002 | Wagner et al. |
| 2002/0128225 A1 | 9/2002 | Liu et al. |
| 2002/0132220 A1 | 9/2002 | Berens et al. |
| 2002/0155429 A1 | 10/2002 | Allaway et al. |
| 2002/0164336 A1 | 11/2002 | Harrison et al. |
| 2002/0164748 A1 | 11/2002 | Bistrup et al. |
| 2002/0168366 A1 | 11/2002 | Stewart et al. |
| 2003/0012787 A1 | 1/2003 | Ashkenazi et al. |
| 2003/0012790 A1 | 1/2003 | Ashkenazi et al. |
| 2003/0018181 A1 | 1/2003 | Larsen et al. |
| 2003/0036560 A1 | 2/2003 | Sonis et al. |
| 2003/0039683 A1 | 2/2003 | Cantrell et al. |
| 2003/0211078 A1 | 11/2003 | Heavner |
| 2004/0067220 A1 | 4/2004 | Sykes |
| 2004/0072796 A1 | 4/2004 | Embury et al. |
| 2004/0096396 A1 | 5/2004 | Magnani et al. |
| 2004/0097403 A1 | 5/2004 | Ranganathan et al. |
| 2004/0219158 A1 | 11/2004 | Magnani |
| 2005/0112124 A1 | 5/2005 | Frenette et al. |
| 2005/0181987 A1 | 8/2005 | Blaszczyk-Thurin et al. |
| 2005/0187171 A1 | 8/2005 | Magnani et al. |
| 2005/0214283 A1 | 9/2005 | Sackstein et al. |

(56) References Cited

U.S. PATENT DOCUMENTS

| | | |
|---|---|---|
| 2006/0217303 A1 | 9/2006 | Kriegler |
| 2006/0264451 A1 | 11/2006 | Shim et al. |
| 2006/0287253 A1 | 12/2006 | Kriegler et al. |
| 2007/0021378 A1 | 1/2007 | Varki et al. |
| 2007/0054870 A1 | 3/2007 | Magnani et al. |
| 2007/0054930 A1 | 3/2007 | Shim et al. |
| 2007/0213278 A1 | 9/2007 | Wong et al. |
| 2008/0025992 A1 | 1/2008 | Fabene et al. |
| 2008/0112955 A1 | 5/2008 | Embury et al. |
| 2008/0161546 A1 | 7/2008 | Ernst et al. |
| 2008/0200406 A1 | 8/2008 | Magnani |
| 2008/0227799 A1 | 9/2008 | Liotta et al. |
| 2008/0300220 A1 | 12/2008 | Ranganathan et al. |
| 2008/0306098 A1 | 12/2008 | Mutz et al. |
| 2009/0036386 A1 | 2/2009 | Magnani et al. |
| 2009/0053198 A1 | 2/2009 | Sackstein |
| 2009/0054334 A1 | 2/2009 | Mutz et al. |
| 2009/0175792 A1 | 7/2009 | Magnani et al. |
| 2009/0176717 A1 | 7/2009 | Magnani |
| 2009/0253646 A1 | 10/2009 | Magnani |
| 2009/0312278 A1 | 12/2009 | Magnani et al. |
| 2010/0145032 A1 | 6/2010 | Laine et al. |
| 2010/0215575 A1 | 8/2010 | O'Neill et al. |
| 2010/0240773 A1 | 9/2010 | Korzekwa et al. |
| 2010/0292095 A1 | 11/2010 | Laukkanen et al. |
| 2010/0303766 A1 | 12/2010 | Miyaji et al. |
| 2010/0311105 A1 | 12/2010 | Lu et al. |
| 2011/0002881 A1 | 1/2011 | Levesque et al. |
| 2011/0020270 A1 | 1/2011 | Levesque et al. |
| 2011/0142856 A1 | 6/2011 | Kokubo et al. |
| 2011/0229409 A1 | 9/2011 | Ranganathan et al. |
| 2011/0251148 A1 | 10/2011 | Magnani et al. |
| 2011/0257380 A1 | 10/2011 | Ernst et al. |
| 2012/0093782 A1 | 4/2012 | Grove et al. |
| 2012/0129712 A1 | 5/2012 | Satomaa et al. |
| 2012/0202762 A1 | 8/2012 | Magnani |
| 2012/0258043 A1 | 10/2012 | Ranganathan et al. |
| 2012/0329755 A1 | 12/2012 | Magnani et al. |
| 2013/0184229 A1 | 7/2013 | Magnani et al. |
| 2013/0261070 A1 | 10/2013 | Magnani et al. |
| 2013/0281646 A1 | 10/2013 | Korzekwa et al. |
| 2014/0073594 A1 | 3/2014 | Magnani et al. |
| 2014/0178303 A1 | 6/2014 | Magnani et al. |
| 2015/0051164 A1 | 2/2015 | Magnani |
| 2016/0193294 A1 | 7/2016 | Magnani et al. |
| 2016/0243145 A1 | 8/2016 | Magnani et al. |

FOREIGN PATENT DOCUMENTS

| | | |
|---|---|---|
| EP | 381310 A1 | 8/1990 |
| EP | 408859 B1 | 1/1991 |
| EP | 671407 A2 | 9/1995 |
| EP | 0 867 722 | 9/1998 |
| JP | 06-0306092 | 11/1994 |
| JP | 9-176047 | 7/1997 |
| JP | 2002-520323 | 7/2002 |
| JP | 2004-518704 | 6/2004 |
| JP | 2009-507031 | 2/2009 |
| WO | WO 90/13300 | 11/1990 |
| WO | WO 91/19502 | 12/1991 |
| WO | WO 92/01718 | 2/1992 |
| WO | WO 92/07572 | 5/1992 |
| WO | WO 94/26760 | 11/1994 |
| WO | WO 94/29477 | 12/1994 |
| WO | WO 95/00527 | 1/1995 |
| WO | WO 95/03059 | 2/1995 |
| WO | WO 95/29681 | 11/1995 |
| WO | WO 96/20204 | 7/1996 |
| WO | WO 96/25418 | 8/1996 |
| WO | WO 96/26950 | 9/1996 |
| WO | WO 97/01335 | 1/1997 |
| WO | WO 97/01569 | 1/1997 |
| WO | WO 97/14707 | 4/1997 |
| WO | WO 97/28173 | 8/1997 |
| WO | WO 97/28174 | 8/1997 |
| WO | WO 98/06730 | 2/1998 |
| WO | WO 98/13058 | 4/1998 |
| WO | WO 98/04677 | 10/1998 |
| WO | WO 99/42130 | 8/1999 |
| WO | WO 99/43353 | 9/1999 |
| WO | WO 99/43356 | 9/1999 |
| WO | WO 00/02870 | 1/2000 |
| WO | WO 01/89564 | 11/2001 |
| WO | WO 02/22820 | 3/2002 |
| WO | WO 02/062810 | 8/2002 |
| WO | WO 03/055876 | 7/2003 |
| WO | WO 03/086960 | 10/2003 |
| WO | WO 03/097656 | 11/2003 |
| WO | WO 2004/004636 | 1/2004 |
| WO | WO 2004/033663 | 4/2004 |
| WO | WO 2004/058304 | 7/2004 |
| WO | WO 2004/094619 | 11/2004 |
| WO | WO 2005/016349 | 2/2005 |
| WO | WO 2005/046597 | 5/2005 |
| WO | WO 2005/051920 | 6/2005 |
| WO | WO 2005/054264 | 6/2005 |
| WO | WO 2005/058934 | 6/2005 |
| WO | WO 2005/085219 | 9/2005 |
| WO | WO 2005/116088 | 12/2005 |
| WO | WO 2006/017180 | 2/2006 |
| WO | WO 2006/022454 | 3/2006 |
| WO | WO 2006/062946 | 6/2006 |
| WO | WO 2006/074426 | 7/2006 |
| WO | WO 2006/074428 | 7/2006 |
| WO | WO 2006/089106 | 8/2006 |
| WO | WO 2006/127906 | 11/2006 |
| WO | WO 2007/021721 | 2/2007 |
| WO | WO 2007/022089 | 2/2007 |
| WO | WO 2007/022385 | 2/2007 |
| WO | WO 2007/028050 | 3/2007 |
| WO | WO 2007/033329 | 3/2007 |
| WO | WO 08/011094 | 1/2008 |
| WO | WO 2008/008852 | 1/2008 |
| WO | WO 2008/008854 | 1/2008 |
| WO | WO 2008/060378 | 5/2008 |
| WO | WO 2008/100453 | 6/2008 |
| WO | WO 2008/109154 | 9/2008 |
| WO | WO 2009/011889 | 1/2009 |
| WO | WO 2009/073911 | 6/2009 |
| WO | WO 2009/073916 | 6/2009 |
| WO | WO 2009/126556 | 10/2009 |
| WO | WO 2009/152245 | 12/2009 |
| WO | WO 2010/126888 | 11/2010 |
| WO | WO 2012/037034 | 3/2012 |
| WO | WO 2012/061662 | 5/2012 |
| WO | WO 2013/096926 | 6/2013 |
| WO | WO 14/070991 | 5/2014 |
| WO | WO 14/149837 | 9/2014 |

OTHER PUBLICATIONS

Astronomo, R.D. et al., "A Glycoconjugate Antigen Based on the Recognition Motif of a Broadly Neutralizing Human Immunodeficiency Virus Antibody, 2G12, Is Immunogenic but Elicits Antibodies Unable to Bind to the Self Glycans of gp120," Journal of Virology 82(13):6359-6366, Jul. 2008.

Azab et al, "Role of Selectins in the Pathogenesis of Multiple Myeloma", ASCO Annual Meeting 2009, Poster #11103, May 2009.

Azab et al., "P-selectin Glycoprotein Ligand Regulates the Interaction of Multiple Myeloma Cells with the Bone Marrow Microenvironment", Blood, 119:1468-1476, Nov. 16, 2011.

Azab et al., "Role of Selectins in the Pathogenesis of Multiple Myeloma", J Clin Oncol, 27(15s):absrt 11103, 2009.

Baeckstrom et al.., "Purification and Characterization of a Membrane-bound and a Secreted Mucin-type Glycoprotein Carrying the Carcinoma-associated Sialyl-Le.sup.a Epitope on Distinct Core Proteins," J. Biol. Chem. 266(32):21537-21547, 1991.

Banteli et al., "Synthesis of sialyl lewisx mimics. Modifications of the 6-position of galactose," Bioorganic & Medicinal Chemistry Letters, 11(4): 459-462 (2001).

Banteli, R. et al.,"Potent E-Selectin Antagonists," Helvetica Chimica Acta 83(11): 2893-2907, 2000.

(56) References Cited

OTHER PUBLICATIONS

Barasch et al., "Palifermin for Management of Treatment-Induced Oral Mucositis in Cancer Patients", Biologics: Targets & Therapy, 3:111-116, 2009.
Barnes, P. et al., "How do corticosteroids work in asthma?" Ann. Intern. Med., 139: 359-370 (2003).
Bastin, R.. et al,"Salt Selection and Optimisation Procedures for Pharmaceutical New Chemical Entities" Organic Process Research & Development (2000), vol. 4. pp. 427-435.
Belcher, J.D. et al., "Activated monocytes in sickle cell disease: potential role in the activation of vascular endothelium and vaso-occlusion," Blood 96(7):2451-2459, Oct. 1, 2000.
Belcher, J.D. et al., "Inflammatory response in transgenic mouse models of human sickle cell anemia," Blood 96(11)Pt. 1 :600a, Abstract #2574, Nov. 16, 2000.
Berg et al., "A Carbohydrate Domain Common to Both Sialyl Le.sup.a and Sialyl Le.sup.x Is Recognized by the Endothelial Cell Leukocyte Adhesion Molecule ELAM-1," J. Biol. Chem. 266(23):14869-14872, 1991.
Berg et al., "The Cutaneous Lymphocyte Antigen Is a Skin Lymphocyte Homing Receptor for the Vascular Lectin Endothelial Cell-Leukocyte Adhesion Molecule 1," J. Exp. Med. 174:1461-1466, 1991.
Bhaskar, V. et al. "E-selectin Up-regulation Allows for Targeted Drug Delivery in Prostate Cancer," Cancer Research, 63: 6387-6394 (Oct. 2003).
Bird and Kimber,"Oligosaccharides Containing Fucose Linked .alpha.(1-3) and .alpha.(1-4) to N-Acetylglucosamine Cause Decompaction of Mouse Morulae," Devel. Biol. 104:449-460, 1984.
Bjercke,"Rational Design and Synthesis of Oligosaccharide Mimetics: Selectin Antagonists as Cell Adhesion Inhibitors," Abstracts of Papers, 210th ACS National Meeting, American Chemical Society, Chicago, IL, Aug. 20-24, 1995, MEDI-18.
Blanc-Muesser et al., "Syntheses Stereoselective de 1-Thioglycosides," Carbohydrate Research 67:305-328, 1978.
Bochner, B. et al., "Glycan array screening reveals a candidate ligand for Siglec-8," Journal of Biological Chemistry, 280(6): 4307-4312 (2005).
Bock, K. et al., "Conformations in Solution of a, a-Trehalose, a-D-Glucopyranosyl a-D-Mannopyranoside, and Their 1-Thioglycosyl Analogs, and a Tentative Correlation of Their Behaviour with Respect to the Enzyme Trehalase," European Journal of Biochemistry, 131:696-600, 1983.
Bowen et al., "Characterization of a Human Homologue of the Murine Peripheral Lymph Node Homing Receptor," Journal of Cell Biology, 109:421-427, 1989.
Brandley et al., "Carbohydrate Ligands of LEC Cell Adhesion Molecules," Cell, 63:861-863, 1990.
Bridger, GJ et al. "Synthesis and Structure—Activity Relationships of Phenylenebis(methylene)—Linked Bis-Tetraazamacrocycles That Inhibit HIV Replication. Effects of Macrocyclic Ring Size and Substituents on the Aromatic Linker," J. Med. Chem., 38: 366-378 (1995).
Broquet et al., "Effect of Desipramine on a Glycoprotein Sialyltransferase Activity in C6 Cultured Glioma Cells," J. Neurochem., 54:388-394, 1990.
Calarese, D. A. et al., "Antibody Domain Exchange is and Immunological Solution to Carbohydrate Cluster Recognition," Science 300:2065-2071, Jun. 2003.
Calarese, D. A. et al., "Dissection of the Carbohydrate Specificity of the Broadly Neutralizing Anti-HIV-1 Antibody 2G12," Proceedings of the National Academy of Sciences 102(38):13372-13377, Sep. 2005.
Cao, X. et al., "Defective Lymphoid Development in Mice Lacking Expression of the Common Cytokine Receptor Y Chain," Immunity, 2:223-238, Mar. 1995.
Ceder, O. et al., "On the Absolute Configuration of3-Cyclohexene-I-carboxylic Acid," Acta Chemica Scandivavica, 24(8):2693-2698, 1970.

Chang et al., "Effects of Pan-Selectin Antagonist GMI-1070 on the Treatment of Vaso-Occlusion in Sickle Cell Mice", Blood. 112(11), Abstract #535, Nov. 2008.
Chang, J. et al. "GMI-1070, a novel pan-selectin antagonist, reverses acute vascular occlusions in sickle cell mice," Blood, 116(10): 1779-1786 (Sep. 2010).
Chase et al., "E-Selectin Ligands as Mechanosensitive Receptors on Neutrophils in Health and Disease", Annals of Biomedical Engineering, DOI:10.1007/s10439-011-0507-y, Jan. 24, 2012.
Chemical Abstracts (STN), Accession No. 1997:584307, Jul. 8, 1997.
Chien et al., "A Novel Small Molecule E-Selectin Inhibitor GMI-1271 Blocks Adhesion of AML Blasts to E-Selectin and Mobilizes Blood Cells in Nodscid IL2Rgc-/- Mice Engrafted with Human AML", Blood, 120(21), Abstract #4092, Nov. 16, 2012.
Chien et al., "A Novel Small Molecule E-Selectin Inhibitor GMI-1271 Blocks Adhesion of AML Blasts to E-Selectin and Mobilizes Blood Cells in Nodscid IL2Rgc-/- Mice Engrafted with Human AML", 2012 ASH Annual Meeting, Poster #54715, Dec. 8, 2012.
Chien et al., "Adhesion of Acute Myeloid Leukemia Blasts to E-Selectin in the Vascular Niche Enhances Their Survival by Mechanisms Such as Wnt Activation", Blood, 122(21):61, Nov. 15, 2013.
Chien et al., "Novel Dual E-Selectin-CXCR4 Inhibitors Mobilize Human Acute Myeloid Leukemia (AML) Cells in the NODscid IL2R{gamma}c-/- Xenograft and Confer Susceptibility to Cytarabine", Blood, 118(21), Abstract #579, Nov. 18, 2011.
Childs et al. ,"High-molecular-weight glycoproteins are the major carriers of the carbohydrate differentiation antigens I, I and SSEA-1 of mouse teratocarcinoma cells," Biochem. J., 215:491-503 (1983).
Christianson, S.W. et al., "Enhanced Human CD4+ T Cell Engraftment in β2-Microglobulin-Deficient NOD-scid Mice," The Journal of Immunology, 158:3578-3586 (1997).
Cleophax, J. et al., "A chiral synthesis of D-(+)-2,6-dideoxystreptamine and its microbial incorporation into novel antibodies," Journal of the American Chemical Society, 98 (22): 7110-7112 (Oct. 27, 1976).
Collier, et al., "Membrane translocation by anthrax toxin," Molecular Aspects of Medicine, 30(6): 413-422 (Dec. 1, 2009).
Corral et al., "Requirements for Sialic Acid on Neutrophils in a GMP-140 (PADGEM) Mediated Adhesive Interaction with Activated Platelets," Biochem. Biophys. Res. Commun., 172:1349-1356, (1990).
Corson, Timothy W. et al., "Design and Applications of Bifunctional Small Molecules: Why Two Heads Are Better Than One," ACS Chemical Biology 3(11):677-692, Nov. 2008.
Crawford et al., "AMD070, a CXCR4 Chemokine Receptor Antagonist: Practical Large-Scale Laboratory Synthesis," Org. Process Res. Devel. 12:823-830, 2008.
Cumpstey, I. et al. "C2-Symmetrical Thiodigalactoside Bis-Benzamido Derivatives as High-Affinity Inhibitors of Galectin-3: Efficient Lectin Inhibition through Double Arginine—Arene Interactions," Angew Chem., 117;5240-5242 (2005).
Daoudil, Jean-Michel et al., "New bicyclam-GalCer analogue conjugates: synthesis and in vitro anti-HIV activity," Bioorg. & Med. Chem. Letters 14:495-498, 2004.
Datta and Takayama,"Isolation and purification of trehalose 6-mono- and 6,6'-di-corynomycolates from Cornyebacterium matruchotii. Structural characterization of .sup.1H NMR," Carbohydrate Research 245: 151-158, 1993.
De Clercq, Erik, "The bicyclam AMD3100 story," Nat. Rev. Drug Disc. 2:581-587, Jul. 2003.
Decastro et al., "Effects of GMI-1070, a Pan-Selectin Inhibitor, on Pain Intensity and Opioid Utilization in Sickle Cell Disease", Blood, 122(21):775, Nov. 15, 2013.
Devine: "Rapid Mobilization of CD34+ Cells Following Administration of the CXCR4 Antagonist AMD 3100 to Patients With Multiple Myeloma and Non-Hodgkin's Lymphoma," Journal of Clinical Oncology, 22(6): 1095-1102 (Feb. 23, 2004).
Diamandis et al., "Reflection on the Discovery of Carcinoembryonic Antigen, Prostate-Specific Antigen, and Cancer Antigens CA125 and CA19-9", Clin Chem, 59(1), Nov. 30, 2012.

(56) References Cited

OTHER PUBLICATIONS

Dittmar, Thomas et al., "Adhesion Molecules and Chemokines: the Navigation System for Circulating Tumor (Stem) Cells to Metastasize in an Organ-Specific Manner," Clin. Exp. Metastasis 25:11-32, 2008.
Doranz, B.J. et al., "Safe Use of the CSCR4 Inhibitor ALX40-4C in Humans," AIDS Research and Human Retroviruses 17(6):475-466, 2001.
Duijvestijn et al.,"High Endothelial Differentiation in Human Lymphoid and Inflammatory Tissues Defined by Monoclonal Antibody HECA-452," Am. J. Path. 130:147-155, 1988.
Dupre, B. et al.,"Glycomimetic Selectin Inhibitors: (.alpha.-D-Mannopyranosyloxy)methylbiphenyls," Bioorganic & Medicinal Chemistry Letters 6(5): 569-572, 1996.
Edgington, "How Sweet It Is: Selectin-Mediating Drugs," Biotechnology 10: 383-389, 1992.
Edwards, W. Barry et al., "Generally Applicable, Convenient Solid-Phase Synthesis and Receptor Affinities of Octreotide Analogs," J. Med. Chem. 37:3729-3757, 1994.
Egberink, H. et al. "Bicyclams, Selective Antagonists of the Human Chemokine Receptor CXCR4, Potently Inhibit Feline Immunodeficiency Virus Repllcation," Journal of Virology, 73(8): 6346-6352 (1999).
Eggens et al.,"A Role of Carbohydrate-Carbohydrate Interaction in the Process of Specific Cell Recognition During Embryogenesis and Organogenesis: A Preliminary Note," Biochem. Biophys. Res. Commun. 158(3):913-920, 1989.
Eggens et al.,"Specific Interaction between Le.sup.X and Le.sup.X Determinants. A Possible Basis for Cell Recognition in Preimplantation Embryos and in Embryonal Carcinoma Cells," J. Biol. Chem. 264(16):9476-9484, 1989.
Egger, J. et al. "Nanomolar E-Selectin Antagonists with Prolonged Half-Lives by a Fragment-Based Approach," JACS, 135(26): 9820-9828 (Jul. 2013).
Embury, S.H. et al., "The contribution of endothelial cell P-selectin to the microvascular flow of mouse sickle erythrocytes in vivo," Blood 104(10):3378-3385, Nov. 15, 2004.
English Abstract for DE 2434953, Feb. 6, 1975.
English Abstract for JP 9-176047, published Jul. 8, 1997.
English Abstract for WO 96/20204, published Jul. 4, 1996.
English Translation of JP 06-0306092, dated Nov. 1, 1994.
Ernst and Oehrlein, "Substrate and donor specificity of glycosyl transferases," Glycoconjugate Journal 16: 161-170, 1999.
Ernst B. et al.,"Design and Synthesis of E-Selectin Antagonists," Chimia 55:268-274, 2001.
Ernst, B. et al., "From carbohydrate leads to glycomimetic drugs," Nature Reviews 8:661-677, Aug. 2009.
Esposito et al., "Exploration of a Potent E-selectin Antagonist (GMI-1271) as a Potential Therapeutic for Treating Breast Cancer Metastasis to the Lung and Bone", AACR Annual Meeting 2014, Poster #4039, Apr. 8, 2014.
Esposito et al., "Exploration of a Potent E-selectin Antagonist (GMI-1271) as a Potential Therapeutic for Treating Breast Cancer Metastasis to the Lung and Bone", Cancer Res, Abstract #4039. Oct. 1, 2014.
European Search Report for EP 11010157 dated Mar. 27, 2012.
European Search Report for EP 2249854 dated Feb. 18, 2009.
Faber et al., "The Many Facets of SDF-1a, CXCR4 Agonists and Antagonists on Hematopoietic Progenitor Cells," J. Biomed. & Biotech. Article ID 26065:1-10, 2007.
Feletou, M. et al., "Endothelial dysfunction: a multifaceted disorder," Am. J. Physiol. Heart Circ. Physiol., 291: H985-H1002 (2006).
Fenderson et al.,"A Multivalent Lacto-N-Fucopenataose III-Lysyllysine Conjugate Decompacts Preimplantation Mouse Embryos, While the Free Oligosaccharide is Ineffective," J. Exp. Med. 160:1591-1596, 1984.
Fenderson et al.,"Coordinate Expression of X and Y Haptens during Murine Embryogenesis," Devel. Biol. 114:12-21, 1986.
Fenderson et al.,"The blood group I antigen defined by monoclonal antibody C6 is a marker of early mesoderm during murine embryogenesis," Differentiation 38:124-133, 1988.
Filser, C. et al., "Synthetic glycopeptides from the E-selectin ligand 1 with varied sialyl Lewis(x) structure as cell-adhesion inhibitors of E-selectin," Angewandte Chemie—International Edition, 46(12): 2108-2111 (2007).
Flanner et al., "Comparison of Predicted GMI-1070 Human Intravenous Pharmacokinetics from in silico PBPK and Allometric Scaling Models", AAPS Annual Meeting, Abstract, Nov. 2009.
Flanner et al., "Comparison of Predicted GMI-1070 Human Intravenous Pharmacokinetics from in silica PBPK and Allometric Scaling Models", AAPS Annual Meeting. Poster, Nov. 2009.
Frison, N. et al., "Oligolysine-Based Oligosaccharide Clusters: Selective Recognition and Endocytosis by the Mannose Receptor and Dendritic Cell-Specific Intercellular Adhesion Molecule 3 (ICAM-3)—Grabbing Nonintegrin," the Journal of Biological Chemistry 278(26):23922-23929, Apr. 2003.
Fukushi et al.,"Novel Fucolipids Accumulating in Human Adenocarcinoma," J. Biol. Chem. 259(16):10511-10517 (1984).
Fukushi et al.,"Novel Fucolipids Accumulating in Human Adenocarcinoma. II. Selective Isolation of Hybridoma Antibodies That Differentially Recognize Mono-, Di-, and Trifucosylated Type 2 Chain," J. Biol. Chem. 259(7):4681-4685, 1984.
Gabius et al.,"Endogenous Tumor Lectins: Overview and Perspectives," Anticancer Res. 6:573-578, 1986.
Gais, H.-J. et al.,"Enantioselective and Enantioconvergent Syntheses of Building Blocks for the Total Synthesis of Cyclopentanoid Natural Products," Angewandte Chemie, Int. Ed. Eng. 23(2):142-143, 1984.
Gallatin et al.,"A cell-surface molecule involved in organ-specific homing of lymphocyctes," Nature 304:30-34, 1983.
Garber, N. et al., "On the specificity of the D-galactose-binding lectin (PA-I) of Pseudomonas aeruginosa and its strong binding to hydrophobic derivatives of D-galactose and thiogalactose," Biochimica et Biophysica Acta, 1116:331-333 (1992).
Gelbrich, T et al., "Preparation of 4-benzylsulfanyl[1,2,3,5]dithiadiazol-1-ylium chlorides: potential precursors to meso-ionic 1,2,3,5-dithiadiazolium-4-thiolate," Arkivoc, (vl): 224-223 (2002).
Ghobrial, IM, "Myeloma as a model for the process of metastasis: implications for therapy," 120(1): 20-30 (2012).
Gilboa-Gardner, N. et al., "A new mitogenic D-galactosephilic lectin isolated from seeds of the coral-tree *Erythrina coraliodendron*. Comparison with *Glycine max* (soybean) and Pseudomonas aeruginosa lectins," Canadian Journal of Biochemistry, 59(5):315-320 (1981).
Goodman and Gillman's, "Pharmacological Basis of Therapeutics," l0th edition, p. 54 (2001).
Gooi et al.,"Stage-specific embryonic antigen involves alpha 1-3 fucosylated type 2 blood group chains," Nature 292:156-158, 1981.
Hakomori et al.,"Novel Fucolipids Accumulating in Human Adenocarcinoma. I. Glycolipids With Di- or Trifucosylated Type 2 Chain," J. Biol. Chem. 259(7):4672-4680, 1984.
Hakomori et al.,"The Hapten Structure of a Developmentally Regulated Glycolipid Antigen (SSEA-1) Isolated From Human Erythrocytes and Adenocarcinoma: A Preliminary Note," Biochem. Biophys. Res. Comm. 100(4):1578-1586, 1981.
Hakomori S.,"Aberrant Glycosylation in Cancer Cell Membranes as Focused on Glycolipids: Overview and Perspectives," Cancer Res. 45:2405-2414, 1985.
Halloran, M. et al., "Ley/H: An endothelial-selective cytokine-inducible angiogenic mediator," Journal of Immunology, 164(9):4868-4877 (May 1, 2000).
Handa et al.,"Selectin GMP-140 (CD62; PADGEM) Binds to Sialosyl-Le.sup.a and Sialosyl-Le.sup.x, and Sulfated Glycans Modulate this Binding," Biochemical and Biophysical Research Communication 181(3):1223-1230, 1991.
Hanson and Zopf,"Biosynthesis of the Cancer-associated Sialyl-Le.sup.a Antigen," Journal of Biological Chemistry 260(16):9388-9892, 1985.
Harlan, J.M.,"Introduction-anti-adhesion therapy in sickle cell disease," Blood 95:365-367, 2000.

(56) References Cited

OTHER PUBLICATIONS

Hasegawa et al.,"Synthesis of deoxy-L-fucose-containing sialyl Lewis X ganglioside analogues," Carbohydrate Research 257: 67-80, 1994.

Hasegawa et al.,"Synthesis of sialyl Lewis X ganglioside analogues containing modified L-fucose residues," Carbohydrate Research 274: 165-181, 1995.

Hebbel, P.R.,"Blockade of Adhesion of Sickle Cells to Endothelium by Monoclonal Antibodies," the New England Journal of Medicine 342:1910-1912, Jun. 22, 2000.

Hendrix, C.W. et al., "Pharmacokinetics and Safety of AMD-3100, a Novel Antagonist of the CXCR-4 Chemokine Receptor, in Human Volunteers," Antimicrobial Agents and Chemotherapy 44(6):1667-1673, Jun. 2000.

Hilal et al.,"Electronic structure of orotic acid I. Geometry, conformational preference and tautomerism, Journal of Molecular Structure (Theochem)" 685 (2004) 35-42.

Hilgenbrink, A. et al., "Folate receptor-mediated drug targeting: from therapeutics to diagnostics," J. Pharm. Sci., 94(10): 2135-2146 (2005).

Holgate, ST et al., "Epithelium dysfunction in asthma," Current Reviews of Allergy and Clinical Immunology, 120: 1233-1234 (2007).

Holmes et al., "Enzymatic Basis for the Accumulation of Glycolipids with X and Dimeric X Determinants in Human Lung Cancer Cells (NCI-H69)," J. Biol. Chem. 260(12):7619-7627, 1985.

Hong, P. W.-P. et al., "Identification of the Optimal DC-SIGN Binding Site on Human Immunodeficiency Virus Type 1 gp120," Journal of Virology 18(15):8325-8336, Aug. 2007.

Huse et al.,"Generation of a Large Combinatorial Library of the Immunoglobulin Repertoire in Phage Lambda," Science 246:1275-1281, 1989.

Huwe, C. M. et al.,"Design, Synthesis and Biological Evaluation of Aryl-substituted Sialyl Lewis X Mimetics Prepared via Cross-metathesis of C-Fucopeptides," Biological & Medicinal Chemistry 7:773-786, 1999.

Hynes, R.,"Integrins: A Family of Cell Surface Receptors," Cell 48:549-554, 1987.

Ikeuchi, Yoshihiro et al., "Synthesis and Antitumor Activities of Novel 5-Deazaflavin-Sialic Acid Conjugate Molecules," Bioorg. & Med. Chem. 8:2027-2035, 2000.

International Search Report for PCT/US2003/19429 dated Dec. 18, 2003.

International Search Report for PCT/US2003/40681 dated Apr. 26, 2004.

International Search Report for PCT/US2004/038782 dated Jun. 3, 2005.

International Search Report for PCT/US2004/038783 dated May 31, 2005.

International Search Report for PCT/US2006/020249 dated Sep. 27, 2006.

International Search Report for PCT/US2006/030993 dated Feb. 22, 2007.

International Search Report for PCT/US2007/012867 dated Nov. 16, 2007.

International Search Report for PCT/US2007/014457 dated Jul. 15, 2008.

International Search Report for PCT/US2007/021541 dated Jul. 18, 2008.

International Search Report for PCT/US2008/001762 dated Jun. 17, 2008.

International Search Report for PCT/US2010/032568 dated Jul. 30, 2010.

International Search Report for PCT/US2011/031428 dated Jun. 30, 2011.

International Search Report for PCT/US2011/059243 dated Feb. 20, 2012.

International Search Report for PCT/US2012/071519 dated Mar. 8, 2013.

International Search Report for PCT/US2013/067705 dated Dec. 10, 2013.

International Search Report for PCT/US2013/067711 dated Jun. 2, 2014.

International Search Report for PCT/US2014/021142 dated Mar. 6, 2014.

International Search Report for PCT/US2014/57978 dated Dec. 14, 2014.

Inwald, D. P. et al,"Platelet and leucocyte activation in childhood sickle cell disease: association with nocturnal hypoxaemia," British Journal of Haematologyl 11:474-481, Nov. 2000.

Ishikawa, F. et al., "Chemotherapy-resistant human AML stem cells home to and engraft within the bone-marrow endosteal region," Nature Biotechnology 25(11):1315-1321, Nov. 2007.

Issekutz, T., "Inhibition of in Vivo Lymphocyte Migration of Inflammation and Homing to Lymphoid Tissues by the TA-2 Monoclonal Antibody. A Likely Role for VLA-4 in Vivo," Journal of Immunology 147:4178-4184, 1991.

Itai, S. et al., "Differentiation-dependent Expression of I and Sialyl I Antigens in the Developing Lung of Human Embryos and in Lung Cancers," Cancer Research 50: 7603-7611, 1990.

Jeffrey et al.,"Affinity Chromatography of Carbohydrate-Specific Immunoglobulins: Coupling of Oligosaccharides to Sepharose ," Biochem. Biophys. Res. Commun. 62:608-613, 1975.

Jentsch, K.D. et al., "Inhibition of Human Immunodeficiency Virus Type I Reverse Transcriptase by Suramin-related Compounds," the Journal of General Virology 68(8):2183-2192, 1987.

Jentsch, TJ et al. "Ion Channels: Function Unravelled by Dysfunction," Nature Cell Biology, 6(11): 1039-1047 (Nov. 2004).

Kaila, N. et al.,"Design and synthesis of sialyl Lewis(x) mimics as E- and P-selectin inhibitors," Med Res Rev 22(6):566-601, Nov. 2002.

Kaila, N. et al.,"β-C-Mannosides as Selectin Inhibitors," Journal of Medicinal Chemistry 45(8): 1563-1566, 2002.

Kannagi et al.,"New Globoseries Glycosphingolipids in Human Teratocarcinoma Reactive with the Monoclonal Antibody Directed to a Developmentally Regulated Antigen, Stage-specific Embryonic Antigen 3," J. Biol. Chem. 258(14):8934-8942, 1983.

Kannagi et al.,"Stage-specific embryonic antigens (SSEA-3 and -4) are epitopes of a unique globo-series ganglioside isolated from human teratocarcinoma cells," Embo J. 2(12):2355-2361, 1983.

Kannagi, R. et al. "Carbohydrate-mediated cell adhesion in cancer metastasis and angiogenesis," Cancer Sci., 95(5): 377-384 (2004).

Kansas, G., "Selectins and Their Ligands: Current Concepts and Controversies," Blood, 88(9): 3259-3287 (1996).

Karalvanova et al., "Partial Characterization of Microsomal Sialyltransferase From Chicken Liver and Hepatoma Mc-29: II. Measurement of Enzyme Activities Utilizing Microsomal Glycoproteins as Exogenous Acceptors," Cancer Biochem. Biophys. 11:311-315, 1990.

Kaul, D.K. et al., "Hypoxia/reoxygenation causes inflammatory response in transgenic sickle mice but not in normal mice," the Journal of Clinical Investigation 106(3):411-420, Aug. 2000.

Kim et al., "Inhibition of the CXCR4/CXCL12 Chemokine Pathway Reduces the Development of Murine Pulmonary Metastases," Clin. Exp. Metastasis 25(3):201-211, 2008.

Kitagawa et al.,"Characterization of Mucin-Type Oligosaccharides With the Sialyl-Le.sup.a Structure From Human Colorectal Adenocarcinoma Cells," Biochem. Biophys. Res. Commun. 178(3):1429-1436, 1991.

Kitagawa et al., "Immunoaffinity Isolation of a Sialyl-Le.sup.a Oligosaccharide from Human Milk," J. Biochem. 104:591-594, 1988.

Kneuer et al: "Selectins—potential pharmacological targets?" Drug Discovery Today vol. 11, No. 21-22, pp. 1034-1040, Oct. 2006.

Ko, HL et al. "In Vitro and In Vivo Inhibition of Lectin Mediated Adhesion of Pseudomonas aeruginosa by Receptor Blocking Carbohydrates," Infection, 15(4): 21-24 (1987).

Koch, Alisa E et al., "Angiogenesis mediated by soluble forms of E-selectin and vascular cell adhesion molecule-1," Nature, 376(6540): 517-519 (1995).

(56) References Cited

OTHER PUBLICATIONS

Koenig et al., "Selectin Inhibition: Synthesis and Evaluation of Novel Sialylated, Sulfated and Fucosylated Oligosaccharides, Including the Major Capping Group of Glycam-1", Glycobiology, 7(1):79-93 (1997).

Kogan, T.P. et al.,"Novel Synthetic Inhibitors of Selectin-Mediated Cell Adhesion: Synthesis of 1,6-Bis[3-(3-carboxymethylphenyl)-r-(2-.alpha.-.sub.D-monnopyranosyloxy)p-henyl]hexane (TBC1269)," J Med. Chem 41:1099-1111, 1998.

Kogan, T.P. et al.,"Rational Design and Synthesis of Oligosaccharide Mimetics: Selectin Antagonists as Cell Adhesion Inhibitors," Abstracts of Papers, 201.sup.th ACS National Meeting, American Chemical Society, Chicago, IL, Aug. 20-24, 1995, MEDI-18.

Kogan, T.P et al.,"Rational Design and Synthesis of Small Molecule, Non-oligosaccharide Selectin Inhibitors: (.alpha.-D-Mannopyranosyloxy)biphenyl-Substituted Corboxylic Acids," J. Med. Chem. 38: 4976-4984, Dec. 22, 1995.

Kohler and Milstein,"Continuous cultures of fused cells secreting antibody of predefined specificity," Nature 256:495-497, 1975.

Kohler and Milstein,"Derivation of specific antibody-producing tissue culture and tumor lines by cell fusion," Eur. J. Immunol. 6:511-519, 1976.

Kojima and Hakomori,"Specific Interaction between Gangliotriaosylceramide ($G_{g3}$) and Sialosyllactosylceramide ($G_{M3}$) as a Basis for Specific Cellular Recognition between Lymphoma and Melanoma Cells," J. Biol. Chem. 264(34):20159-20162, 1989.

Kolb, H. C. et al.,"Development of Tool for the Design of Selectin Antagonists," Chem. Eur. J. 3(10):1571-1578, 1997.

Kolb, H. C. et al.,"Recent progress in the glycodrug area," Pure & Applied Chemistry 69(9):1879-1884, 1997.

Koprowski et al.,"Colorectal Carcinoma Antigens Detected by Hybridoma Antibodies," Somatic Cell Genetics 5(6):957-972, 1979.

Kuzuoka,"Antitumor activity of murine monoclonal antibody NCC-ST-421," Chem. Ab. 115:27344v, 1991.

Kwiatskowski et al.,"Tautornerism and Electronic Structure of Biological Pyrimidines" Adv Het Chem 1975, pp. 199-335.

Kwong et al., "An Antagonist of the Chemokine Receptor CXCR4 Induces Mitotic Catastrophe in Ovarian Cancer Cells," Mol. Cancer Ther. 8(7): 1893-1905, Jul. 2009.

Kwong, P. D. et al., "Rational Design of Vaccines to Elicit Broadly Neutralizing Antibodies to HIV-1," Cold Spring Harbor Perspectives in Medicine 1-16, 2011.

Lamblin et al., "Primary Structure Determination of Five Sialylated Oligosaccharides Derived from Bronchial Mucus Glycoproteins of Patients Suffering from Cystic Fibrosis.," Journal of Biological Chemistry 259(14):9051-9058, 1984.

Lanne, B. et al., "Binding of the galactose-specific Pseudomonas aeruginosa lectin. PA-I, to glycosphingolipids and other glycoconjugtes," Glycoconjugate Journal, 11:292-298 (1994).

Larsen et al., PADGEM-Dependent Adhesion of Platelets to Monocytes and Neutrophils is Mediated by a Lineage-Specific Carbohydrate, LNF III (CD15), Cell 63:467-474, 1990.

Lee et al.,"A new method of sequencing linear oligosaccharides on gels using charged, fluorescent coniugates" Carbohydrate Research. vol. 214, 1991, pp. 155-168, XP000226749.

Leppla, S H et al., "Anthrax Toxin Fusion Proteins for Intracellular Delivery of Macromolecules ," Journal of Applied Microbiology., 87(2): p. 284 (Aug. 1, 1999).

Ley, K. "The role of selectins in inflammation and disease," Trends in Molecular Medicine, 9(6): 263-268 (Jun. 2003).

Ley, K. et al. "Selectins in T-cell Recruitment to Non-Lymphoid Tissues and Sites of Inflammation," Nature Reviews, 4: 1-11 (May 2004).

Li, B., et al.,"Delaying Acute Graft-Versus-Host Disease in Mouse Bone Marrow Transplantation by Treating Donor Cells with Antibodies Directed at L-Selectin and a4 Integrin Prior to Infusion," Scand. J. I Immunol 59:464-468, 2004.

Lindenberg et al.,"Carbohydrate binding properties of mouse embryos," J. Reprod. Fert. 89:431-439, 1990.

Lipartiti et al.,"Monosialoganglioside GM1 Reduces NMDA Neurotoxicity in Neonatal Rat Brain," Experimental Neurology 113:301-305, 1991.

Loetscher et al., "N-terminal Peptides of Stromal Cell-derived Factor-1 with CXC Chemokine Receptor 4 Agonist and Antagonist Activities," J. Biol. Chem. 273(35):22279-22283, 1998.

Lowe et al.,"A transfected human fucosyltransferase cDNA determines biosynthesis of oligosaccharide ligand(s) for endothelial-leukocyte adhesion molecule I," Biochem. Soc. Trans. 19(3):649-653 1991.

Lowe et al.,"ELAM-1-Dependent Cell Adhesion to Vascular Endothelium Determined by a Transfected Human Fucosyltransferase cDNA," Cell 63:475-484, 1990.

Luallen, R. J. et al., "A Yeast Glycoprotein Shows High-Affinity Binding to the Broadly Neutralizing Human Immunodeficiency Virus Antibody 2G12 and Inhibits gp120 interactions with 2G12 and DC-SIGN," Journal of Virology 83(1):4861-4870; May 2009.

Macher et al.,"A Novel Carbohydrate, Differentiation Antigen on Fucogangliosides of Human Myeloid Cells Recognized by Monoclonal Antibody VIM-2," Journal of Biological Chemistry 263(21):10186-10191, 1988.

Magnani et al., "Pan-selectin Antagonist GMI-1070 affects Biomarkers of Adhesion, Activation and the Coagulation Cascade in Sickle Cell Adults at Steady State", Blood, 120, Abstract #87, Nov. 2012.

Magnani et al.,"A Monoclonal Antibody-defined Antigen Associated with Gastrointestinal Cancer Is a Ganglioside Containing Sialylated Lacto-N-fucopentaose II," Journal of Biological Chemistry 257(23):14365-14369, 1982.

Magnani et al.,"Identification of the Gastrointestinal and Pancreatic Cancer-associated Antigen Detected by Monoclonal Antibody 19-9 in the Sera of Patients as a Mucin," Cancer Res. 43:5489-5492, 1983.

Magnani, "The Discovery, Biology, and Drug Development of Sialyl Le$^a$ and Sialyl Le$^x$", Archives of Biochemistry and Biophysics, 426:122-131, May 8, 2004.

Magnani, J.,"Carbohydrate Sequences Detected by Murine Monoclonal Antibodies," Chemistry and Physics of Lipids 42:65-74, 1986.

Magnani, J.,"Potent Glycomimetic Inhibitors of the Adhesion Molecule, PA-IIL, for the Bacterial Pathogen, *Pseudomonas auroginosa*," Glycobiology 13(11): 854, Abstract No. 104, Oct. 2003.

Mann, AP et al. "Identification of Thioaptamer Ligand against E-Selectin: Potential Application for Inflamed Vasculature Targeting," PLoS One, 5(9): 1-11 (Sep. 2010).

Matsuda, Masao et al., "Heterobifunctional Ligands: Practical Chemoenzymatic Synthesis of a Cell Adhesive Glycopeptide That Interacts With Both Selectins and Integrins," J. Med. Chem. 44:715-724, 2001.

Matsui, N. M. et al.,"Heparin inhibits the flow adhesion of sickle red blood cells to Pselectin," Blood 100(10):3790-3796, Nov. 15, 2002.

Matsui, N. M. et al.,"The Novel Adhesion of Erythrocytes to P-Selectin in Sickle Cell Disease," Blood 96(11) Pt. 1:600a, Abstract #2575, Nov. 16, 2000.

Matsui, N. M.et al.,"P-selectin mediates the adhesion of sickle erythrocytes to the endothelium," Blood 98(6):1955-1962, Sep. 15, 2001.

McCavit et al., "An Analysis of the Pediatric Sub-Group From the Phase 2 Study of GMI-1070—A Novel Agent for the Vaso-Occlusive Crisis of Sickle Cell Anemia", Blood, 122(21):2206, Nov. 15, 2013.

McCavit et al., "An Analysis of the Pediatric Sub-Group From the Phase 2 Study of GMI-1070—A Novel Agent for the Vaso-Occlusive Crisis of Sickle Cell Anemia", ASH Annual Meeting 2013, Poster #56448, Dec. 8, 2013.

Menendez, A., et al., "A Peptide Inhibitor of HIV-1 Neutralizing Antibody 2G12 is not a Structural Mimic of the Natural Carbohydrate Epitope on gp120," the FASEB Journal 22:1380-1382, May 2008.

(56) References Cited

OTHER PUBLICATIONS

Moore, P. L. et al., "Evolution of an HIV Glycan-Dependent Broadly Neutralizing Antibody Epitope Through Immune Escape," Nature Medicine doi.10.1038/nm.2985 pp. 1-6, Oct. 2012.
Mosley et al., "Recent Patents Regarding the Discovery of Small Molecule CXCR4 Antagonists," Expert Opin. Ther. Patents 19(1):23-38, 2009.
Mulligan and Berg,"Selection for animal cells that express the *Escherichia coli* gene coding for xanthine-gunine phosphoribosyltransferase," Proc. Natl. Acad. Sci. USA 78:2072-2076, 1981.
Myers et al., "E-Selectin Inhibitor GMI-1271 Works in Combination with Low-Molecular Weight Heparin to Decrease Venous Thrombosis and Bleeding Risk in a Mouse Model", Blood, 124(21):593, Dec. 6, 2014.
Myers et al., "Novel E-Selectin Antagonist GMI-1271 Decreases Venous Thrombosis without Increased Bleeding Potential in a Mouse Model", ASH Annual Meeting 2012, Poster #53444, Dec. 10, 2012.
Myers et al., "Pan-Selectin Antagonist, GMI-1070 Decreases Venous Thrombosis in a Mouse Model", Blood, 118, Abstract #3273, Nov. 2011.
Nagel, R. L.,"A Knockout of a Transgenic Mouse-Animal Models of Sickle Cell Anemia," the New England Journal of Medicine 339:194-195, Jul. 16, 1996.
Narita, T. et al. "Corticosteroids and medroxyprogesterone acetate inhibit the induction of breast cancer cells," Anticancer Research, 15(6B): 2523-2527 (1995)—Abstract.
Narumi, Tetsuo et al., "Synthesis and Biological Evaluation of Selective CXCR4 Antagonists Containing Alkene Dipeptide Isosteres," Organic & Biomolecular Chemistry, 8(3): 616-621(Feb. 7, 2010).
Natarajan, M.M. et al.,"Adhesion of sickle red blood cells and damage to interleukinlbeta stimulated endothelial cells under flow in vitro," Blood 87:4845-4852. 1996.
Natoni et al., "Multiple Myeloma Cells Express Functional E-Selectin Ligands Which Can be Inhibited Both in Vitro and in-Vivo Leading to Prolongation of Survival in a Murine Transplant Model", Blood, 124(21):,4718, Dec. 6, 2014.
Nguyen, M et al., "Novel synthetic analogs 1-29 of sialyl Lewis X can inhibit angiogenesis in vitro and in vivo," Biochemical and Biophysical Research Communications, 228(3): 716-723 (Nov. 21, 1996).
Nicolaou et al.,"Total Synthesis of the Tumor-Associated Le.sup.x Family of Glycosphingolipids," J. Amer. Chem, Soc. 112:3693-3695, 1990.
Noguchi, M. et al. "A minor E-selectin ligand, CD65, is critical for extravascular infiltration of acute myeloid leukemia cells," Leukemia Research, 25: 847-853 (2001).
Norman et al., "Sialyl Lewisx(sLex) and an sLex Mimetic, CGF69669A, Disrupt E-Selectin-Dependent Leukocyte Rolling In Vivo," Blood , 91(2):475-483 (Jan. 15, 1998).
Notice of Allowance mailed Aug. 28, 2014 in U.S. Appl. No. 13/822,573.
Notice of Allowance mailed Dec. 11, 2008 in U.S. Appl. No. 11/501,464.
Notice of Allowance mailed Dec. 3, 2012 in U.S. Appl. No. 12/768,173.
Notice of Allowance mailed Feb. 9, 2011 in U.S. Appl. No. 11/973,891.
Notice of Allowance mailed May 25, 2011 in U.S. Appl. No. 12/069,436.
Notice of Allowance mailed May 9, 2012 in U.S. Appl. No. 12/370,826.
Nudelman et al.,"Novel Fucolipids of Human Aderiocarcinoma: Disialosyl Lea Antigen (III.sup.4Fuclll.sup.6NeuAcIV.sup.3NeuAcLc.sub.4) of Human Colonic Adenocarcinoma and the Monoclonal Antibody (FH7) Defining This Structure," J. Biol. Chem. 261:5487-5495,1986.
Nutku, E. et al., "Ligation of Siglec-8: a selective mechanism for induction of human eosinophil apoptosis," Blood, 101(12): 5014-5020 (2003).
Obermajer, N. et al., "Design, synthesis and activity evaluation of mannose-based DC-SIGN antagonists," Molecular Diversity 15:347-360, May 2011.
Office Action mailed Apr. 5, 2012 in U.S. Appl. No. 12/418,774.
Office Action mailed Apr. 8, 2010 in U.S. Appl. No. 11/973,891.
Office Action mailed Apr. 8, 2013 in U.S. Appl. No. 13/566,522.
Office Action mailed Aug. 13, 2008 in U.S. Appl. No. 10/992,238.
Office Action mailed Aug. 8, 2006 in U.S. Appl. No. 10/601,080.
Office Action mailed Feb. 3, 2015 in U.S. Appl. No. 13/877,633.
Office Action mailed Feb. 4, 2013 in U.S. Appl. No. 12/747,324.
Office Action mailed Feb. 11, 2013 in U.S. Appl. No. 13/566,522.
Office Action mailed Feb. 23, 2006 in U.S. Appl. No. 10/742,631.
Office Action mailed Feb. 23, 2011 in U.S. Appl. No. 11/973,891.
Office Action mailed Feb. 23, 2012 in U.S. Appl. No. 12/370,826.
Office Action mailed Feb. 6, 2008 in U.S. Appl. No. 10/992,238.
Office Action mailed Feb. 6, 2014 in U.S. Appl. No. 14/657,729 (Reissue Application of U.S. Pat. No. 8,039,442).
Office Action mailed Jan. 27, 2014 in U.S. Appl. No. 12/746,894.
Office Action mailed Jan. 31, 2014 in U.S. Appl. No. 12/418,774.
Office Action mailed Jul. 10, 2014 in U.S. Appl. No. 12/747,324.
Office Action mailed Jul. 14, 2010 in U.S. Appl. No. 12/069,436.
Office Action mailed Jul. 16, 2014 in U.S. Appl. No. 13/877,633.
Office Action mailed Jul. 8, 2011 in U.S. Appl. No. 12/370,826.
Office Action mailed Jun. 7, 2013 in U.S. Appl. No. 12/746,894.
Office Action mailed Jun. 14, 2007 in U.S. Appl. No. 10/992,480.
Office Action mailed Jun. 19, 2012 in U.S. Appl. No. 12/768,173.
Office Action mailed Jun. 2, 2006 in U.S. Appl. No. 10/601,080.
Office Action mailed Jun. 20, 2013 in U.S. Appl. No. 13/224,847.
Office Action mailed Jun. 23, 2010 in U.S. Appl. No. 11/920,499.
Office Action mailed Jun. 6, 2005 in U.S. Appl. No. 10/742,631.
Office Action mailed Mar. 13, 2015 in U.S. Appl. No. 13/785,439.
Office Action mailed Mar. 18, 2013 in U.S. Appl. No. 13/224,847.
Office Action mailed Mar. 20, 2013 in U.S. Appl. No. 13/081,068.
Office Action mailed Mar. 25, 2011 in U.S. Appl. No. 12/370,826.
Office Action mailed Mar. 31, 2015 in U.S. Appl. No. 14/080,926.
Office Action mailed Mar. 5, 2015 in U.S. Appl. No. 12/747,324.
Office Action mailed May 10, 2011 in U.S. Appl. No. 12/302,092.
Office Action mailed May 15, 2013 in U.S. Appl. No. 13/081,068.
Office Action mailed May 25, 2011 in U.S. Appl. No. 12/304,879.
Office Action mailed May 28, 2008 in U.S. Appl. No. 11/501,464.
Office Action mailed May 8, 2014 in U.S. Appl. No. 13/822,573.
Office Action mailed Nov. 2, 2005 in U.S. Appl. No. 10/742,631.
Office Action mailed Nov. 25, 2011 in U S. Appl. No. 13/093,611.
Office Action mailed Nov. 27, 2012 in U.S. Appl. No. 12/746,894.
Office Action mailed Oct. 13, 2010 in U.S. Appl. No. 11/920,499.
Office Action mailed Oct. 13, 2011 in U.S. Appl. No. 12/418,774.
Office Action mailed Oct. 16, 2013 to U.S. Appl. No. 12/747,324.
Office Action mailed Oct. 29, 2010 in U.S. Appl. No. 12/069,436.
Office Action mailed Sep. 12, 2008 in U.S. Appl. No. 11/501,464.
Office Action mailed Sep. 20, 2010 in U.S. Appl. No. 11/973,891.
Office Action mailed Sep. 25, 2007 in U.S. Appl. No. 10/992,238.
Office Action mailed Sep. 25, 2014 in U.S. Appl. No. 14/057,729.
Office Action mated Sep. 27, 2011 in U.S. Appl. No. 12/304,879.
Orhlein, R.,"Carbohydrates and Derivatives as Potential Drug Candidates with Emphasis on the Selectin and Linear-B Area," Mini Reviews in Medicinal Chemistry 1: 349-361, 2001.
Oxford Textbook of Oncology, vol. 1, published 1995 by Oxford University Press, pp. 447-453.
Palcic et al.,"A Bisubstrate Analog Inhibitor for .alpha.(1.fwdarw.2)-Fucosyltransferase," J. Biol. Chem. 264:17174-17181, 1989.
Palcic et al.,"Enzymic Synthesis of Oligosaccharides Terminating in the Tumor-Associated Sialyl-Lewis-a Determinant," Carbohydr. Res. 190:1-11, 1989.
Palcic et al.,"Regulation of N-Acetylglucosaminyltransferase V Activity. Kinetic Comparisons of Parental, Rous Sarcoma Virus-Transformed BHK, and .sub.L-Phytohemagglutinin-Resistant BHK Cells Using Synthetic Substrates and an Inhibitory Substrate Analog," J. Biol. Chem. 265:6759-6769, 1990.

(56) References Cited

OTHER PUBLICATIONS

Palma-Vargas, J.M. et al.,"Small-Molecule Selectin Inhibitor Protects Against Liver Inflammatory Response After Ischemia and Reperfusion," J. Am. Coll. Surg. 185: 365-372, 1997.

Patton, J. T. et al.,"GMI-1070: a Small Glycomimetic, Pan-seiectin Antagonist that Improves Blood Flow and Inhibits Blood Cell Adhesion in Sickle Mice," Abstract ID:ABSTY-5APYL-CA6TP-V2ET6, Sep. 2, 2005.

Payre, et al.,"Chemoenzymatische Synthese eines zweifach modifizierten Pentasaccharids als Substrat fur einen alpha-Amylase-Assay durch Fluoreszenz-loschung" Angew. Chem., vol. 107, No. 11, 1995 pp. 1361-1364.

Payre, N. et al., "Chemoenzymatic Synthesis of a Modified Pentasaccharide as a Specific Substrate for a Sensitive Assay of a-Amylase by Fluorescence Quenching," Angew. Chem. Int. Ed. Engl. 34(11): 1239-1241 (1995).

Pejchal R. et al., "A Potent and Broad Neutralizing Antibody Recognizes and Penetrates the HIV Glycan Shield," Science 334:1097-1103, Nov. 2011.

Pentelute, Brad et al., "A Semisynthesis Platform for Investigating Structure-Function Relationships in the N-Terminal Domain of the Anthrax Lethal Factor," ACS Chemical Biology. 5(4): 359-364 (Apr. 2010).

Pentelute, Brad L. et al., "Chemica 1 1-16 dissection of protein translocation through the anthrax toxin pore" Angewandte Chemie, 50(10): 2294-2296 (Mar. 1, 2011).

Perret, S. et al,."Structural basis for the interaction between human milk oligosaccharides and the bacterial lectin PA-IIL of Pseudomonas aeruginosa," Biochem. J. 389: 325-332, 2005. cited by other.

Phillips et al., "ELAM-1 Mediates Cell Adhesion by Recognition of a Carbohydrate Ligand, Sialyl-Le.sup.x," Science 250:1130-1132, 1990.

Picker et al.,"The Neutrophil Selectin LECAM-1 Presents Carbohydrate Ligands to the Vascular Selectins ELAM-1 and GMP 140" Cell 66:921-933, 1991.

Price et al., "Breast Cancer Cells Metastasize to Bone through E-Selectin Positive Vascular Gateways", AACR Annual Meeting 2014, Poster #4831, Apr. 9, 2014.

Prokazova et al., "Sialylated lactosyiceramides. Possible inducers of non-specific immunosuppression and atherosclerotic lesions," European Journal of Biochemstry 172:1-6, 1988.

Purton, L. E. et al., "Limiting Factors in Murine Hematopoietic Stem Cell Assays," Cell Stem Cell 1: 263-270, Sep. 2007.

Rapoport, E. et al., "Probing Slate Acid Binding Ig-Like Lectins (Siglecs) with Sulfated Oligosaccharides," Biochemistry (Moscow), 71(5): 496-504 (2006).

Rauvala et al., "Studies on Cell Adhesion and Recognition. I. Extent and Specificity of Cell Adhesion Triggered by Carbohydrate-reactive Proteins (Glycosidases and Lectins) and by Fibronectin," J. Cell Biol. 88:127-137, 1981.

Reina, J. J. et al., "1,2-Mannobioside Mimic: Synthesis, DC-SIGN Interaction by NMR and Docking, and Antiviral Activity" ChemMedChem 2:1030-1036, 2007.

Rice and Bevilacqua,"An Inducible Endothelial Cell Surface Glycoprotein Mediates Melanoma Adhesion," Science 246:1303-1306, 1989.

Richert et al., "Inhibition of CXCR4 by CTCE-9908 Inhibits Breast Cancer Metastasis to Lung and Bone," Oncology Reports 21:761-767, 2009.

Ruoslahti and Pierschbacher,"New Perspectives in Cell Adhesion: RGD and Integrins," Science 238:491-497, 1987.

Sackstein, "The Biology of CD44 and HCELL in Hematopoiesis: The 'Step 2-Bypass Pathway' and Other Emerging Perspectives", Current Opinion in Hematology, 18(4):239-248 (2011).

Sakurai et al.,"Selection of a Monoclonal Antibody Reactive with a High-Molecular-Weight Glycoprotein Circulating in the Body Fluid of Gastrointestinal Cancer Patients," Cancer Research 48:4053-4058, 1988.

Sastry et al.,"Cloning of the immunological repertoire in *Escherichi coli* for generation of monoclonal catalytic antibodies: Construction of a heavy chain variable region-specific cDNA library," Proc. Natl. Acad. Sci. USA 86:5728-5732, 1989.

Scanlan, C. N. et al., "Exploiting the Defensive Sugars of HIV-1 for Drug and Vaccine Design," Nature 446:1038-1045, Apr. 2007.

Scanlan, C. N. et al., "The Broadly Neutralizing Anti-Human Immunodeficiency Virus Type 1 Antibody 2G12 Recognizes a Cluster of a1-2 mannose Residues on the Outer Face of gp120," Journal of Virology 76:7306-7321, Jul. 2002.

Scharfman, A. et al.,"Pseudomonas aeruginosa binds to neoglycoconjugates bearing mucin carbohydrate determinants and predominantly to sialyl-Lewis x conjugates," Glycobiology 9(8): 757-764, 1999.

Scharfman, A. et al.,"Recognition of Lewis x Derivatives Present on Mucins by Flagellar Components of Pseudomonas aeruginosa." Infection and Immunity 69(9): 5243-5248, Sep. 2001.

Schief, W. R. et al., "Challenges for Structure-Based HIV Vaccine Design," Current Opinion in HIV and AIDS 4:431-440, 2009.

Schwizer, D. et al. "Pre-organization of the Core Structure of E-Selectin Antagonist," Chemistry—A European Journal, 18(5): 1342-1351 (Jan. 2012).

Shan, M. et al., "HIV-1 gp120 Mannoses Induce Immunosuppressive Responses from Dendritic Cells," PLoS Pathogens 3(11):e169 1637-1650, Nov. 2007.

Shitara et al.,"Application of Anti-Sialyl Le.sup.a Monoclonal antibody, KM231, for Immunotherapy of Cancer," Anticancer Res. 11:2003-2014, 1991.

Simanek Eric A. et al. "Selectin-carbohydrate interactions: from natural ligands to designed mimics", Chemical Reviews vol. 96, No. 2, pp. 833-862, Jan. 1998.

Simon et al, "Effects of Selectin Antagonist GMI-1070 on the Activation State of Leukocytes in Sickle Cell Patients not in Crisis" ASH Annual Meeting 2010, Poster #32407, Dec. 6, 2010.

Simon et al., "Inhibition of E-Selectin Inflammatory Function by the Glycomimetic GMI-1070" Blood, 118, Abstract #851, Nov. 2011.

Simon et al., "Mightier than the sickle cell (editorial)", Blood, 116(10), 1633, Sep. 9, 2010.

Singh et al., "Evaluation of a CXCR4 Antagonist in a Xenograft Mouse Model of Inflammatory Breast Cancer," Clin. Exp. Metastasis 27:233-240, Mar. 2010.

Sipkins, Dorothy A. et al., "In Vivo Imaging of Specialized Bone Marrow Endothelial Microdomains for Tumor Engraftment," Nature Pub. Group GB 435 (7044):969-973, Jun. 2005.

Siuzdak et al.,"Examination of the Sialyl Lewis X—Calcium Complex by Electrospray Mass Spectrometry," Bioorganic & Medicinal Chemistry Letters 4(24): 2863-2866, 1994.

Solovey et al.,"Circulating Activated Endothelial Cells in Sickle Cell Anemia," the New England Journal of Medicine 337:1584-1590, Nov. 27, 1997.

Solovey, AA et al. "Modulation of endothelial cell activation in sickle cell disease: a pilot study," Blood, 97(7): 1937-1941 (Apr. 2001).

Sprengard, U. et al.,"Synthesis and Biological Activity of Novel Sialyl-Lewis.sup.X Conjugates," Bioorganic & Medicinal Chemistry Letters 6(5): 509-514, 1996.

Stanley and Atkinson, "The LEC11 Chinese Hamster Ovary Mutant Synthesizes N-Linked Carbohydrates Containing Sialylated, Fucosylated Lactosamine Units. Analysis by One- and Two-Dimensional H NMR Spectrosoopy," J. Biol. Chem. 263(23):11374-11381, 1988.

Steele et al., "A Small Molecule Glycomimetic Antagonist of E-selectin (GMI-1271) Prevents Pancreatic Tumor Metastasis and Offers Improved Efficacy of Chemotherapy", AACR Annual Meeting 2014, Poster #4503, Apr. 8, 2014.

Steele et al., "A Small Molecule Glycomimetic Antagonist of E-selectin (GMI-1271) Prevents Pancreatic Tumor Metastasis and Offers Improved Efficacy of Chemotherapy", Cancer Res, 74:Abstract4503, Oct. 1, 2014.

Stephens and Cockett,"The construction of highly efficient and versatile set of mammalian expression vectors," Nucleic Acids Research. 17:7110, 1989.

(56) References Cited

OTHER PUBLICATIONS

Stevenson, J. et al.,"Differential metastasis inhibition by clinically relevant levels of heparins," Clin. Cancer Res. 11(19): 7003-7011 (2005).
Streeter et al.,"Immunohistologic and Functional Characterization of a Vascular Addressin Involved in Lymphocyte Homing into Peripheral Lymph Nodes," Journal of Cell Biology 107: 1853-1862, 1988.
Stroud et al.,"Extended Type 1 Chain Glycosphingolipids: Dimeric Le.sup.a (III.sup.4V.sup.4Fuc.sub.2Lc.sub.6) as Human Tumor-associated Antigen," J. Biol. Chem. 266(13):8439:8446, 1991.
Styles et al., GMI-1070, a Pan-Selectin Inhibitor: Safety and PK in a Phase 1/2 Study in Adults with Sickle Cell Disease, ASH Annual Meeting 2010, Poster #31824, Dec. 4, 2010.
Supplementary European Search Report in EP 03739223 dated Jan. 16, 2009.
Suzuma, I. et al. "Contribution of E-Selectin to Cellular Infiltration during Endotoxin-Induced Uveitis," Invest. Ophthalmol. Vis. Sci., 39: 1620-1630 (1998).
Svenson and Lindberg,"Coupling of Acid Lablle *Salmonella* Specific Oligosaccharides to Macromolecular Carriers," J. Immunol. Meth. 25:323-335, 1979.
Symon, FA et al. "Selectins and their Counter receptors: a bitter sweet attraction," Thorax, 51: 1155-1157 (1996).
Tabarani G. et al., "Mannose Hyperbranched Dendritic Polymers Interact with Ciustered Organization of DC-SGIN and Inhibit gp120 Binding," FEBS Letters 580:2402-2408, Mar. 2006.
Takada et al.,"Adhesion of Human Cancer Cells to Vascular Endothelium Mediated by a Carbohydrate Antigen, Sialyl Lewis A.sup.1," Biochem. Biophys. Res. Commun. 179(2):713-719, 1991.
Takahashi, Takashi et al., "Design and Synthesis of a Water-Soluble Taxol Analogue : Taxol-Sialyl Conjugate," Bioorg. & Med. Chem. Letters 8:113-116, 1996.
Takeichi, M.,"Cadherins: a molecular family essential for selective cell-cell adhesion and animal morphogenesis," Trends Genet. 3(8):213-217, 1987.
Tamamura, H. et al. "Identification of a New Class of Low Molecular Weight Antagonists against the Chemokine Receptor CXCR4 Having the Dipicolylamine-Zinc(II) Complex Structure" J. Med. Chem., 49: 3412-3415 (2006).
Tanaka, T. et al. "Azamacrocyclic Metal Complexes as CXCR4 Antagonists," ChemMedChem, 6: 834-839(2011).
Tedder, TF et al. "The selectins: vascular adhesion molecules," FASEB J, 9(10): 866-73 (1995).
Telen et al., "GMI 1070: Reduction in Time to Resolution of Vaso-Occlusive Crisis and Decreased Opioid Use in a Prospective, Randomized, Multi-Center Double Blind, Adaptive Phase 2 Study in Sickle Cell Disease" Blood, 122(21):776, Nov. 15, 2013.
Telen et al., "Randomized phase 2 study of GMI-1070 in SCD: reduction in time to resolution of vaso-occlusive events and decreased opiod use", Blood, 125(17):2656-2664, Apr. 23, 2015.
The Merck Manual of Diagnosis and Therapy, Seventeenth Edition, published 1999 by Merck Research Laboratories, pp. 397, 398, 948,949, 1916, 1979-1981.
Thoma G. et al., "A readily Available, Highly Potent E-Selectin Antagonist," Agnew. Chem. Int. Ed. 40(19): 3644-3647, 2001.
Thoma, G. et al.,"Nanomolecular E-Selectin Inhibitors: 700-fold potentiation of affinity by multivalent ligand presentation," Journal of the American Chemical Society, 123(41): 10113-10114 (Oct. 17, 2001).
Thoma, G. et al.,"Preorganization of the Bioactive Conformation of Sialyl Lewis.sup.X Analogues Correlates with Their Affinity to E-Selectin," Agnew. Chem. Int. Ed. 40(10): 1941-1945, 2001.
Thoma, G. et al.,"Synthesis and biological evaluation of a potent E-selectin antagonist," J. Med. Chem. 42 (23): 4909-4913, Nov. 18, 1999.
Thoma, G. et al.,"Synthesis and Biological Evaluation of a Sialyl Lewis X Mimic with Significantly Improved E-selectin Inhibition," Bioorganic & Medicinal Chemistry Letters 11: 923-925, 2001.

Tilton, R.G.,"Endotoxin-Induced Leukocyte Accumulation in Aqueous Fluid of Rats is Decreased by a Small Molecule Selectins" Investigative Opthalmology & Visual Science 37(3): S918, Abstract No. 4227, Feb. 15, 1996.
Titz et al., "Mimetics of Sialyl Lewisx: The Pre-Organization of the Carboxylic Acid is Essential for Binding to Selectins", Chimia, 61:194-197, 2007.
Titz, A. et al., "Probing the carbohydrate recognition domain of E-selectin: The importance of the acid orientation in sLex mimetics," Bioorg. Med. Chem., 18(1): 19-27 (2010).
Toepfer, et al., "Synthesis of novel mimetics of the sialyl Lewis X determinant," Tetrahedron Letter, 36(50): 9161-9164 (1995).
Totani, K. et al., "Chemoenzymatic synthesis and application of glycopolymers containing multivalent sialyloligosaccharides with a poly(L-glutamic acid) backbone for inhibition of infection by influenza viruses" Glycobiology, 13(5): 315-326 (2003).
Trouet et al., "A covalent linkage between daunorubicin and proteins that is stable in serum and reversible by lysosomal hydrolases, as required for a lysosomotropic drug-carrier conjugate: In vitro and in vivo studies," Proc. Natl. Acad. Sci. USA 79:626-629, 1982.
Turhan, et al.,"Primary role for adherent leukocytes in sickle cell vascular occlusion: A new paradigm," Proceedings of the National Academy of Sciences of the United States of America 99(5):3047-3051, Mar. 5, 2002.
Turner et al., "Molecular Basis of Epithelial Barrier Regulation From Basic Mechanisms to Clinical Application," the American Journal of Pathology, 169(6): 1901-1909 (Dec. 2006).
Tyrrell, D. et al. "Structural requirements for the carbohydrate ligand of E-selectin," PNAS, 88: 10372-10376 (Nov. 1991).
U.S. Appl. No. 10/601,080, filed Jun. 19, 2003.
U.S. Appl. No. 10/742,631, filed Dec. 19, 2003.
U.S. Appl. No. 10/992,238, filed Nov. 18, 2004.
U.S. Appl. No. 11/920,499, filed Nov. 16, 2007.
U.S. Appl. No. 12/302,092, filed Nov. 24, 2008.
U.S. Appl. No. 12/304,879, filed Dec. 15, 2008.
U.S. Appl. No. 12/418,774, filed Apr. 6, 2009.
U.S. Appl. No. 13/081,068, filed Nov. 15, 2013.
U.S. Appl. No. 13/093,611, filed Apr. 25, 2011.
U.S. Appl. No. 13/224,847, filed Sep. 2, 2011.
U.S. Appl. No. 13/566,522, filed Aug. 3, 2012.
U.S. Appl. No. 13/785,439, filed Mar. 5, 2013.
U.S. Appl. No. 13/822,573, filed Mar. 12, 2013.
U.S. Appl. No. 13/877,633, filed Jun. 17, 2013.
U.S. Appl. No. 14/057,729, filed Oct. 18, 2013 (Re-Issue Application of U.S. Pat. No. 8,039,442).
U.S. Appl. No. 14/080,926, filed Nov. 15, 2013.
U.S. Appl. No. 14/106,662, filed Dec. 13, 2013.
Ueda et. al., "Structure-Activity Relationships of Cyclic Peptide-Based Chemokine Receptor CXCR4 Antagonists: Disclosing the Importance of Side-Chain and Backbone Functionalities," J. Med. Chem. 50:192-198, 2007.
Venkataraman, Nitya, et al., "Reawakening Retrocyclins: Ancestral Human Defensins Active Against HIV-1," Plos Biology, 7(4): 720-729 (Apr. 2009).
Wai, "Blockade of Chemokine (C-X-C motif) Receptor 4 for the Inhibition of Hepatocellular Carcinoma Metastasis," a Thesis, in partial fulfillment of requirements for Ph.D. Degree at the Univ. of Hong Kong, Jun. 2008.
Waldmann, H. et al.,"Synthesis of 2-Acetamindo-2-Deoxyglucosylasparagine Glyco-Tripeptide and -Pentapeptides by Selective C- and N-Terminal Elongation of the Peptide Chain," Carbohydrate Research 196: 75-93, 1990.
Walker, L. M. et al., "Rapid Development of Glycan-Specific Broad, and Potent Anti-HIV-1 gp120 Neutralizing Antibodies in an R5 SIV/HIV Chimeric Virus Infected Macaque," Proceedings of the National Academy of Sciences 106(50):20125-20129, Dec. 2011.
Walsh, GM. "Novel Therapies for Asthma—Advances and Problems," Current Pharmaceutical Design, 11(23): 3027-3038 (2005).
Walz et al., "Recognition by ELAM-1 of the Sialyl-Le.sup.X Determinant on Myeloid and Tumor Cells," Science 250:1132-1135, 1990.

(56) References Cited

OTHER PUBLICATIONS

Wang, L.X. et al., "Binding of High-Mannose-Type Oligosaccharides and Synthetic Oligomannose Clusters to Human Antibody 2G12: Implications for HIV-1 Vaccine Design," Chemistry & Biology 11:127-134, Jan. 2004.
Wang, S.K. et al., "Targeting the Carbohydrates on HIV-1: Interaction of Oligomannose Dendrons with Human Monoclonal Antibody 2G12 and DC-SIGN," Proceedings of the National Academy of Sciences 105(10):3690-3695, Mar. 2008.
Wang, Y. et al. "Effect of ginsenoside rg1 and rh1 on the expression of hla-dr, cd25, cd44, cd11c and e-selectin on dendritic cell," Zhongguo Mianyixue Zazhi, 23(1): 46-48 (2007)—Abstract.
Ward and Muliigan,"Blocking of adhesion molecules in vivo as anti-inflammatory therapy," Immunology 1: 165-171, 1994.
Wesche, Jorgen et al., "Characterization of membrane translocation by anthrax protective antigen," Biochemistry, 37(45): 15737-15746 (Nov. 10, 1998).
Whisler and Yates,"Regulation of Lymphocyte Responses by Human Gangliosides. I. Characteristics of Inhibitory Effects and the Induction of Impaired Activation," Journal of Immunology 125(5):2106-2111, 1980.
Winkler et al., "Absence or blockage of E-Selectin-Mediated Cell Adhesion Delays Hematopoietic Stem Cell", ASH Annual Meeting 2009, Abstract #564, Nov. 2009.
Winkler et al., "Absence or blockage of E-Selectin-Mediated Cell Adhesion Delays Hematopoietic Stem Cell", Blood, 114(22), Abstract #564, Dec. 7, 2009.
Winkler et al., "Administration of E-selectin Antagonist GMI-1271 Improves Survival to High-Dose Chemotherapy by Alleviating Mucositis and Accelerating Neutrophil Recovery", Blood, 122(21):2266, Nov. 15, 2013.
Winkler et al., "Administration of E-selectin Antagonist GMI-1271 Improves Survival to High-Dose Chemotherapy by Alleviating Mucositis and Accelerating Neutrophil Recovery", ASH Annual Meeting, Poster #63045, Dec. 8, 2013.
Winkler et al., "Mobilisation of Reconstituting HSC by Synergy Between G-CSF and E-Selectin Antagonist GMI-1271", Blood, 124(21):317, Dec. 6, 2014.
Winkler et al., "Vascular Niche E-Selectin Protects Acute Myeloid Leukemia Stem Cells from Chemotherapy", Blood, 124(21):620, Dec. 6, 2014.
Winkler et al., "Vascular Niche E-Selectin Regulates Hematopoietic Stem Cell Dormancy, Self Renewel and Chemoresistance", Nature Medicine, doi:10.1038/nm2969, Oct. 21, 2012.
Winnard, P. et al., "Real time non-invasive imaging of receptor-ligand interactions in vivo," J. Cell. Biochem., 90:454-463 (2003).
Winzer, K. et al. "The Pseudomonas aeruginosa Lectins PA-IL and PA-IIL are Controlled by Quorom Sensing and by RpoS," J. Bacteriol. 182(22): 6401-6411 (2000).
Wu, B. et al. "Structures of the CXCR4 Chemokine GPCR with Small-Molecule and Cyclic Peptide Antagonists," Science, 330(6007): 1066-1071 (Nov. 2010).
Wun et al., "Pan-Selectin Antagonist Rivipansel (GMI-1070) Reduces Soluble E-Selectin Levels While Improving Clinical Outcomes in SCD Vaso-Occlusive Crisis" Blood, 124(21):2704, Dec. 6, 2014.
Xu, J. et al., "Molecular insights and therapeutic targets for diabetic endothelial dysfunction," Circulation, 120: 1266-1286 (2009).
Yamazaki, F. et al.,"Synthesis of an appropriately protected core glycotetraoside, a key intermediate for the synthesis of 'bisected' complex-type glycans of a glycoprotein," Carbohydrate Research 201: 15-30, 1990.
Zeisig et al., "Effect of sialyl Lewis X-glycoliposomes on the inhibition of E-selectin-mediated tumour cell adhesion in vitro" Biochimica et Biophysica Acta (2004) 1660, pp. 31-40.
Zhan et al., "Discovery of Small Molecule CXCR4 Antagonists," J. Med. Chem. 50:5655-5664, 2007.
Zhang et al., "Chemokine CXCL 12 and its receptor CXCR4 expression are associated with perineural invasion of prostate cancer" Journal of Experimental and Clinical Cancer Research (2008) vol. 27 No. 62, pp. 1-9.
Zhang, Z. et al., "CXCR4 but not CXCR7 is mainly implicated in ocular leukocyte trafficking during ovalbumin-induced acute uveitis," Experimental Eye Research, 89:522-531 (2009).
Zheng, CX et al. "The prognostic value of preoperative levels of CEA, CA19-9 and CA72-4 in patients with colorectal cancer," World J. Gastroentero, 7(3): 431-434 (2001).
Zhou et al., "The Selectin GMP-140 Binds to Sialylated, Fucosylated Lactosaminoglycans on Both Myeloid and Nonmyeloid Cells," Journal of Cell Biology 115(2):557-564, 1991.
Zhou, G. et al. "Effect of ET-RA on expression of selectin on the surface of endothelial cell in mice with severe acute pancreatitis," Chongqing Yixue, 35(7): 624-626 (2006)—Abstract.
Zopf et al., "Affinity Purification of Antibodies Using Oligosaccharide-Phenethylamine Derivatives Coupled to Sepharose," Meth. Enzymol. 50:171-175, 1978.
Alessandro, et al., "Role of S128R polymorphism of E-selectin in colon metastasis formation," Int. J. Cancer, 121(3): 528-535 (2007).
Ali, M., et al., "Polymers bearing sLex-mimetics are superior inhibitors of E-selectin-dependent leukocyte rolling in vivo", The FASEB Journal 18(1), (2004), 152-154.
Alousi, A., et al., "Reduced-Intensity Conditioning Allogeneic Hematopoietic Stem Cell Transplantation", Clinical Advances in Hematoloav & Oncoloav. 5(7), (2007), 560-570.
Bedard et al., "Expert Opinion: Selectin Inhibitors: A Patent Review," Rights Link, 20(6):781-793, 2010.
Bennett, C. F., et al., "Inhibition of Endothelial Cell Adhesion Molecule Expression with Antisense Oligonucleotides", Journal of Immunoloav. 152(7), (1994), 3530-3540.
Berger et al., "Adoptive transfer of effector CD8+ T cells derived from central memory cells establishes persistent T cell memory in primates." J. Clin. Invest. 118(1):294-305 (2008).
Bevilacqua, et al., "Endothelial-leukocyte adhesion molecules in human disease," Ann. Rev. Med., 45: 361-378 (1994).
Bogden, A. E., et al., "Amelioration of Chemotherapy-Induced Toxicity by Cotreatment with AcSDKP, a Tetrapeptide Inhibitor of Hematopoietic Stem Cell Proliferation", Annals New York Academv of Sciences. 628, (1991), 126-139.
Bradford, G. B., et al., "Quiescence, cycling, and turnover in the primitive hematopoietic stem cell compartment", Experimental Hematoloav. 25, (1997), 445-453.
Brodt et al., "Liver endothelial E-selectin mediates carcinoma cell adhesion and promotes liver metastasis," Int. J. Cancer, 71(4): 612-619 (1997).
Burkhardt, K., et al., "The Significance of Adhesion Molecules in Nephrology", Artificial Oraans 20(5), (1996), 433-436.
Choi, S. et al., "Synthetic Multivalent Molecules: Concepts and Biomedical Applications," Wiley-Interscience, p. xxi-xxvi, 1-17, 2004.
Cottler-Fox, M.H. et al., "Stem Cell Mobilization," Amer. Sci. Hematology, 419-437, (2003).
Dagia, Nilesh et al., "G-CSF induces E-selecting ligand expression on human myeloid cells," Nature Medicine, 12(10): 1185-90, Oct. 1, 2006.
Demain et al. "Natural products for cancer chemotherapy," Microbio. Biotechnol. 4(6): 687-699, 2011.
Devereux, J., et al., "A comprehensive set of sequence analysis programs for the VAX", Nucleic Acids Research 12(1), (1984), 387-395.
Deweerdt, "Animal models: Towards a myeloma mouse," Nature, 480 (7377): S38-39 (2011).
Diaz-Ricart et al., "rPSGL-Ig" Drugs of the Future 27(4):346 (2002).
Dutta P. et al "E-selectin inhibition mitigates splenic HSC activation and myelopoiesis in hypercholesterolemic mice with myocardial infarction highlights" Arteriosclerosis, Thrombosis, and Vascular Biology 36(9):1802-08 (2016).
Dykewicz, C. "Summary of the Guidelines for Preventing Opportunistic Infections among Hematopoietic Stem Cell Transplant Recipients," Clin. Infectious Diseases, 33:139-144, Jul. 15, 2001.

(56) References Cited

OTHER PUBLICATIONS

Fruehauf, S., et al., "Protection of hematopoietic stem cells from chemotherapy-induced toxicity by multidrug-resistance 1 gene transfer," Recent Results in Cancer Research, 144, Abstract Only), (1998), 1 pQ.
Gout, et al., "Selectins and selectin ligands in extravasation of cancer cells and organ selectivity of metastasis," Clin. Exp. Metastasis, 25(4): 335-344 (2008).
Hamamoto, N., et al., "Inhibition of Dextram Sulphat Sodium (DSS)-induced Colitis in Mice by Intracolonically Administered Antibodies Against Adhesion Molecules (Endothelial Leucocyte Adhesion Molecule-1 (ELAM-1) or Intercellular Adhesion Molecule-1 (ICAM-1))", Clinical ExperimentalImmunoloqv, 117, (1999), 462-468.
Handschel J. et al., "Irradiation induces increase of adhesion molecules and accumulation of beta2-integrin-expressing cells in humans" International Journal of Radiation Oncology, Biology, Physics 45(2): 475-481 (1999).
Khatib, A.-M., et al., "Inhibition of Hepatic Endothelial E-Selectin Expression by C-raf antisense Oligonucleotides Blocks Colorectal Carcinoma Liver Metastasis", Cancer Research 62(19), (2002), 5393-5398.
Katayama, Y. et al., "PSGL-1 Participates in E-Selectin-Mediated Progenitor Homing To Bone Marrow: Evidence For Cooperation Between E-Selectin Ligands And a4 Integrin," Blood, 102:2060-2067, (2003).
Katayama, Y., et al., "CD 44 is a physiological E-selectin ligand on neutrophils", J. Exp. Med. 201(8), (2005), 1183-1189.
Kiel, M. J., et al., "SLAM Family Receptors Distinguish Hematopoietic Stem and Progenitor Cells and Reveal Endothelial Niches for Stem Cells" Cell 121 (7) (2006), 11 09-1121.
Kilgore K. S. et al., "Reducation of myocardial infarct size in vivo by carbohydrate-based glycomimetics" Journal of Pharmacology and Experimental Therapeutics, American Society for Pharmacology and Experimental Therapeutics, 284(1):427-435 (1998).
Komrokji, Rami S., et al., "The Colony-Stimulating Factors: Use to Prevent and Treat Neutropenia and Its Complications," Expert Opin.Biol. Ther., 4:1897-1910, (2004).
Kyriakides et al., Surgery, 128(2):327-31, Aug. 2000.
Lemoli et al., "Hematopoietic stem cell mobilization," Haematologica, 93 (3): 321-324 (2008).
Maly, P., et al., "The a(1,3)Fucosyltransferase Fuc-TVII Controls Leukocyte Trafficking through an Essential Role in L-, E-, and P-selection Ligand Biosynthesis", Cell. 86(4), It 1996, 643-653.
Mauch, P., et al., "Hematopoietic Stem Cell Compartment: Acute and Late Effects of Radiation Therapy and Chemotherapy", Int. J. Radiation Oncology Bioi. Phys . . . 31(5), 1995), 1319-1339.
McEver et al., "Leukocyte trafficking mediated by selectin-carbohydrate interactions," J. Biol. Chem., 270 (19): 11025-11028 (1995).
McKenzie, J. L., et al., "Low rhodamine 123 retention identifies long-term human hematopoietic stem cells with the Lin −CD34+CD38-population", Blood. 109, (2007), 543-545.
McLean P. et al., "Effects of a small molecule inhibitor of ICAM-1 and E-selectin expression on colonic inflammatory hyperalgesia and colitis" Digestive Disease 2003, Orlando FL, May 2003, abstract.

Mimeault, et al., "Stem cells: a revolution in therapeutics-recent advances in stem cell biology and their therapeutic applications in regenerative medicine and cancer therapies," Clin. Pharmacol. Therapeutics, 82(3): 252-264 (2007).
Mitsiades, et al., "Preclinical studies in support of defibrotide for the treatment of multiple myeloma and other neoplasias," Clin. Cancer Res., 15 (4): 1210-1221 (2009).
Moore, M., "Waking Up HSCs: A new Role for E-Selectin," Nat. Med., 18:16131614, (2012).
Mulligan et al., "Role of Endothelial-Leukocyte Adhesion Molecule 1 (ELAM-1) in Neutrophil-mediated Lung Injury in Rats," J Clin Invest.,88(4):1396-406, Oct. 1991.
Pamphilon et al., "Stem Cell Donation—What advice can be given to the donor?," Br. J. Haematol. 147(1):71-76, Oct. 2009, Author manuscript available at NIH Public access Aug. 1, 2012.
Pelus, "Peripheral blood stem cell mobilization: new regimens, new cells, where do we stand," Curr. Opin. Hematol., 15(4): 285-292 (2008).
Plasterk, R. H. A., et al., "The silence of the genes", Current Opinion in Genetics and Develooment 10 (2000), 562-567.
Roberge, J. Y., et al., "A Strategy for a Convergent Synthesis of N-Linked Glycopeptides on a Solid Support", Science 269(5221), (1995), 202-204.
Rood, P.M.L. et al., "E-Selectin and Very Late Activation Antigen-r Mediate Adhesion of Hematopoietic Progenitor Cells to Bone Marrow Endothelium," Ann Hematol, 79:477-484, (2000).
Sanz, M.-J., et al., "Roflumilast inhibits leukocyte-endothelial cell interactions, expression of adhesion molecules and microvascular permeability", British Journal of Pharmacology. 152(4), (2007), 481-492.
Sudhoff, T. et al., "Cutting Edge Communication: Circulating Endothelial Adhesion Molecules (sE-Selectin, sVCAM-1 and SICAM-1) During rHuG-CSF-Stimulated Stem Cell Mobilization," Jour. Hematother. & Stem Cell Res., 11:147-151 (2002).
Titz et al., "Is adamantine a suitable substituent to pre-organize the acid orientation in E-selectin antagonists?", Bioorganic & Medicinal Chemistry, 16 (2008), 1046-1056.
Todderund et al., "BMS-190394, a Selectin Inhbitor, Prevents Rat Cutaneous Inflammatory Reactions," J Pharmacal Exp Ther., 282(3):1298-304, Sep. 1997.
Togel et al., "Administered mesenchymal stem cells protect against ischemic acute renal failure through differentiation-independent mechanisms," Am. J. Physical Renal Physiol., 289:F31-42, Jul. 2005.
Winkler et al., "Absence of E-selectin at vascular niche delays hematopoietic stem cell turn-over," Blood, 110(11):188A, Nov. 2007.
Winkler et al., "Adhesion of E-selectin promotes growth inhibition and apoptosis of human and murine hematopoietic progenitor cells independent of PSGL-1," Blood, 103(5):1685-92, Mar. 1, 2004.
Witz, "The involvement of selectins and their ligands in tumor-progression," Immunol. Lett., 104 (1-2): 89-93 (2006).
Zhao T. et al. "Targeting human CD34+ hematopoietic stem cells with anti-CD45 x antimyosin light-chain bispecific antibody preserves cardiac function in myocardial infarction" Journal of Applied Physiology, 10(6):1793-1800 (2008).
Zuber et al., "Mouse models of human AML accurately predict chemotherapy response," Genes. Dev., 23 (7): 877-889 (2009).

\* cited by examiner

Synthesis of compound 10

Synthesis of compound 14

Synthesis of compound 20

Synthesis of compound 23

Synthesis of compound 25

COMPOUNDS, COMPOSITIONS AND METHODS USING E-SELECTIN ANTAGONISTS FOR MOBILIZATION OF HEMATOPOIETIC CELLS

CROSS REFERENCE TO RELATED APPLICATIONS

This application claims the benefit under 35 U.S.C. §119 (e) to U.S. Provisional Application No. 61/734,924 filed Dec. 7, 2012 and U.S. Provisional Application No. 61/784,206 filed Mar. 14, 2013, which applications are incorporated by reference herein in their entirety.

BACKGROUND

Technical Field

Agents and compositions thereof are described herein that are E-selectin antagonists and may be used as therapeutics. Methods are described for mobilizing cells from the bone marrow using the E-selectin antagonists described herein.

Description of the Related Art

Autologous hematopoietic stem cell transplantation (HSCT) is a potentially curative therapeutic approach for various malignant hematologic and lymphoid diseases. Hematopoietic stem cells (HSCs) may be collected from the blood or the bone marrow and used for repopulating hematopoiesis. Recent studies demonstrate clinical advantages of re-infusing autologous mobilized peripheral blood stem cells compared with bone marrow HSCs (see, e.g., Lemoli et al., *Haematologica* 93:321-324 (2008); Gratwohl et al., *Blood* 100:2374-86 (2002)). The cytokine, granulocyte colony-stimulating factor (G-CSF), has been the agent predominantly used in the clinic for mobilization of HSCs. More recently, a chemokine (C-X-C motif) receptor 4 (CXCR4) antagonist, AMD3100 (also called plerixafor) has been administered alone or with G-CSF for this purpose.

Not all patients treated with G-CSF have successful mobilization of peripheral blood stem cells: as high as 25% of patients with lymphomas, multiple myeloma, or acute leukemia, and in 10-20% of normal volunteers, all of whom require extended aphereses (see, e.g., Pelus, *Curr. Opin. Hematol.* 15:285-92 (2008) and references cited therein). Studies are ongoing to identify additional agents to use alone or in combination with G-CSF to reduce the multidosing requirement and to improve long term quality of life.

Therefore, a need exists in the art to identify highly effective, non-toxic, and less expensive therapeutics useful for mobilizing peripheral blood stem cells.

BRIEF SUMMARY

Briefly, provided herein are agents that are E-selectin antagonists, compositions comprising the agents, and methods for using the agents. These agents are useful for mobilizing cells from the bone marrow, including hematopoietic cells, such as hematopoietic stem cells and progenitor cells and white blood cells, such as granulocytes (including neutrophils). In other embodiments, the cells are tumor cells such as malignant tumor cells or hematologic tumor cells. Glycomimetic compounds that may be used in these methods are E-selectin antagonists as described herein.

In one embodiment, Embodiment I, a method is provided for mobilizing cells from the bone marrow in a subject comprising administering to the subject a compound (which is a glycomimetic compound that is an E-selectin antagonist) having the following formula (I):

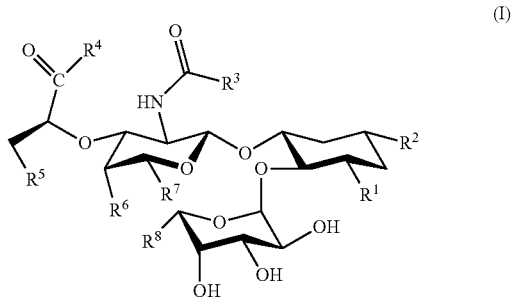

or a pharmaceutically acceptable salt, isomer, tautomer, hydrate or solvate thereof, wherein:

$R^1$ is $C_1$-$C_8$ alkyl, $C_2$-$C_8$ alkenyl, $C_2$-$C_8$ alkynyl, $C_1$-$C_8$ haloalkyl, $C_2$-$C_8$ haloalkenyl or $C_2$-$C_8$ haloalkynyl;

$R^2$ is H, $C_1$-$C_8$ alkyl, —C(=O)NH(CH$_2$)$_{1-4}$NH$_2$, —C(=O)OY where Y is $C_1$-$C_4$ alkyl, $C_2$-$C_4$ alkenyl or $C_2$-$C_4$ alkynyl, or a non-glycomimetic moiety or a linker-non-glycomimetic moiety, wherein the non-glycomimetic moiety is selected from polyethylene glycol, thiazolyl, and chromenyl;

$R^3$ is $C_1$-$C_8$ alkyl, $C_2$-$C_8$ alkenyl, $C_2$-$C_8$ alkynyl, $C_1$-$C_8$ haloalkyl, $C_2$-$C_8$ haloalkenyl, $C_2$-$C_8$ haloalkynyl or cyclopropyl;

$R^4$ is —OH or —NZ$^1$Z$^2$ where $Z^1$ and $Z^2$ are each independently H, $C_1$-$C_8$ alkyl, $C_2$-$C_8$ alkenyl, $C_2$-$C_8$ alkynyl, $C_1$-$C_8$ haloalkyl, $C_2$-$C_8$ haloalkenyl or $C_2$-$C_8$ haloalkynyl or wherein $Z^1$ and $Z^2$ join to form a ring;

$R^5$ is $C_3$-$C_8$ cycloalkyl;

$R^6$ is —OH, $C_1$-$C_8$ alkyl, $C_2$-$C_8$ alkenyl, $C_2$-$C_8$ alkynyl, $C_1$-$C_8$ haloalkyl, $C_2$-$C_8$ haloalkenyl or $C_2$-$C_8$ haloalkynyl;

$R^7$ is —CH$_2$OH, $C_1$-$C_8$ alkyl, $C_2$-$C_8$ alkenyl, $C_2$-$C_8$ alkynyl, $C_1$-$C_8$ haloalkyl, $C_2$-$C_8$ haloalkenyl or $C_2$-$C_8$ haloalkynyl; and $R^8$ is $C_1$-$C_8$ alkyl, $C_2$-$C_8$ alkenyl, $C_2$-$C_8$ alkynyl, $C_1$-$C_8$ haloalkyl, $C_2$-$C_8$ haloalkenyl or $C_2$-$C_8$ haloalkynyl.

Embodiment 2

The method of Embodiment 1, wherein (a) at least one of $R^1$, $R^3$, $R^6$, $R^7$ and $R^8$ is $C_1$-$C_8$ haloalkyl; (b) at least one of $R^3$, $R^6$, $R^7$ and $R^8$ is $C_1$-$C_8$ haloalkyl; (c) at least two of $R^1$, $R^3$, $R^6$, $R^7$ and $R^8$ are $C_1$-$C_8$ haloalkyl; (d) $R^2$ is a linker-non-glycomimetic moiety; or (e) at least one of $R^1$, $R^3$, $R^6$, $R^7$ and $R^8$ is $C_1$-$C_8$ haloalkyl, and $R^2$ is a linker-non-glycomimetic moiety.

Embodiment 3

The method of Embodiment 1 or Embodiment 2 wherein each $C_1$-$C_8$ haloalkyl is independently selected from —CH$_2$X, CH$_2$—(CH$_2$)$_m$—CH$_2$X, CHX$_2$, —CH$_2$—(CH$_2$)$_m$—CHX$_2$, —CX$_3$ and —CH$_2$—(CH$_2$)$_m$—CX$_3$, wherein m is 0-6 and X is F, Cl, Br or I.

Embodiment 4

The method of Embodiment 3 wherein at least one X is F. Embodiment 5 The method of Embodiment 3 wherein at least one $C_1$-$C_8$ haloalkyl is —$CH_2X$, —$CHX_2$ or —$CX_3$. Embodiment 6: The method of Embodiment 5 wherein X is F.

Embodiment 7

The method of any one of Embodiments 1-3 wherein $R^4$ is —OH or —$NZ^1Z^2$ wherein $Z^1$ and $Z^2$ are each $C_1$-$C_8$ alkyl. Embodiment 8: The method of Embodiment 7 wherein $Z^1$ and $Z^2$ are each —$CH_3$.

Embodiment 9

The method of any one of Embodiments 1-8, wherein $R^7$ is —$CH_2OH$, $C_1$-$C_8$ alkyl, $C_1$-$C_8$ haloalkyl. Embodiment 10: The method of Embodiment 9, wherein $R^1$ is —$CH_2OH$ or —$CHF_2$.

Embodiment 11

The method of any one of Embodiments 1-10 wherein $R^3$ is $C_1$-$C_8$ alkyl, $C_1$-$C_8$ haloalkyl, or cyclopropyl. Embodiment 12: The method of Embodiment 11, wherein $R^3$ is methyl or trifluoromethyl.

Embodiment 13

The method of any one of Embodiments 1-12, wherein $R^8$ is $C_1$-$C_8$ alkyl, $C_1$-$C_8$ haloalkyl. Embodiment 14: The method of Embodiment 13, wherein $R^8$ is methyl or trifluoromethyl.

Embodiment 15

The method of any one of Embodiments 1-14, wherein $R^6$ is —OH.

Embodiment 16

The method of any one of Embodiments 1-15 wherein $R^5$ is cyclohexyl.

Embodiment 17

The method of any one of Embodiments 1-16, wherein $R^1$ is $C_1$-$C_8$ alkyl or $C_1$-$C_8$ haloalkyl. Embodiment 18: The method of Embodiment 17, wherein $R^1$ is ethyl or —$CHF_2$.

Embodiment 19

The method of any one of Embodiments 1-18, wherein the compound of formula (I) has a structure of formula (Ia):

wherein $R^1$ is $C_1$-$C_8$ alkyl or $C_1$-$C_8$ haloalkyl;
$R^2$ is H, $C_1$-$C_8$ alkyl, —$C(=O)NH(CH_2)_{1-4}NH_2$, —$C(=O)OY$ where Y is $C_1$-$C_4$ alkyl, or a non-glycomimetic moiety or a linker-non-glycomimetic moiety, wherein the non-glycomimetic moiety is selected from polyethylene glycol, thiazolyl, and chromenyl;
$R^3$ is $C_1$-$C_8$ alkyl, $C_1$-$C_8$ haloalkyl, or cyclopropyl;
$R^4$ is —OH or —$NZ^1Z^2$ where $Z^1$ and $Z^2$ are each independently H or $C_1$-$C_8$ alkyl;
$R^7$ is —$CH_2OH$, $C_1$-$C_8$ alkyl, $C_1$-$C_8$ haloalkyl, and
$R^8$ is $C_1$-$C_8$ alkyl or $C_1$-$C_8$ haloalkyl.

Embodiment 20

The method of Embodiment 19, wherein halo is F.

Embodiment 21

The method of Embodiment 19 or Embodiment 20, wherein $R^1$ is —$CH_3$, —$CH_2CH_3$, —$CH_2F$, —$CHF_2$, —$CF_3$, —$CH_2CH_2F$, —$CH_2CHF_2$, or —$CH_2CF_3$.

Embodiment 22

The method of any one of Embodiments 19-21, wherein $R^3$ is —$CH_3$, —$CH_2F$, —$CHF_2$, or —$CF_3$.

Embodiment 23

The method of any one of Embodiments 19-22, wherein $R^4$ is —OH or —$N(CH_3)_2$.

Embodiment 24

The method of any one of Embodiments 19-23, wherein $R^7$ is —$CH_2OH$, —$CH_3$, —$CH_2F$, —$CHF_2$, or —$CF_3$.

Embodiment 25

The method of any one of Embodiments 19-24 wherein $R^8$ is —$CH_3$, —$CH_2F$, —$CHF_2$, or —$CF_3$.

Embodiment 26

The method of any one of Embodiments 1-25, wherein $R^2$ is a linker-non-glycomimetic moiety, and wherein the non-glycomimetic moiety comprises polyethylene glycol.

Embodiment 27

The method of Embodiment 26, wherein the compound of formula (I) has one of the formulae (Ib) or (Ic) described herein.

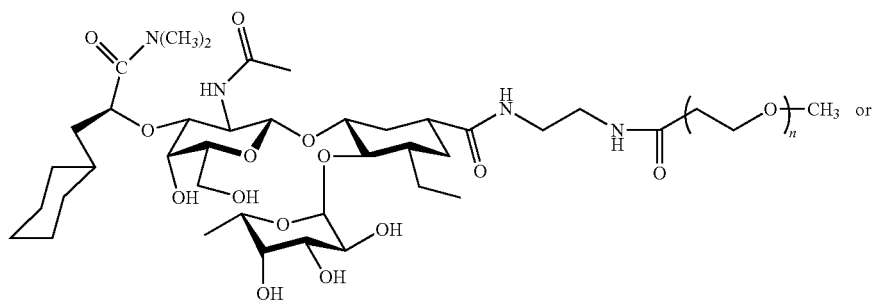
(Ib)
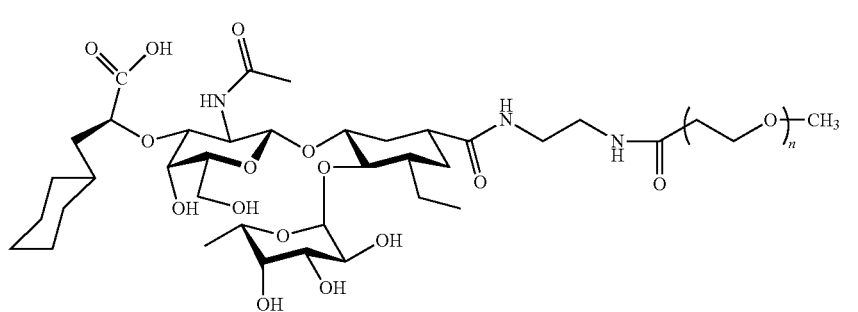
(Ic)
wherein n is 1 to 100. Embodiment 28: The method of Embodiment 27 wherein n is 4, 8, 12, 16, 20, 24, or 28.
Embodiment 29 and Embodiment 30
The method of Embodiment 27 or Embodiment 28 wherein the compound has one of the formulae:
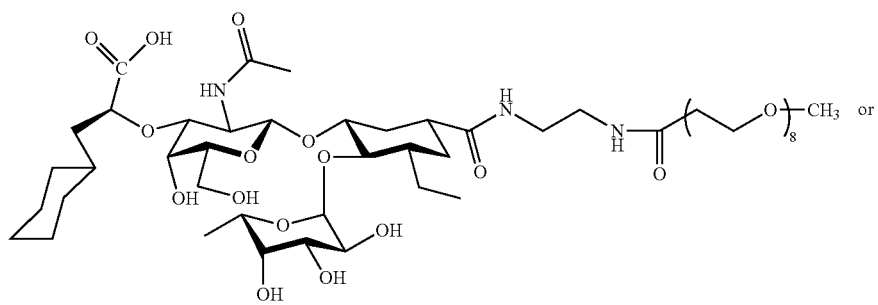
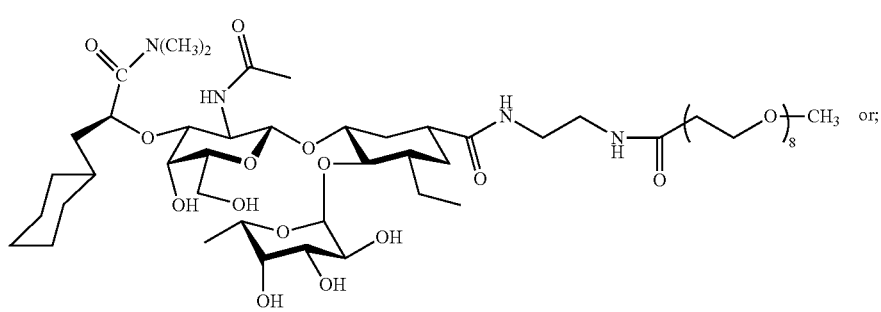

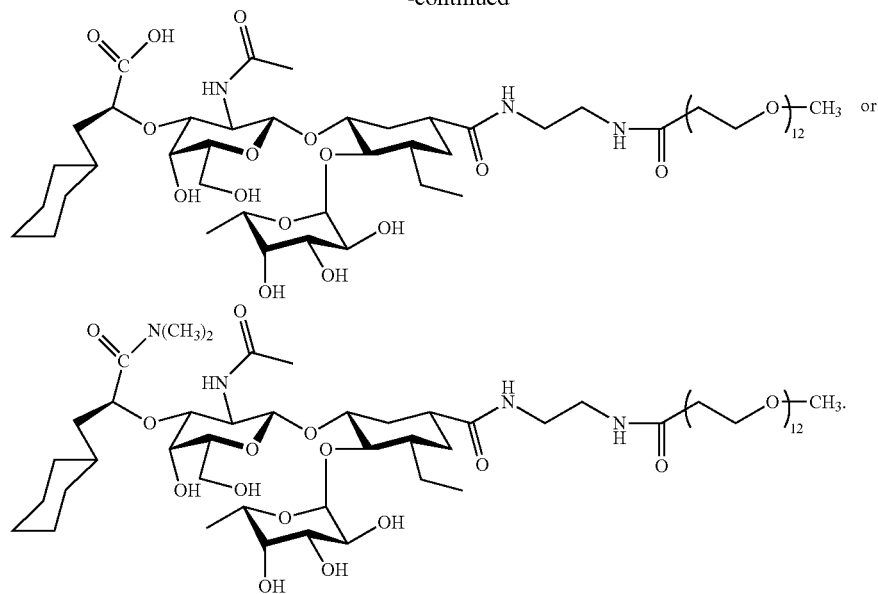

Embodiment 31

The method of any one of Embodiments 1-20, wherein $R^2$ is a linker-non-glycomimetic moiety such as thiazolyl or chromenyl, and the compound has one of the formulae described herein.

Embodiment 32

The method of Embodiment 1 or Embodiment 19 wherein the compound of formula (I) has one of the formulae (Id), (Ie), (If), (Ig), (Ih), (Ii), (Ij), or (Ik) described herein.
Embodiment 33: The method of Embodiment 32, wherein $R^2$ is a linker-non-glycomimetic moiety, and the non-glycomimetic moiety comprises polyethylene glycol.

Embodiment 34

The method of Embodiment 1, wherein the compound of formula (I) has one of the specific formulae, which are described herein.
Examples of such compounds include the following:

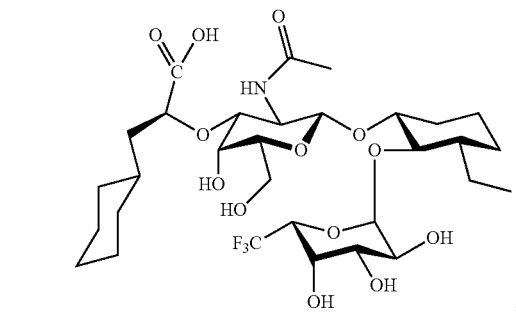

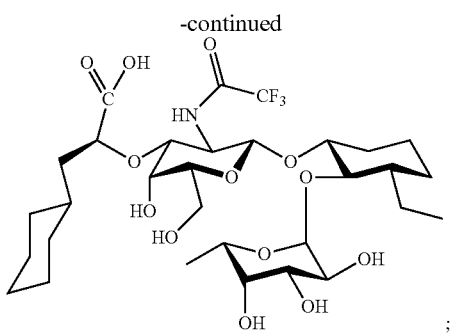

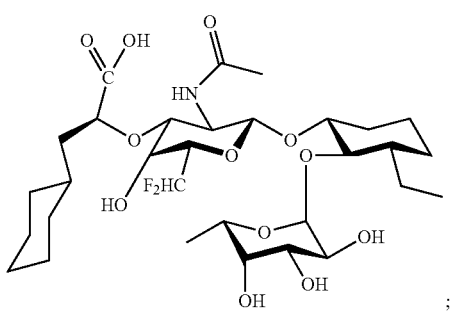

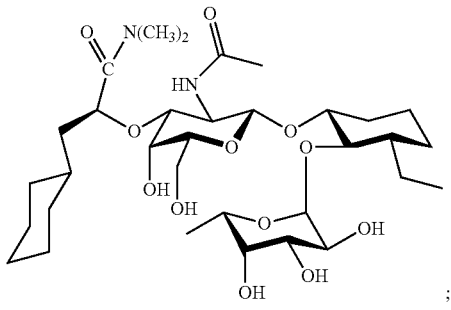

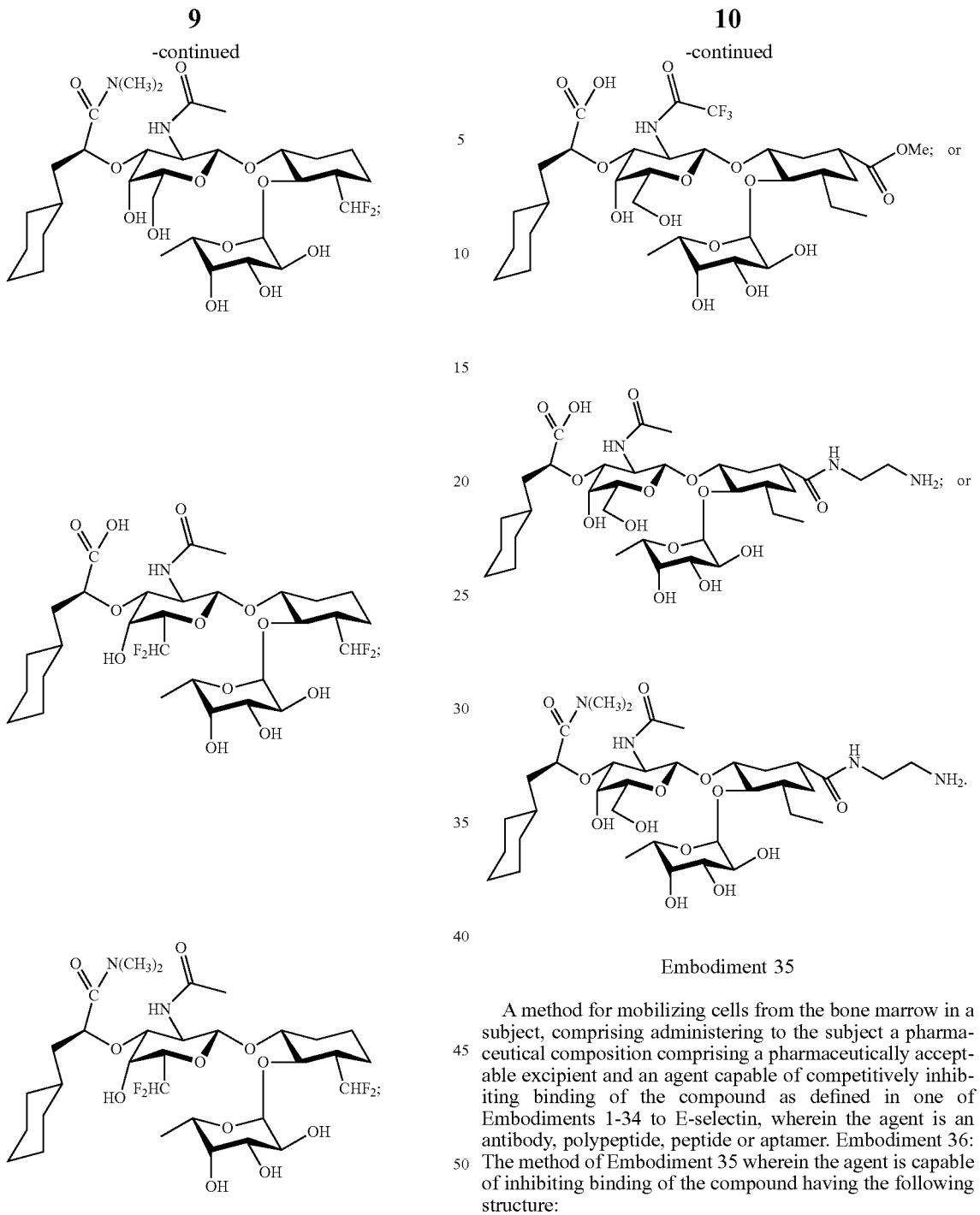

Embodiment 35

A method for mobilizing cells from the bone marrow in a subject, comprising administering to the subject a pharmaceutical composition comprising a pharmaceutically acceptable excipient and an agent capable of competitively inhibiting binding of the compound as defined in one of Embodiments 1-34 to E-selectin, wherein the agent is an antibody, polypeptide, peptide or aptamer. Embodiment 36: The method of Embodiment 35 wherein the agent is capable of inhibiting binding of the compound having the following structure:

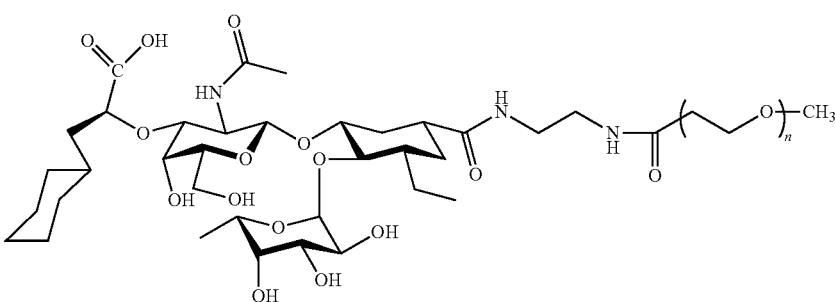

wherein n=1-100. Embodiment 37: The method of Embodiment 36, wherein n=4, 8, 12, 16, 20, 24, or 28.

Embodiment 38

The method of any one of Embodiments 1-37, wherein the cells are hematopoietic cells. Embodiment 39: The method of Embodiment 38 wherein the hematopoietic cells are hematopoietic stem cells and hematopoietic progenitor cells.

Embodiment 40

The method of Embodiment 38 wherein the hematopoietic cells are mature white blood cells.

Embodiment 41

The method of any one of Embodiments 1-37, wherein the cells are tumor cells. Embodiment 42: The method of Embodiment 41, wherein the tumor cells are hematologic tumor cells. Embodiment 43: The method of Embodiment 41, wherein the tumor cells are malignant cells.

In the following description, certain specific details are set forth in order to provide a thorough understanding of various embodiments. However, one skilled in the art will understand that the invention may be practiced without these details. In other instances, well-known structures have not been shown or described in detail to avoid unnecessarily obscuring descriptions of the embodiments. Unless the context requires otherwise, throughout the specification and claims which follow, the word "comprise" and variations thereof, such as, "comprises" and "comprising" are to be construed in an open, inclusive sense, that is, as "including, but not limited to." In addition, the term "comprising" (and related terms such as "comprise" or "comprises" or "having" or "including") is not intended to exclude that in other certain embodiments, for example, an embodiment of any composition of matter, composition, method, or process, or the like, described herein, may "consist of" or "consist essentially of" the described features. Headings provided herein are for convenience only and do not interpret the scope or meaning of the claimed embodiments.

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Also, as used in this specification and the appended claims, the singular forms "a," "an," and "the" include plural referents unless the content clearly dictates otherwise. Thus, for example, reference to "a compound" may refer to one or more compounds, or a plurality of such compounds, and reference to "a cell" or "the cell" includes reference to one or more cells and equivalents thereof (e.g., plurality of cells) known to those skilled in the art, and so forth. Similarly, reference to "a composition" includes a plurality of such compositions, and refers to one or more compositions unless the context clearly dictates otherwise. When steps of a method are described or claimed, and the steps are described as occurring in a particular order, the description of a first step occurring (or being performed) "prior to" (i.e., before) a second step has the same meaning if rewritten to state that the second step occurs (or is performed) "subsequent" to the first step. The term "about" when referring to a number or a numerical range means that the number or numerical range referred to is an approximation within experimental variability (or within statistical experimental error), and thus the number or numerical range may vary between 1% and 15% of the stated number or numerical range. It should also be noted that the term "or" is generally employed in its sense including "and/or" unless the content clearly dictates otherwise. The term, "at least one," for example, when referring to at least one compound or to at least one composition, has the same meaning and understanding as the term, "one or more."

These and other aspects of the present invention will become apparent upon reference to the following detailed description and attached drawings. All references disclosed herein are hereby incorporated by reference in their entirety as if each was incorporated individually.

DETAILED DESCRIPTION

Figure 1A:
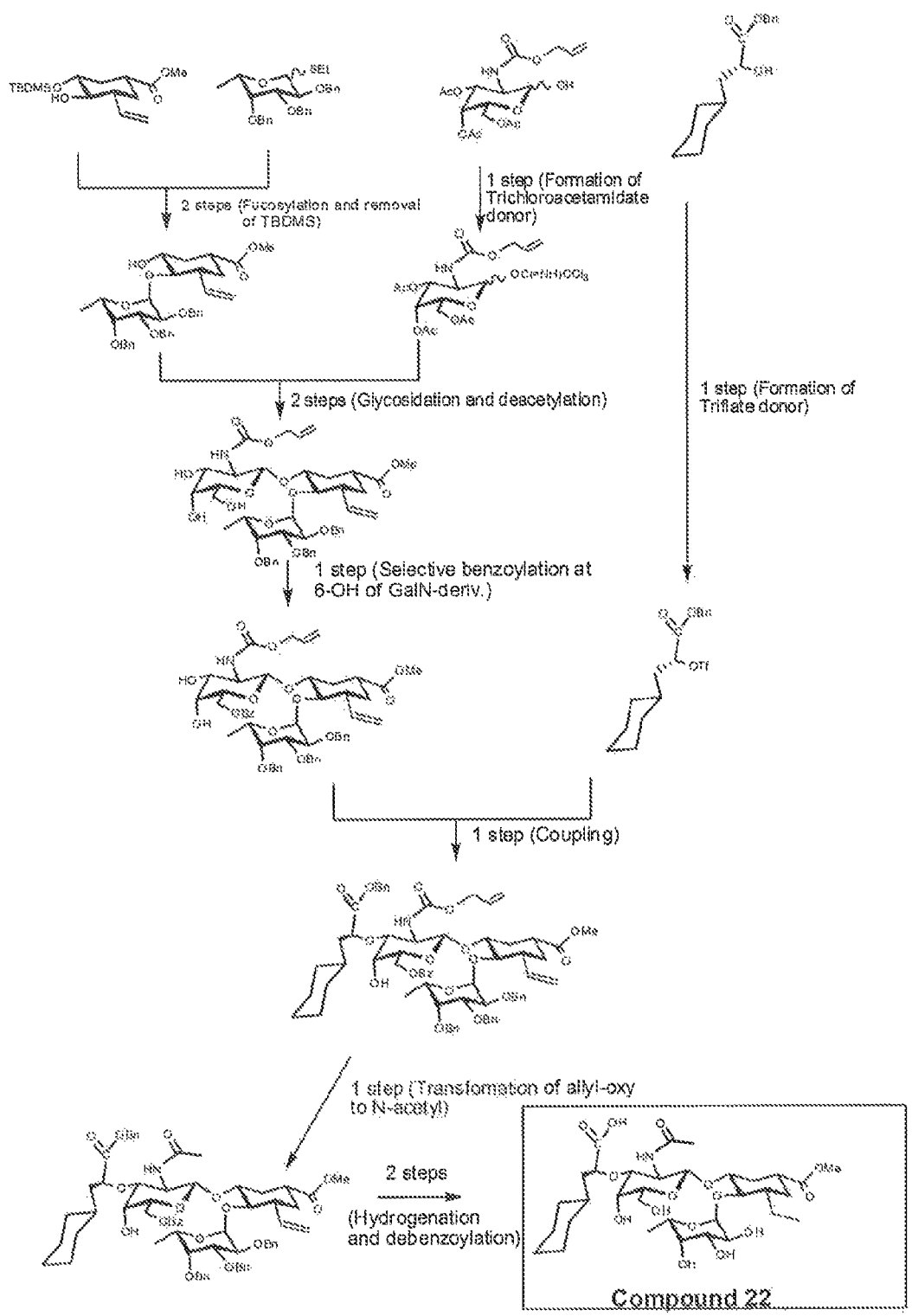
FIGS. 1A-1D present a diagram illustrating the synthesis of an embodiment (compound 25) of the compounds having formula I provided herein.
Figure 1B:
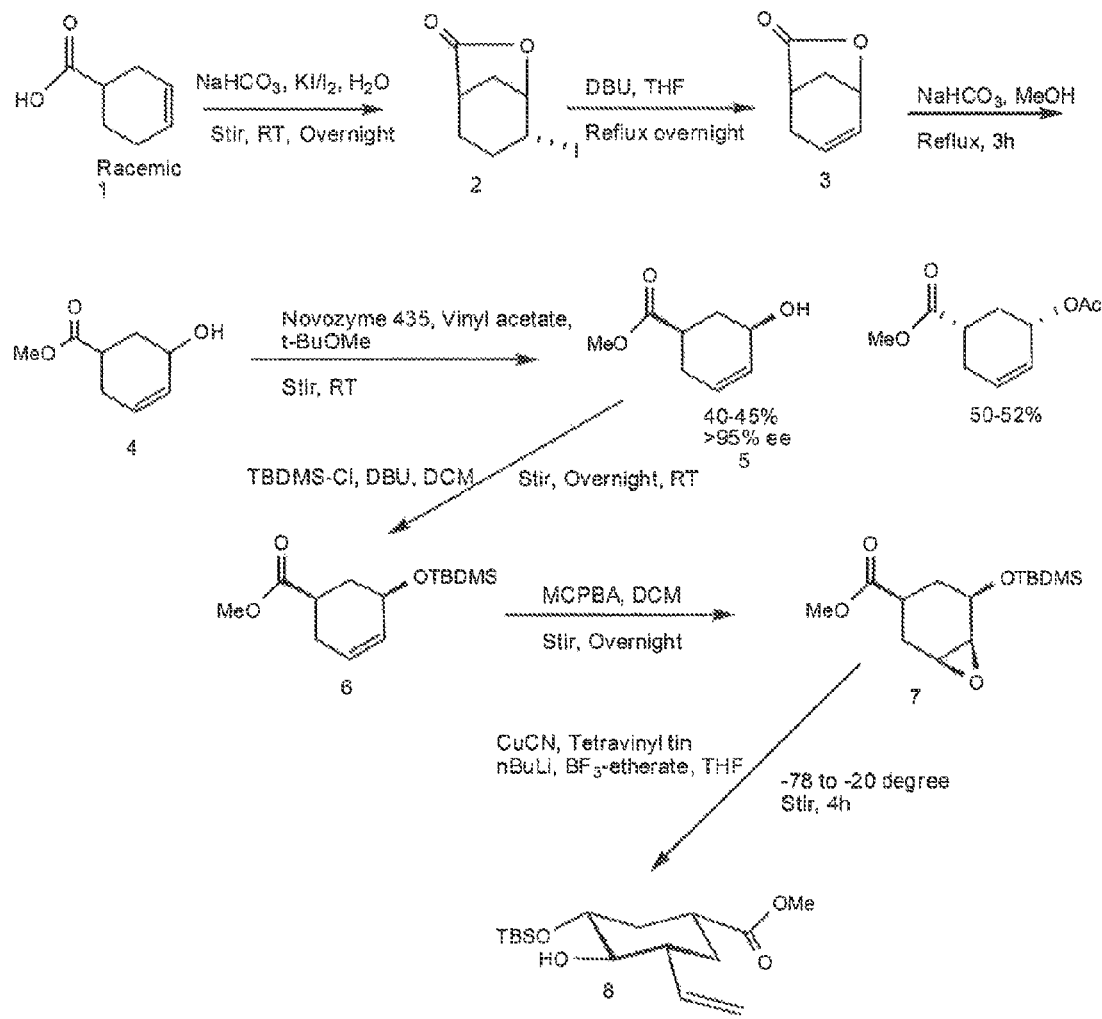
Figure 1C:
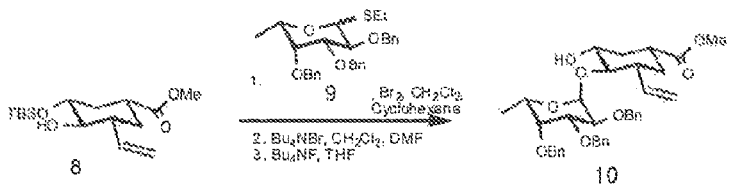
Figure 1C:
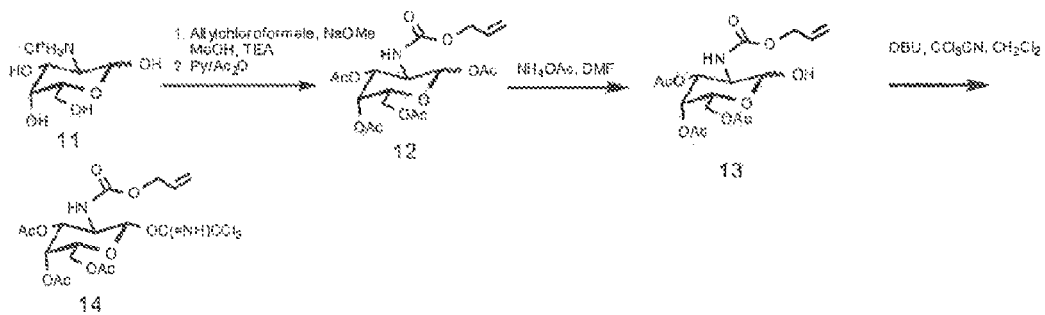
Figure 1C:
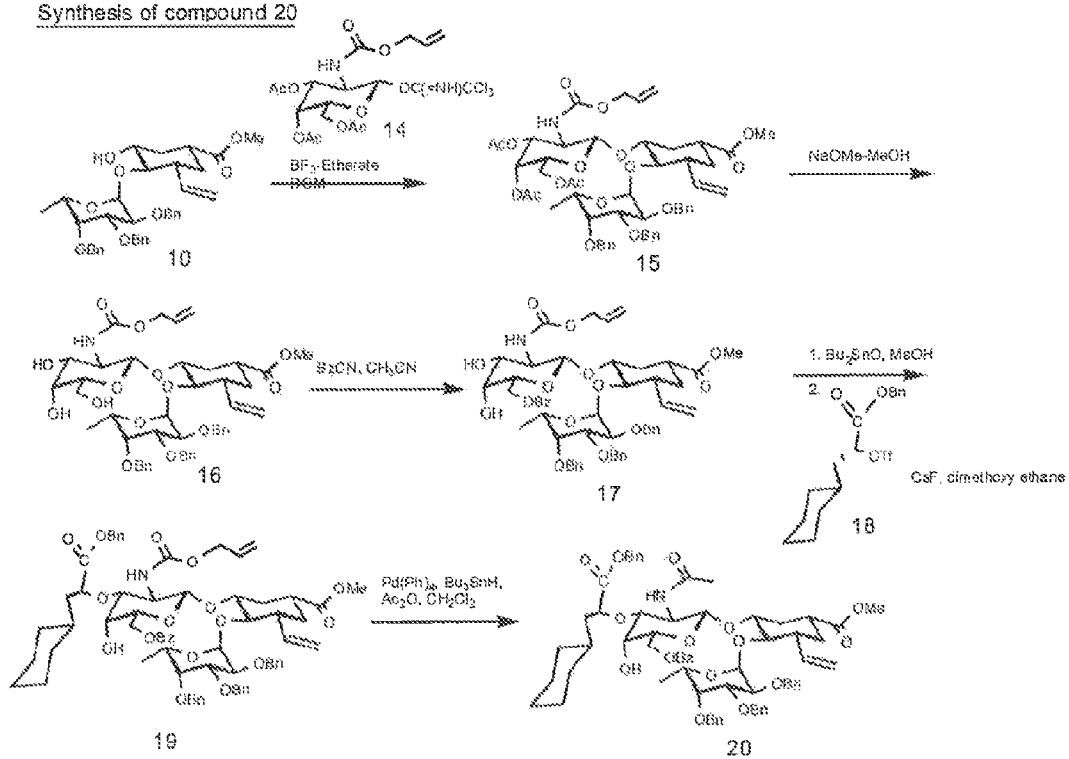
Figure 1D:
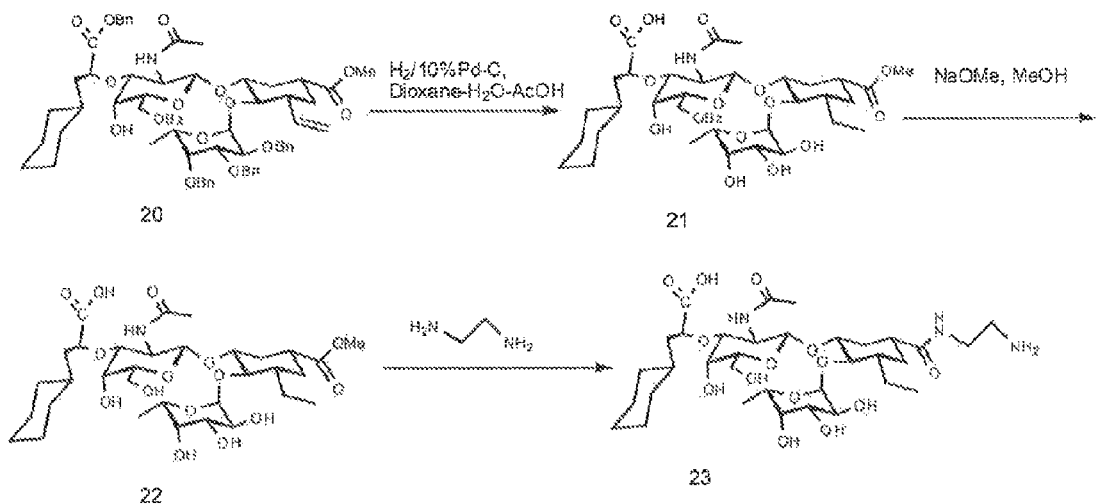
Figure 1D:
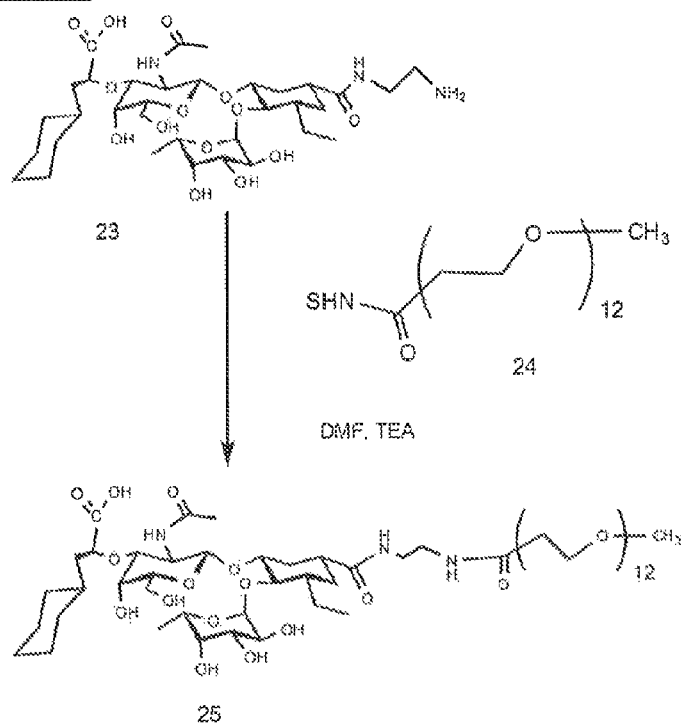

Provided herein is a method for mobilizing cells from the bone marrow, including hematopoietic cells, such as hematopoietic stem cells and hematopoietic progenitor cells and leukocytes (e.g., granulocytes (including neutrophils), macrophages, etc.). The methods for mobilizing cells described herein are also useful for mobilizing tumor cells (e.g., hematopoietic tumor cells, malignant cells) from the bone marrow. These methods include administering agents that are E-selectin antagonists, including glycomimetic compounds described herein, that inhibit interaction of E-selectin with sialyl Le$^a$ (sLe$^a$) or sialyl Le$^x$ (sLe$^x$). Agents that are also provided are antibodies, polypeptides, peptides and aptamers that bind at or near the binding site on E-selectin to which the compounds bind (i.e., an antibody, polypeptide, peptide, or aptamer as described herein is capable of competing with the compounds to inhibit E-selectin interaction with sialyl Le$^a$ (sLe$^a$) or sialyl Le$^x$ (sLe$^x$)).

E-selectin is an adhesion molecule expressed on endothelial cells and binds to specific carbohydrate sequences (sialyl Le$^x$ and sialyl Le$^a$) found on the surfaces of opposing bound cells. The endothelium in most of the normal vasculature does not express E-selectin until stimulation of protein synthesis by inflammatory mediators. After about three hours of de novo protein synthesis, E-selectin is then expressed as a result of an inflammatory response. In contrast, E-selectin is constitutively expressed in the bone marrow by the endothelial cells lining the blood vessels. Here, it is thought, without wishing to be bound by theory, that hematopoietic stem and progenitor cells reside in the vasculature niche of the bone marrow by binding to adhesion molecules, including E-selectin. Recent evidence also suggests that E-selectin plays a role in activating these cells, causing cell proliferation and initiating differentiation.

In this disclosure, antagonists of E-selectin are provided that mobilize cells, including hematopoietic cells, from the bone marrow. Such antagonists may include but are not limited to small molecules, antibodies, aptamers, peptides, and glycoproteins. Stem cells derived from mobilized cells from the bone marrow of each of autologous and allogeneic donors have a wide range of therapeutic uses. Due to age, disease, and certain genetic conditions, some individuals do not respond well to current methods of mobilizing stem cells, such as the use of Plerixafor (AMD-3100) and/or G-CSF. In one embodiment, a method is provided for mobilizing stem cells by inhibiting E-selectin, a major adhesion protein in the bone marrow vasculature. This method may comprise using the E-selectin antagonist alone or in combination with other agents currently used to mobilize hematopoietic stem cells. Specific small molecule antagonists of E-selectin that mobilize hematopoietic cells and which are therefore useful for these methods and other methods are described herein.

Agents

E-selectin antagonists (e.g., compounds of formula I) described herein comprise substituents that are less likely to be cleaved by esterases and thus have increased stability. These compounds therefore provide improved compounds than those previously described in the art.

In one embodiment, the E-selectin antagonist is a glycomimetic compound that has the following formula (I):

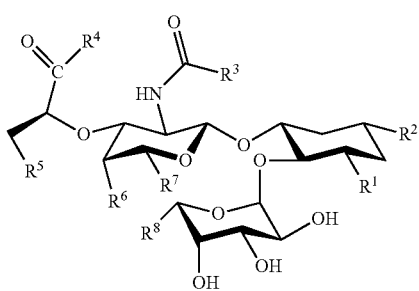

(I)

a pharmaceutically acceptable salt (i.e., physiologically suitable salt), isomer, tautomer, hydrate or solvate thereof. Formula I comprises $R^1$ to $R^8$ that represent positions on the compound at which a substituent (e.g., $R^8$) or a portion of a substituent (e.g., $R^3$) may be varied according to the choices provided herein.

In one embodiment, $R^1$ is $C_1$-$C_8$ alkyl, $C_2$-$C_8$ alkenyl, $C_2$-$C_8$ alkynyl, $C_1$-$C_8$ haloalkyl, $C_2$-$C_8$ haloalkenyl or $C_2$-$C_8$ haloalkynyl;

$R^2$ is H, $C_1$-$C_8$ alkyl, —C(=O)NH(CH$_2$)$_{1-4}$NH$_2$, —C(=O)OY where Y is $C_1$-$C_4$ alkyl or $C_2$-$C_4$ alkenyl or $C_2$-$C_4$ alkynyl, a non-glycomimetic moiety, or a linker-non-glycomimetic moiety (i.e., a linker joined to a non-glycomimetic moiety), wherein the non-glycomimetic moiety is selected from polyethylene glycol, thiazolyl, and chromenyl;

$R^3$ is $C_1$-$C_8$ alkyl, $C_2$-$C_8$ alkenyl, $C_2$-$C_8$ alkynyl, $C_1$-$C_8$ haloalkyl, $C_2$-$C_8$ haloalkenyl, $C_2$-$C_8$ haloalkynyl or cyclopropyl;

$R^4$ is —OH or —NZ$^1$Z$^2$ where Z$^1$ and Z$^2$ are each independently H, $C_1$-$C_8$ alkyl, $C_2$-$C_8$ alkenyl, $C_2$-$C_8$ alkynyl, $C_1$-$C_8$ haloalkyl, $C_2$-$C_8$ haloalkenyl or $C_2$-$C_8$ haloalkynyl or wherein Z$^1$ and Z$^2$ join to form a ring;

$R^5$ is $C_3$-$C_8$ cycloalkyl;

$R^6$ is —OH, $C_1$-$C_8$ alkyl, $C_2$-$C_8$ alkenyl, $C_2$-$C_8$ alkynyl, $C_1$-$C_8$ haloalkyl, $C_2$-$C_8$ haloalkenyl or $C_2$-$C_8$ haloalkynyl;

$R^7$ is —CH$_2$OH, $C_1$-$C_8$ alkyl, $C_2$-$C_8$ alkenyl, $C_2$-$C_8$ alkynyl, $C_1$-$C_8$ haloalkyl, $C_2$-$C_8$ haloalkenyl or $C_2$-$C_8$ haloalkynyl; and $R^8$ is $C_1$-$C_8$ alkyl, $C_2$-$C_8$ alkenyl, $C_2$-$C_8$ alkynyl, $C_1$-$C_8$ haloalkyl, $C_2$-$C_8$ haloalkenyl or $C_2$-$C_8$ haloalkynyl.

In some embodiments, the compound of formula (I) is selected from compounds wherein (a) at least one of $R^1$, $R^3$, $R^6$, $R^7$ and $R^8$ is $C_1$-$C_8$ haloalkyl; (b) at least one of $R^3$, $R^6$, $R^7$ and $R^8$ is $C_1$-$C_8$ haloalkyl; (c) at least two of $R^1$, $R^3$, $R^6$, $R^7$ and $R^8$ are $C_1$-$C_8$ haloalkyl; (d) $R^2$ is a linker-non-glycomimetic moiety; or (e) at least one of $R^1$, $R^3$, $R^6$, $R^7$ and $R^8$ is $C_1$-$C_8$ haloalkyl, and $R^2$ is a linker-non-glycomimetic moiety.

In a particular embodiment of the compound of formula I, $C_1$-$C_8$ haloalkyl is selected from —CH$_2$X, —CH$_2$—(CH$_2$)$_m$—CH$_2$X, —CHX$_2$, —CH$_2$—(CH$_2$)$_m$—CHX$_2$, —CX$_3$ and —CH$_2$—(CH$_2$)$_m$—CX$_3$, wherein m is 0-6 and X is F, Cl, Br or I. In this embodiment, the terminal carbon is substituted with one or more halo radicals. In specific embodiments, X is F. When two or more halo radicals are present, each is independently selected. The number of methylene groups represented by "m" is "0-6" which includes 0, 1, 2, 3, 4, 5, 6 and all ranges between and including 0 to 6. In certain embodiments, at least one of $C_1$-$C_8$ haloalkyl is CH$_2$X, —CHX$_2$, or —CX$_3$. In certain more specific embodiments, X is F.

In one embodiment of the compound of formula (I), $R^1$ is $C_1$-$C_8$ alkyl, $C_2$-$C_8$ alkenyl, $C_2$-$C_8$ alkynyl, $C_1$-$C_8$ haloalkyl, $C_2$-$C_8$ haloalkenyl or $C_2$-$C_8$ haloalkynyl. In certain embodiments of the compound of formula I, $R^1$ is $C_1$-$C_8$ alkyl or $C_1$-$C_8$ haloalkyl. In more particular embodiments, $R^1$ is $C_1$-$C_3$ alkyl or $C_1$-$C_3$ haloalkyl. In a more specific embodiment, $R^1$ is methyl (—CH$_3$), ethyl (—CH$_2$CH$_3$), or —CF$_3$ or —CHF$_2$. In another embodiment, $R^1$ is ethyl (—CH$_2$CH$_3$) or —CHF$_2$ In one embodiment of the compound of formula (I), $R^2$ is H, $C_1$-$C_8$ alkyl, —C(=O)NH(CH$_2$)$_{1-4}$NH$_2$, or —C(=O)OY wherein Y is $C_1$-$C_4$ alkyl, $C_2$-$C_4$ alkenyl or $C_2$-$C_4$ alkynyl. In other embodiments, $R^2$ is a non-glycomimetic moiety (M) or a linker (L)-non-glycomimetic moiety, wherein the non-glycomimetic moiety is selected from polyethylene glycol (PEG), thiazolyl, and chromenyl. In one particular embodiment, $R^2$ is a non-glycomimetic moiety (M), linker (L)-non-glycomimetic moiety (also indicated as -L-non-glycomimetic moiety or -L-M), wherein the non-glycomimetic moiety is polyethylene glycol. In a particular embodiment, $R^2$ is —C(=O)NH(CH$_2$)$_2$NH$_2$. In certain embodiments, when $R^2$ comprises a non-glycomimetic moiety or a linker-non-glycomimetic moiety described herein, wherein these moieties provide advantageous or improved characteristics such as enhanced bioavailability; desired pharmacokinetics; improved stability, and the like, to the compound and are non-immunogenic. Other exemplary non-glycomimetic moieties described herein include thiazolyl and chromenyl heteroaryls, for example 4-methylthiazolyl and 7-hydroxy-2H-chromen-2-on-yl. In some embodiments, $R^2$ is H.

$R^2$ may be attached to the glycomimetic portion of the compounds of formula (I) (or formula Ia as described below) either directly or via a linker (L). Linkers are well known to a person of ordinary skill in the art. In particular embodiments, the linker that joins the glycomimetic moiety of formula I to a non-glycomimetic moiety (M) is —C(=O) NH(CH$_2$)$_{1-4}$NHC(=O)—; in more specific embodiments, the linker is —C(=O)NH(CH$_2$)NHC(=O)—, or the linker is —C(=O)NH(CH$_2$)$_2$NHC(O)—. In other certain embodiments, the linker is —C(=O)NH(CH$_2$)$_{1-4}$NHC(=O) (CH$_2$)$_{1-4}$; in more specific embodiments, the linker is —C(=O)NH(CH$_2$)NHC(=O)—CH$_2$, or the linker is —C(=O)NH(CH$_2$)$_2$NHC(=O)—(CH$_2$)$_2$. Linkers also include those called in the art "click chemistry" linkers (see, e.g., Brik et al., *Chem. Bio. Chem.* 2003, 4, 1246; Helms et al., *J. Am. Chem. Soc.* 2004, 126, 15020; Lober et al., *Org. Let.* 2003, 5, 1753; Moses et al., *Chem. Soc. Rev* 2007, 36, 1249-1262).

Other exemplary linkers are described in International Application Publication WO 2007/028050. By way of additional example, linkers include the following.

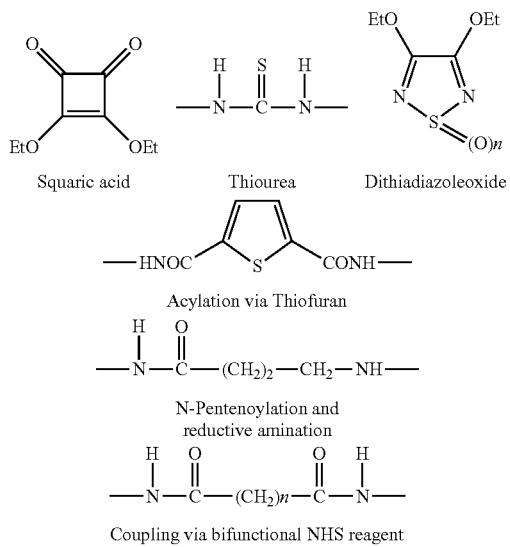

Squaric acid    Thiourea    Dithiadiazoleoxide

Acylation via Thiofuran

N-Pentenoylation and reductive amination

Coupling via bifunctional NHS reagent

In still other embodiments, the linker is

In another embodiment, the linker is —C(=O)—NH—(CH$_2$)$_2$—NH—; —CH$_2$—NH—CH$_2$—, or is —C(O)—NH—CH$_2$—.

In one embodiment of the compound of formula (I), $R^3$ is $C_1$-$C_8$ alkyl, $C_2$-$C_8$ alkenyl, $C_2$-$C_8$ alkynyl, $C_1$-$C_8$ haloalkyl, $C_2$-$C_8$ haloalkenyl, $C_2$-$C_8$ haloalkynyl or cyclopropyl. In other certain embodiments of the compound of formula I, $R^1$ is $C_1$-$C_8$ alkyl or $C_1$-$C_8$ haloalkyl or cyclopropyl. In more particular embodiments, $R^1$ is $C_1$-$C_3$ alkyl or $C_1$-$C_3$ haloalkyl. In more specific embodiments, $R^3$ is —CH$_3$ (methyl) or —CH$_2$CH$_2$—CH$_3$ (ethyl) or —CF$_3$ or —CHF$_2$. In still other embodiments, $R^3$ is methyl or trifluoromethyl.

In one embodiment of the compound of formula (I), $R^4$ is —OH, or —NZ$^1$Z$^2$, where —Z$^1$ and Z$^2$ are each independently H, $C_1$-$C_8$ alkyl, $C_2$-$C_8$ alkenyl, $C_2$-$C_8$ alkynyl, $C_1$-$C_8$ haloalkyl, $C_2$-$C_8$ haloalkenyl or $C_2$-$C_8$ haloalkynyl or wherein Z$^1$ and Z$^2$ join to form a ring. When Z$^1$ and Z$^2$ join to form a ring, the ring is a heterocyclic ring wherein the heteroatom is N. In one specific embodiment, $R^4$ is —OH or —NZ$^1$Z$^2$ wherein Z$^1$ and Z$^2$ are each H or $C_1$-$C_8$ alkyl. In a more specific embodiment, Z$^1$ and Z$^2$ are each —CH$_3$ and —NZ$^1$Z$^2$ is —N(CH$_3$)$_2$.

In one embodiment of the compound of formula (I), $R^5$ is $C_3$-$C_8$ cycloalkyl (i.e., cyclopropyl, cyclobutyl, cyclopentyl, cyclohexyl, cycloheptyl or cyclooctyl). In another embodiment, $R^5$ is $C_3$-$C_6$ cycloalkyl (i.e., cyclopropyl, cyclobutyl, cyclopentyl or cyclohexyl). In a particular embodiment of the compound of formula I, $R^5$ is cyclohexyl.

In one embodiment of the compound of formula (I), $R^6$ is —OH, $C_1$-$C_8$ alkyl, $C_2$-$C_8$ alkenyl, $C_2$-$C_8$ alkynyl, $C_1$-$C_8$ haloalkyl, $C_2$-$C_8$ haloalkenyl or $C_2$-$C_8$ haloalkynyl. In other particular embodiments of the compound of formula I, $R^6$ is —OH.

In one embodiment of the compound of formula (I), $R^7$ is —CH$_2$OH, $C_1$-$C_8$ alkyl, $C_2$-$C_8$ alkenyl, $C_2$-$C_8$ alkynyl, $C_1$-$C_8$ haloalkyl, $C_2$-$C_8$ haloalkenyl or $C_2$-$C_8$ haloalkynyl. In yet another specific embodiment of the compound of formula I, $R^7$ is —CH$_2$OH, $C_1$-$C_8$ alkyl, or $C_1$-$C_8$ haloalkyl. In more particular embodiments, $R^7$ is —CH$_2$OH or —CH$_3$. In another specific embodiment, $R^7$ is $C_1$-$C_3$ haloalkyl. In a more specific embodiment, $R^7$ is —CH$_2$F, —CHF$_2$ or —CF$_3$. In another specific embodiment, $R^7$ is —CH$_2$OH or —CHF$_2$.

In one embodiment of the compound of formula (I), $R^8$ is $C_1$-$C_8$ alkyl, $C_2$-$C_8$ alkenyl, $C_2$-$C_8$ alkynyl, $C_1$-$C_8$ haloalkyl, $C_2$-$C_8$ haloalkenyl or $C_2$-$C_8$ haloalkynyl. In another particular embodiment of the compound of formula I, $R^1$ is $C_1$-$C_8$ alkyl or $C_1$-$C_8$ haloalkyl. In more particular embodiments, $R^8$ is $C_1$-$C_3$ alkyl or $C_1$-$C_3$ haloalkyl. In a more particular embodiment, $R^8$ is methyl (—CH$_3$), —CH$_2$F, —CHF$_2$ or

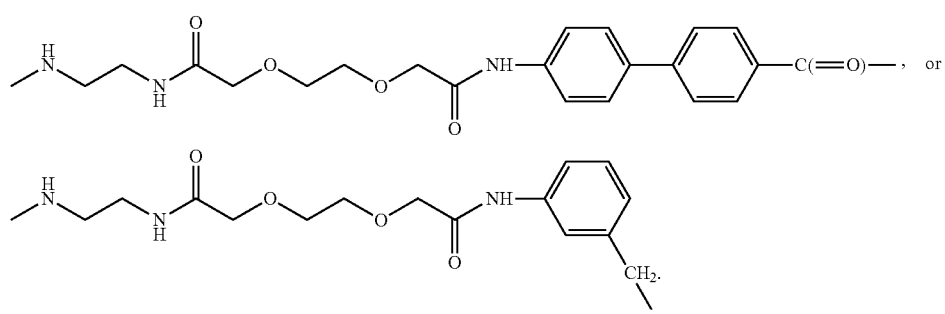

trifluoromethyl (—CF$_3$). In another particular embodiment, R$^8$ is methyl or trifluoromethyl (—CF$_3$).

In a particular embodiment of the compound of formula I, at least one or at least two of R$^1$, R$^3$, R$^6$, R$^7$ and R$^1$ is C$_1$-C$_8$ haloalkyl. In other certain embodiments, at least one of R$^3$, R$^6$, R$^7$ and R$^1$ is C$_1$-C$_8$ haloalkyl. In other particular embodiments, R$^2$ is a linker (L)-non-glycomimetic moiety (M) as defined herein; in still other particular embodiments, R$^2$ is a linker (L)-non-glycomimetic moiety (M) and at least one of R$^1$, R$^3$, R$^6$, R$^7$ and R$^8$ is C$_1$-C$_8$ haloalkyl. When two or more of R$^1$, R$^3$, R$^6$, R$^7$ and R$^8$ are C$_1$-C$_8$ haloalkyl, the haloalkyls are independently selected, i.e., may be the same or different or both (if at least three present). Oral bioavailability of a compound may be improved and/or the half-life of the compound increased when at least one or more of R$^1$, R$^3$, R$^6$, R$^7$ and R$^8$ is C$_1$-C$_8$ haloalkyl and when R$^2$ comprises a non-glycomimetic moiety (M) or linker (L)-non-glycomimetic moiety (-L-M).

In another embodiment of the compound of formula (I) provided herein, R$^8$ is cyclohexyl and R$^6$ is —OH and the compound of formula (I) has the following formula (Ia):

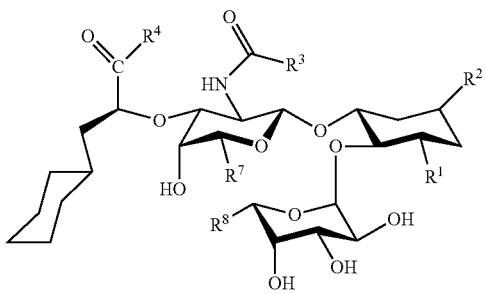

or a pharmaceutically acceptable salt (i.e., physiologically suitable salt), isomer, tautomer, hydrate or solvate thereof, wherein R$^1$ is C$_1$-C$_8$ alkyl or C$_1$-C$_8$ haloalkyl;

R$^2$ is H, C$_1$-C$_8$ alkyl, —C(=O)NH(CH$_2$)$_{1-4}$NH$_2$, —C(=O)OY where Y is C$_1$-C$_4$ alkyl, a non-glycomimetic moiety or a linker-non-glycomimetic moiety wherein the non-glycomimetic moiety is selected from polyethylene glycol, thiazolyl, and chromenyl;

R$^3$ is C$_1$-C$_8$ alkyl, C$_1$-C$_8$ haloalkyl, or cyclopropyl;

R$^4$ is —OH or —NZ$^1$Z$^2$ where Z$^1$ and Z$^2$ are each independently H or C$_1$-C$_8$ alkyl;

R$^7$ is —CH$_2$OH, C$_1$-C$_8$ alkyl, C$_1$-C$_8$ haloalkyl, and R$^8$ is C$_1$-C$_8$ alkyl or C$_1$-C$_8$ haloalkyl.

In certain embodiments, halo is F.

In other particular embodiments, R$^1$ is —CH$_3$, —CH$_2$CH$_3$, —CH$_2$F, —CHF$_2$, —CF$_3$, —CH$_2$CH$_2$F, —CH$_2$CHF$_2$, or —CH$_2$CF$_3$.

In other embodiments, R$^3$ is —CH$_3$, —CH$_2$F, —CHF$_2$, or —CF$_3$.

In yet another particular embodiment, R$^4$ is —OH or —N(CH$_3$)$_2$.

In certain embodiments, R$^7$ is —CH$_2$OH, —CH$_3$, —CH$_2$F, —CHF$_2$, or —CF$_3$.

In still another specific embodiment, R$^8$ is —CH$_3$, —CH$_2$F, —CHF$_2$, or —CF$_3$.

In certain particular embodiments, exemplary compounds of formula (I) are provided, wherein R$^1$ is ethyl, CF$_3$, or —CHF$_2$; R$^3$ is methyl or —CF$_3$; R$^4$ is —OH or —N(CH$_3$)$_2$; R$^5$ is cyclohexyl; R$^6$ is —OH; R$^7$ is —CH$_2$—OH, —CHF$_2$, or CF$_3$; R$^8$ is methyl, —CF$_3$, or —CHF$_2$; and R$^2$ is H, —C(=O)NH(CH$_2$)$_{1-4}$NH$_2$, a non-glycomimetic moiety (M), or linker (L)-non-glycomimetic moiety (M) as described above for a compound of formula I. In other embodiments, R$^2$ is as described above for a compound of formula I. Examples described herein have one of the following structural formulae (Id), (I), (If), (Ig), (Ih), (Ii), (Ij), or (Ik).

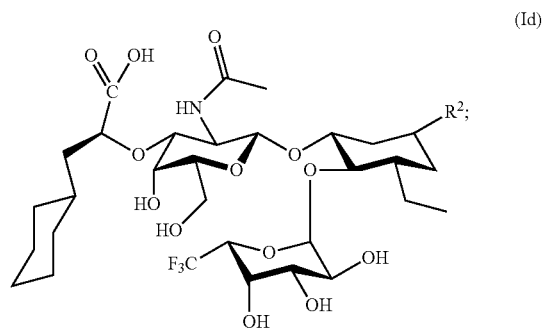

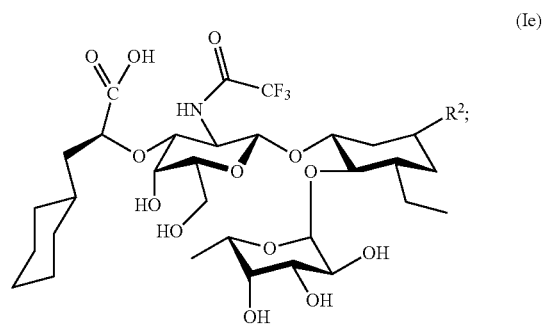

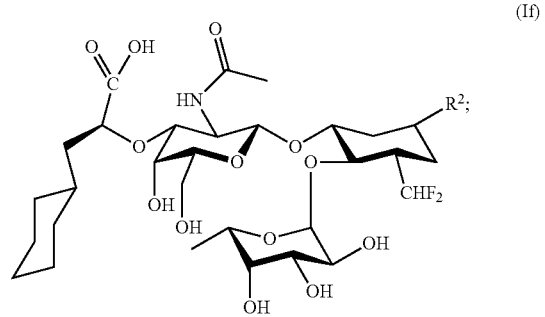

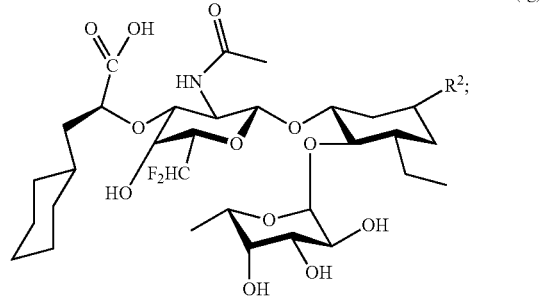

-continued
(Ih)
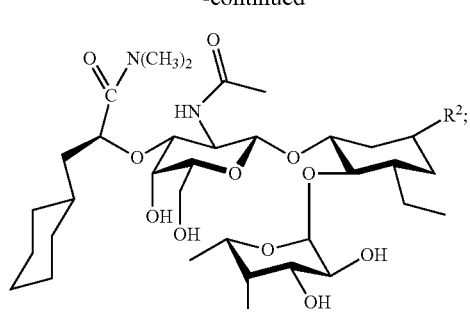
(Ii)
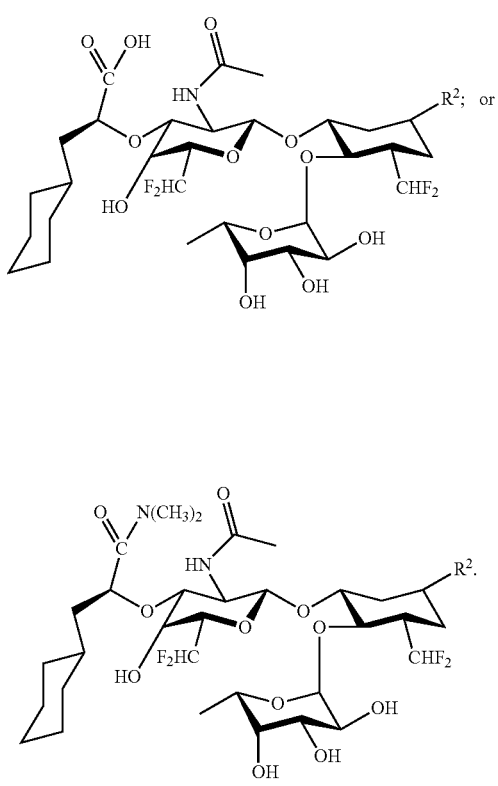
(Ij)
(Ik)
In certain particular embodiments, R₂ is H, —C(=O)NH(CH₂)NH₂, or —C(=O)OCH₃ (also depicted as —COOCH₃), and exemplary compounds have one of the following formulae.
(compound 31)
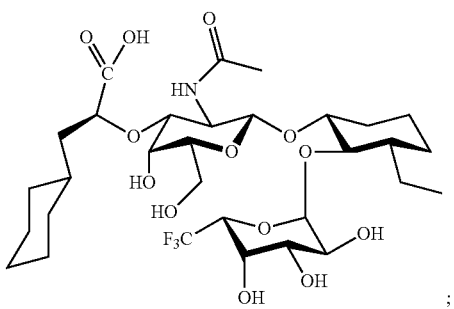
(compound 32)
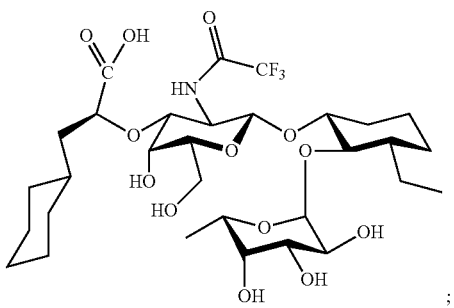
(compound 33)
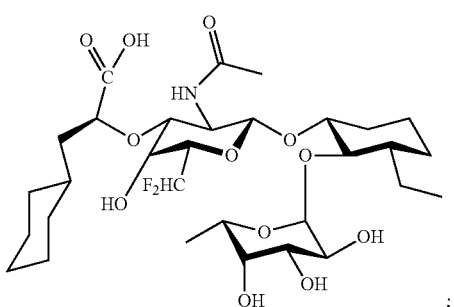
(compound 40)
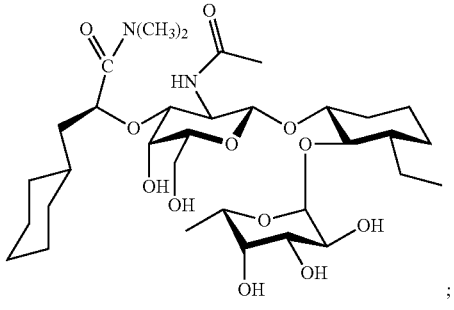

(compound 41)
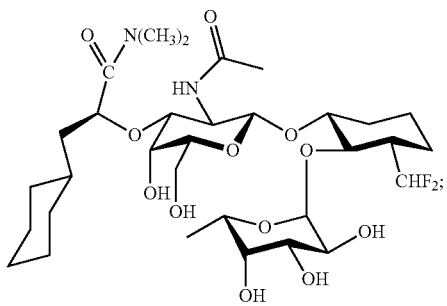

(compound 36)
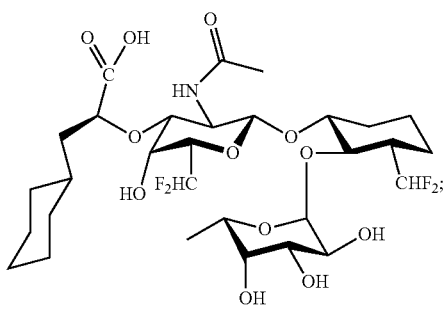

(compound 42)
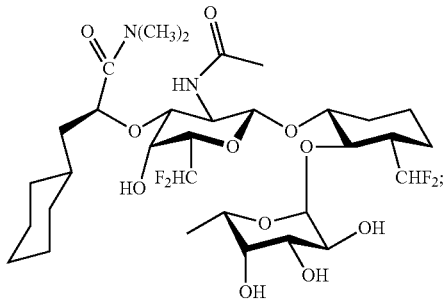

(compound 27)
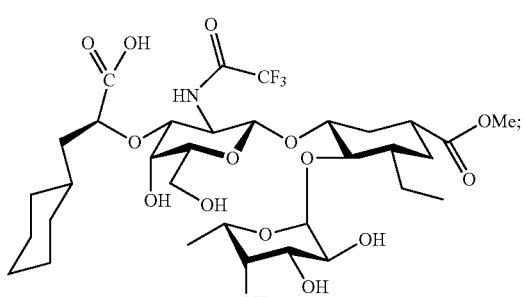

(compound 23)
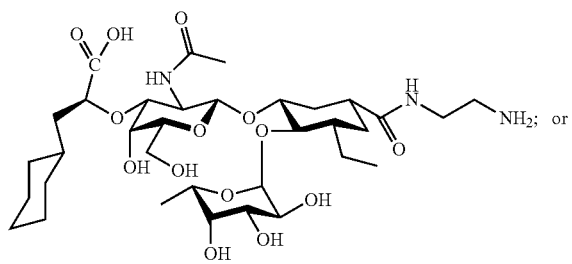

(compound 43)
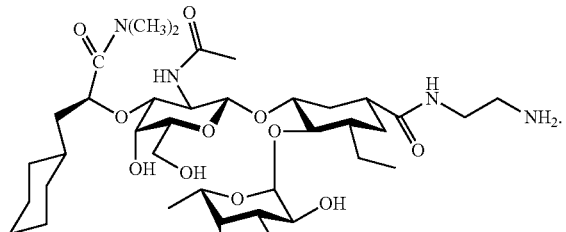

Also described herein are the following compounds of formula (I):

(compound 30)
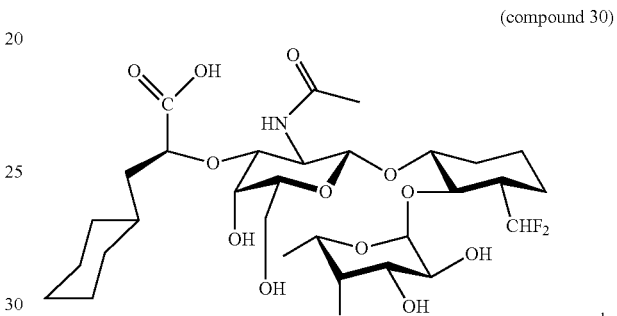

and (compound 22)
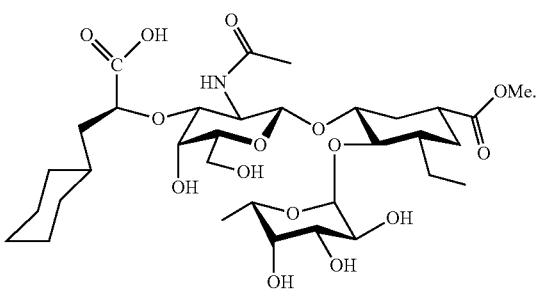

In a particular embodiment of the compound of formula I and formula Ia, $R^2$ is a non-glycomimetic moiety that is a polyethylene glycol (PEG). PEG is a polymer of repeating ethylene oxide units. Length and thus molecular weight vary depending upon how many of repeating units are present. The ethylene oxide units are abbreviated herein as

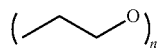

where n is an integer or a general range of integers from 1 to 100, and any smaller range within the general range. For example, the range of integers for n may be 1 to 25, 1 to 50, 2 to 15, 2 to 20, 2 to 25, 2 to 40, 2 to 50, 2 to 100, 5 to 20, 5 to 40, 5 to 100, as well as all the other numerical combinations. In particular embodiments, n is 4, 8, 12, 16, 20, 24, or 28.

In particular embodiments, PEG is the non-glycomimetic moiety (M) and the linker (L) is —C(=O)NH(CH$_2$)$_2$NHC(=O)— to provide one of the following compounds having formula (Ib) or (Ic):

(Ib)
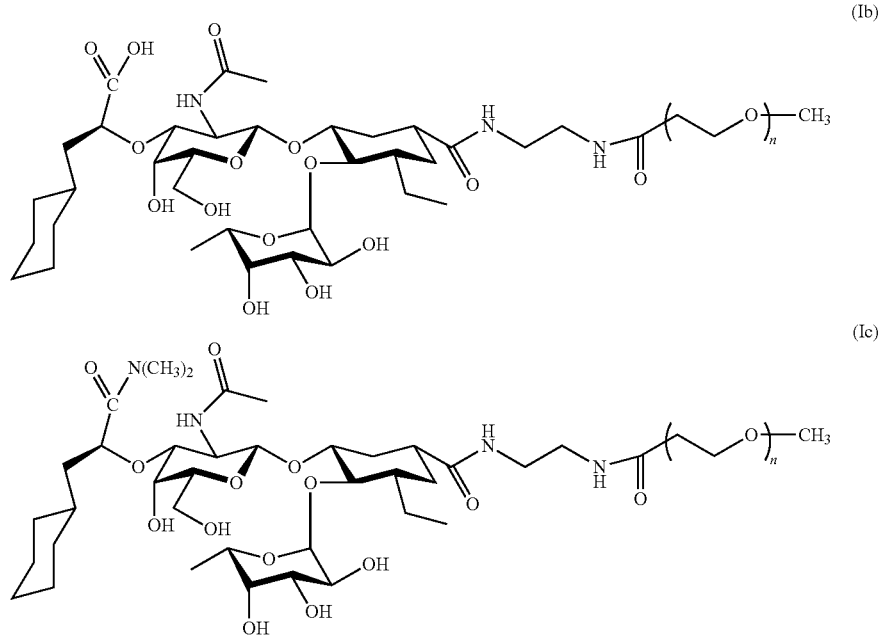
(Ic)
wherein n is 1 to 100. In particular embodiments, n is 4, 8, 12, 16, 20, 24, or 28.
In other particular embodiments when M is PEG, the compound of formula (I) has one of the formulae:
(compound 26)
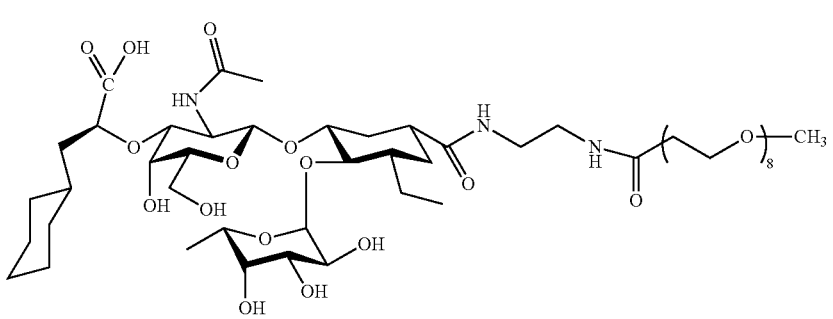
(compound 25)
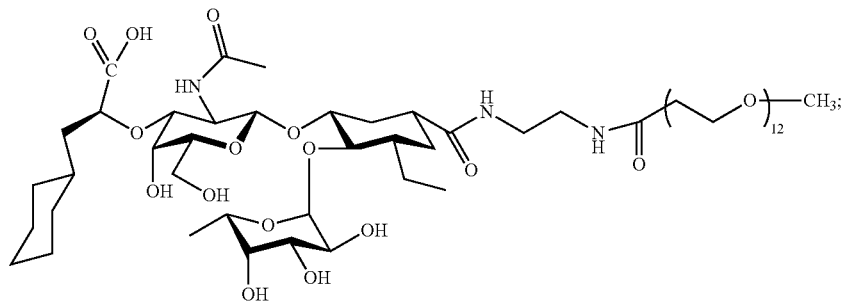

(compound 44)

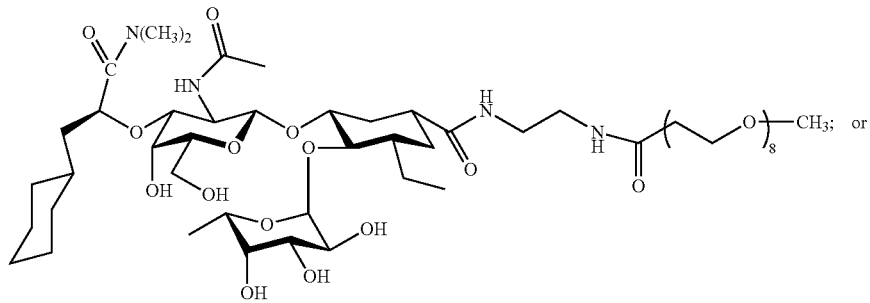

(compound 45)

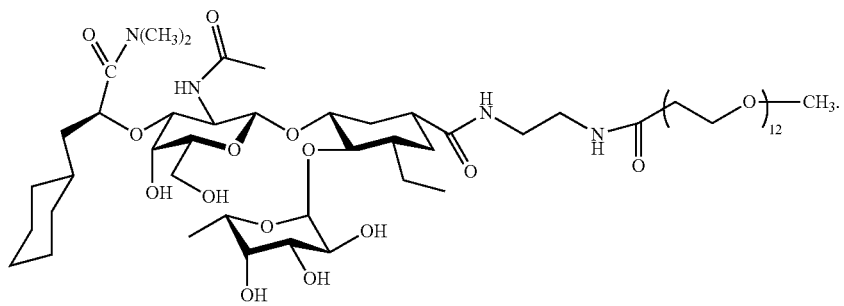

In a particular embodiment, R² is a linker-non-glycomimetic moiety (M), and the non-glycomimetic moiety is thiazolyl or chromenyl, for example, 4-methylthiazolyl or 7-hydroxy-2H-chromen-2-on-yl and the compound of formula (I) has one of the following formulae:

(compound 28)

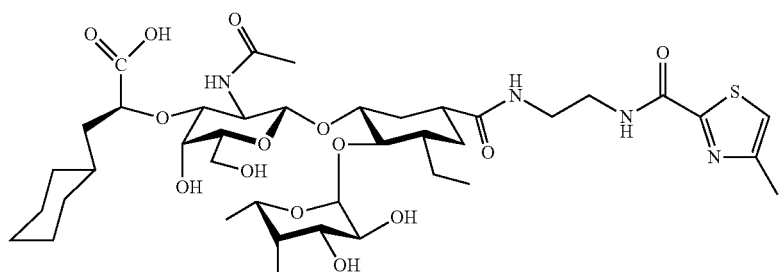

or (compound 29)

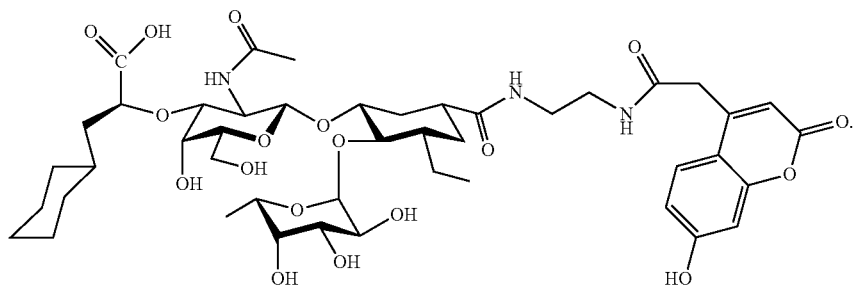

Compounds of formula I include all isomers, physiologically acceptable salts (i.e., pharmaceutically acceptable salts), hydrates, solvates, polymorphs, metabolites and prodrugs of any. Examples of isomers are stereoisomers (e.g., enantiomers and racemates) and tautomers.

Also provided herein are pharmaceutical compositions that comprise one or more of the compounds of formula (I), substructures (e.g., Formula (Ia), (Ib), (Ic), (Id), (Ie), (If), (Ig), (Ih), (Ii), and (Ik)) and specific structures thereof, and a pharmaceutically acceptable excipient. A compound of formula (I) or a pharmaceutical composition comprising the compound may be used in methods described herein. As discussed in greater detail herein, methods are provided for mobilizing cells, including hematopoietic cells (e.g., hematopoietic stem cells, hematopoietic progenitor cells) leukocytes such as neutrophils, monocytes, lymphocytes, eosinophils, and basophils, and tumor cells from the bone marrow in a subject comprising administering to the subject a compound of formula (I), substructures, and specific structures or a pharmaceutical composition comprising a pharmaceutically acceptable excipient and any one or more of these compounds having the structure of formula I.

Definitions

The terms below, as used herein, have the following meanings, unless indicated otherwise. Certain chemical groups named herein are preceded by a shorthand notation indicating the total number of carbon atoms that are to be found in the indicated chemical group.

As used herein, a "$C_1$-$C_8$ alkyl," "$C_1$-$C_6$ alkyl," "$C_1$-$C_4$ alkyl" or "$C_1$-$C_3$ alkyl," refers to an alkane substituent with one to eight, one to six, one to four, or one to three carbon atoms, respectively, and may be straight chain, branched, or cyclic (e.g., cycloalkanyl). The term "alkanyl" may also be used herein and has the same meaning as alkyl. Examples of alkyls include methyl ("Me"), ethyl, propyl, isopropyl, butyl and t-butyl. A "$C_1$-$C_8$ haloalkyl" refers to a $C_1$-$C_8$ alkanyl substituted with at least one halogen (halo). When more than one halogen is present, the halogens present may be the same or different or both (if at least three present). A "$C_2$-$C_8$ alkenyl" or "$C_1$-$C_4$ alkenyl" refers to an alkene substituent with two to eight carbon atoms or two to four carbon atoms, respectively, at least one carbon-carbon double bond, and may be straight chain, branched or cyclic (cycloalkenyl). Examples are similar to "$C_1$-$C_8$ alkyl" examples except the alkenyl has at least one carbon-carbon double bond. A "$C_2$-$C_8$ haloalkenyl" refers to a $C_2$-$C_8$ alkenyl substituted with at least one halogen (halo). When more than one halogen is present, the halogens present may be the same or different or both (if at least three present). A "$C_2$-$C_8$ alkynyl" or "$C_2$-$C_4$ alkynyl" refers to an alkyne substituent with two to eight carbon atoms or two to four carbon atoms, respectively, at least one carbon-carbon triple bond, and may be straight chain, branched, or cyclic (e.g., cycloalkynyl). Examples are similar to "$C_1$-$C_8$ alkyl" examples except the alkynyl has at least one carbon-carbon triple bond. A "$C_2$-$C_8$ haloalkynyl" refers to a "$C_2$-$C_8$ alkynyl" substituted with at least one halogen (halo). When more than one halogen is present, the halogens present may be the same or different or both (if at least three present).

A non-glycomimetic moiety (M) is a moiety that confers one or more advantageous properties on the compound that enhance the compound's efficacy and use in vivo. Examples of such a property include increased water solubility, decreased immunogenicity, improved stability, and improved pharmacokinetic profile. An improved pharmacokinetic profile includes increased serum half-life, reduced clearance and such that improve the therapeutic index.

"Halo" (or "halogen" or "halide") is fluoro (F), chloro (Cl), bromo (Br), or iodo (I) radical.

"Aryl" refers to a radical derived from a hydrocarbon ring system comprising hydrogen, 6 to 30 carbon atoms and at least one aromatic ring. The aryl radical may be a monocyclic, bicyclic, tricyclic or tetracyclic ring system, which may include fused or bridged ring systems. Aryl radicals include, but are not limited to, aryl radicals derived from the hydrocarbon ring systems of aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, the term "aryl" or the prefix "ar-" (such as in "aralkyl") is meant to include aryl radicals that are optionally substituted.

"Aralkyl" refers to a radical of the formula —$R_b$—$R_c$ where $R_b$ is an alkylene chain as defined above and $R_c$ is one or more aryl radicals as defined above, for example, benzyl, diphenylmethyl, trityl and the like. Unless stated otherwise specifically in the specification, an aralkyl group may be optionally substituted.

"Heterocyclyl", "heterocycle" or "heterocyclic ring" refers to a stable 3- to 24-membered non-aromatic ring radical comprising 2 to 23 carbon atoms and from one to 8 heteroatoms selected from the group consisting of nitrogen, oxygen, and sulfur. In certain embodiments, the heterocyclyl radical is a 5-10 membered heterocycle that comprises 3-9 carbon atoms and from 1-3 heteroatoms. Unless stated otherwise specifically in the specification, the heterocyclyl radical may be a monocyclic, bicyclic, tricyclic or tetracyclic ring system, which may include fused or bridged ring systems; nitrogen, carbon or sulfur atom(s) in the heterocyclyl radical may be optionally oxidized; the nitrogen atom may be optionally quaternized; and the heterocyclyl radical may be partially or fully saturated. Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, I-oxo-thiomorpholinyl, 1,1-dioxo-thiomorpholinyl, 12-crown-4, 15-crown-5, 18-crown-6, 21-crown-7, aza-18-crown-6, diaza-18-crown-6, aza-21-crown-7, and diaza-21-crown-7. Unless stated otherwise specifically in the specification, a heterocyclyl group may be optionally substituted.

"Heterocyclylalkyl" refers to a radical of the formula —$R_b$—$R_c$ where $R_b$ is an alkylene chain as defined above and $R_c$ is one or more heterocyclyl radicals as defined above, for example, tetrahydrofuranyl-methyl, tetrahydropyranyl-methyl and the like. A 6-membered heterocyclylalkyl refers to a heterocyclylalkyl, wherein the heterocyclyl moiety has 6 atoms in the ring. Unless stated otherwise specifically in the specification, a heterocyclalkyl group may be optionally substituted.

"Heteroaryl" refers to a 5- to 14-membered ring system radical comprising hydrogen atoms, one to thirteen carbon atoms, one to six heteroatoms selected from the group consisting of nitrogen, oxygen, and sulfur, and at least one aromatic ring. In certain embodiments, the heteroaryl radical is a 5-10 membered heteroaryl that comprises 3-9 carbon atoms and from 1-3 heteroatoms. For purposes of this invention, the heteroaryl radical may be a monocyclic, bicyclic, tricyclic or tetracyclic ring system, which may include fused or bridged ring systems; and the nitrogen, carbon or sulfur atoms in the heteroaryl radical may be optionally oxidized; the nitrogen atom may be optionally quaternized. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e., thienyl). Unless stated otherwise specifically in the specification, a heteroaryl group may be optionally substituted.

"Heteroarylalkyl" refers to a radical of the formula —$R_b$—$R_c$ where $R_b$ is an alkylene chain as defined above and $R_c$ is one or more heteroaryl radicals as defined above, for example, furanyl-methyl, pyridyl-methyl and the like. A 6-membered heteroarylalkyl refers to a heteroarylalkyl, wherein the heteroaryl moiety has 6 atoms in the ring. Unless stated otherwise specifically in the specification, a heteroarylalkyl group may be optionally substituted.

The compounds described herein may generally be used as the free acid or free base. Alternatively, the compounds may be used in the form of acid or base addition salts. Acid addition salts of the free base amino compounds may be prepared according to methods well known in the art, and may be formed from organic and inorganic acids. Suitable organic acids include (but are not limited to) maleic, fumaric, benzoic, ascorbic, succinic, methanesulfonic, acetic, oxalic, propionic, tartaric, salicylic, citric, gluconic, lactic, mandelic, cinnamic, aspartic, stearic, palmitic, glycolic, glutamic, and benzenesulfonic acids. Suitable inorganic acids include (but are not limited to) hydrochloric, hydrobromic, sulfuric, phosphoric, and nitric acids. Base addition salts of the free acid compounds of the compounds described herein may also be prepared by methods well known in the art, and may be formed from organic and inorganic bases. Suitable inorganic bases included (but are not limited to) the hydroxide or other salt of sodium, potassium, lithium, ammonium, calcium, magnesium, iron, zinc, copper, manganese, aluminum, and the like, and organic bases such as substituted ammonium salts. Thus, the term "pharmaceutically acceptable salt" (or physiologically suitable salt) of compounds of formula I and substructures thereof, as well as any and all substructures and specific compounds described herein is intended to encompass any and all pharmaceutically suitable salt forms.

Compounds of formula I and substructures thereof and specific structures may sometimes be depicted as an anionic species. One of ordinary skill in the art will recognize that the compounds exist with an equimolar ratio of cation. For instance, the compounds described herein can exist in the fully protonated form, or in the form of a salt such as sodium, potassium, ammonium or in combination with any inorganic base as described above. When more than one anionic species is depicted, each anionic species may independently exist as either the protonated species or as the salt species. In some specific embodiments, the compounds described herein exist as the sodium salt.

Furthermore, some of the crystalline forms of any compound described herein may exist as polymorphs, which are also included and contemplated by the present disclosure. In addition, some of the compounds may form solvates with water or other solvents. Such solvates are similarly included within the scope of compounds and compositions described herein.

With regard to stereoisomers, the compounds of formula I as well as any substructure or specific structure described herein, may have one or more chiral (or asymmetric) centers, and may thus give rise to enantiomers, diastereomers, and other stereoisomeric forms that may be defined, in terms of absolute stereochemistry, as (R)- or (S)-. When the compounds described herein contain olefinic double bonds or other centers of geometric asymmetry, and unless specified otherwise, it is intended that the compounds include both E and Z geometric isomers (e.g., cis or trans). Likewise, unless otherwise specified, all possible isomers, as well as their racemic and optically pure forms, and all tautomeric forms are also intended to be included. It is therefore contemplated that various stereoisomers and mixtures thereof include "enantiomers," which refers to two stereoisomers whose molecules are nonsuperimposeable mirror images of one another. Thus, the compounds may occur in any isomeric form, including racemates, racemic mixtures, and as individual enantiomers or diastereomers. A tautomer refers to a proton shift from one atom of a molecule to another atom of the same molecule.

"Prodrug" is meant to indicate a compound that may be converted under physiological conditions or by solvolysis to a biologically active compound described herein. Thus, the term "prodrug" refers to a metabolic precursor of a compound described herein that is pharmaceutically acceptable. A prodrug may be inactive when administered to a subject in need thereof, but is converted in vive to an active compound as described herein. Prodrugs are typically rapidly transformed in vive to yield the parent compound described herein, for example, by hydrolysis in blood. The prodrug compound often offers advantages of solubility, tissue compatibility or delayed release in a mammalian organism (see, e.g., Bundgard, H., Design of Prodrugs (1985), pp. 7-9, 21-24 (Elsevier, Amsterdam). A discussion of prodrugs is provided in Higuchi, T., et al., "Pro-drugs as Novel Delivery Systems," A.C.S. Symposium Series, Vol. 14, and in Bioreversible Carriers in Drug Design, ed. Edward B. Roche, American Pharmaceutical Association and Pergamon Press, 1987, both of which are incorporated in full by reference herein.

The term "prodrug" is also meant to include any covalently bonded carriers which release the active compound as described herein in vive when such prodrug is administered to a mammalian subject. Prodrugs of a compound described herein may be prepared by modifying functional groups present in the compound described herein in such a way that the modifications are cleaved, either in routine manipulation or in vivo, to the parent compound described herein. Prodrugs include compounds described herein wherein a hydroxy, amino or mercapto group is bonded to any group that, when the prodrug of the compound is administered to a mammalian subject, cleaves to form a free hydroxy, free amino or free mercapto group, respectively. Examples of prodrugs include, but are not limited to, ester and amide derivatives of hydroxy, carboxy, mercapto or amino functional groups in the compounds described herein and the like.

Compound Synthesis Procedures

Figure 2:
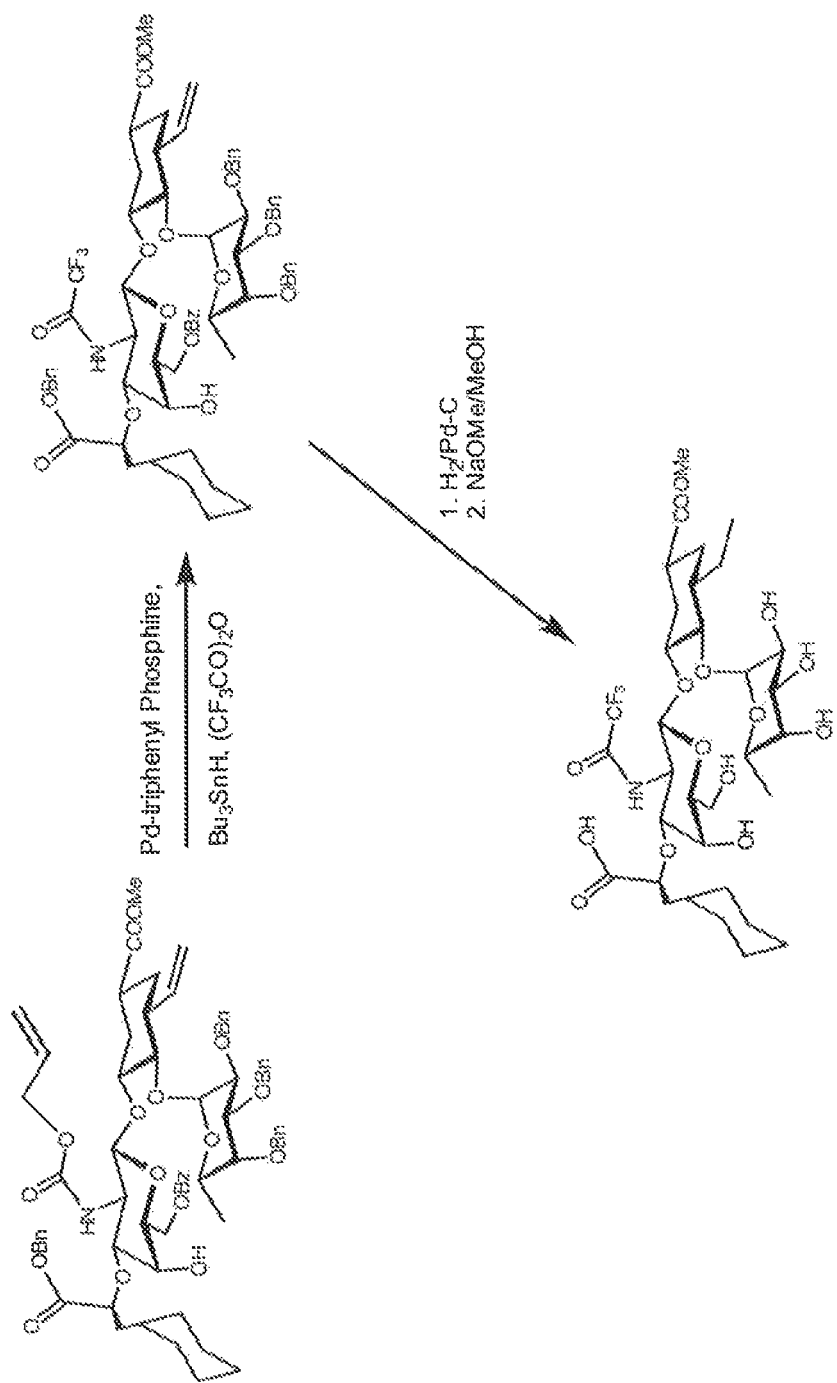
FIG. 2 is a diagram illustrating the synthesis of an embodiment of the compounds having formula I provided herein.
Figure 3A:
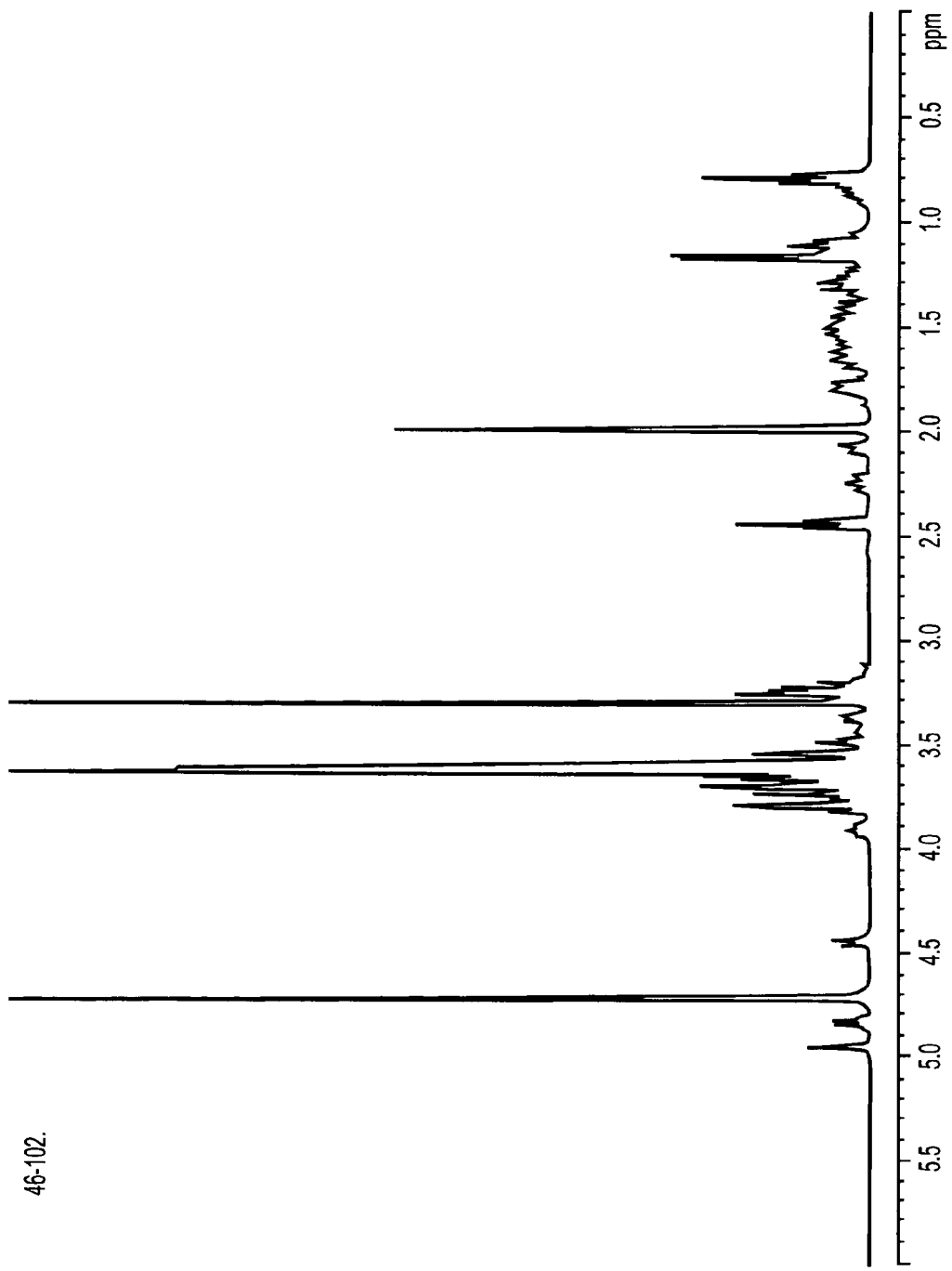
FIGS. 3A-3D present a scan of the NMR spectrum of Compound 25.
Figure 3B:
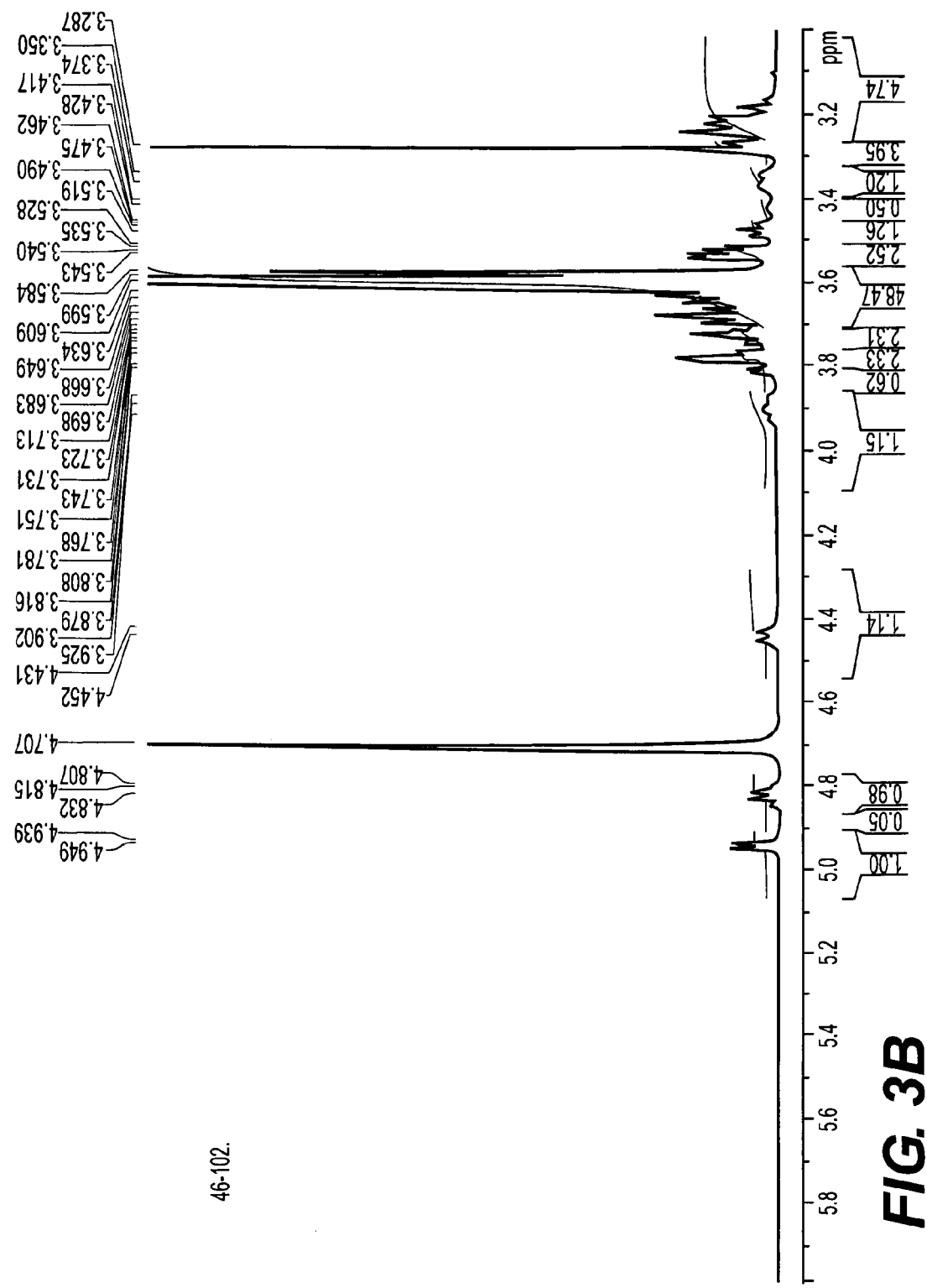
Figure 3C:
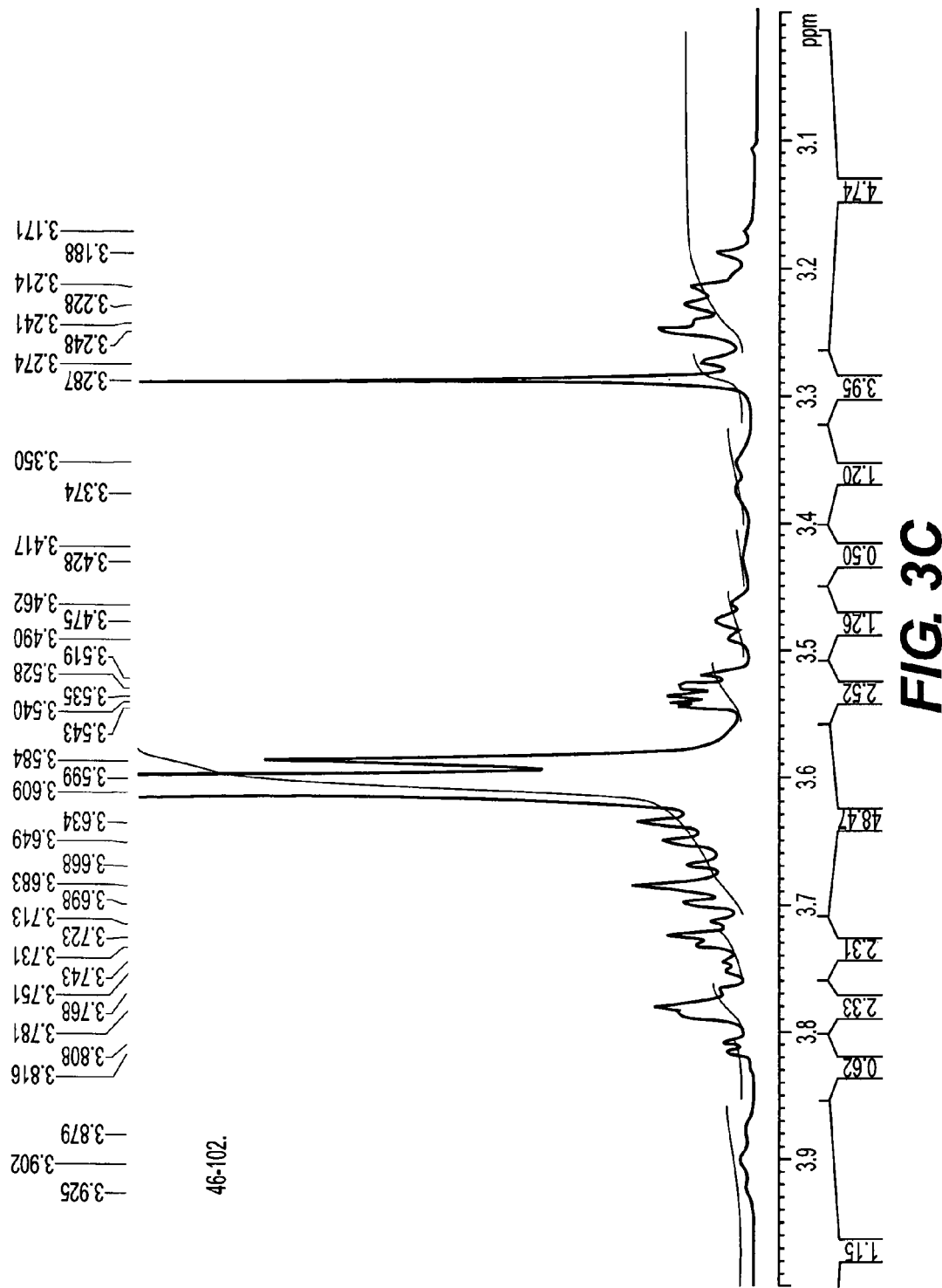
Figure 3D:
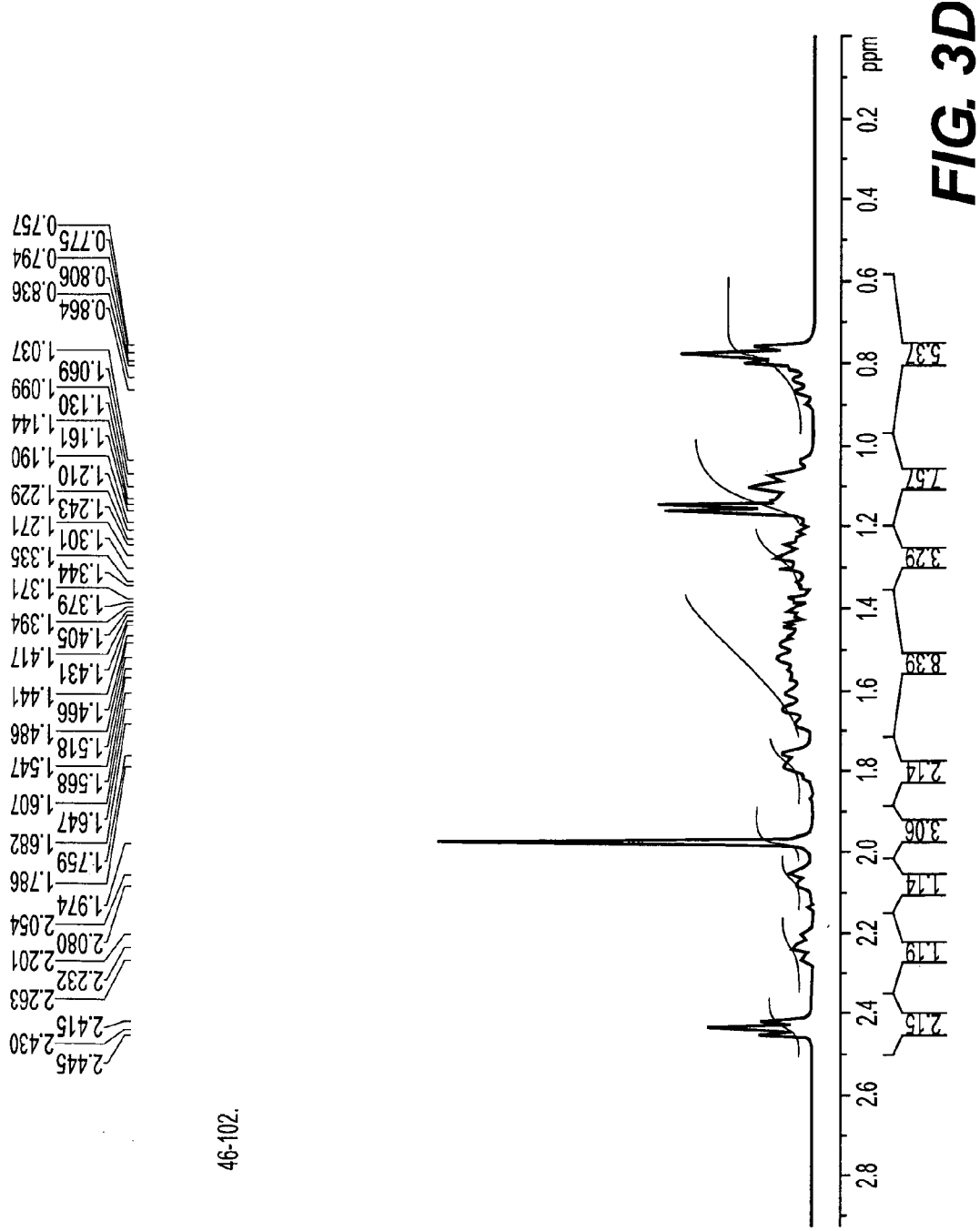

Synthesis of the compounds of formula I (and substructures, and specific compounds) may be performed as described herein, including the Examples, using techniques familiar to a person skilled in the art. Synthetic methods for preparing exemplary compounds described herein are described in Example 1. The methods may be used for synthesis of the compounds of formula I by using appropriate reactants for preparation of the specific compound using the techniques and methods described herein, and that are routinely practiced in the art. By way of further example, FIGS. 1 and 2 provide schematics of synthesis schemes for exemplary compounds described herein.

In general, compounds of formula (I) can be prepared according to the following General Reaction Scheme I:

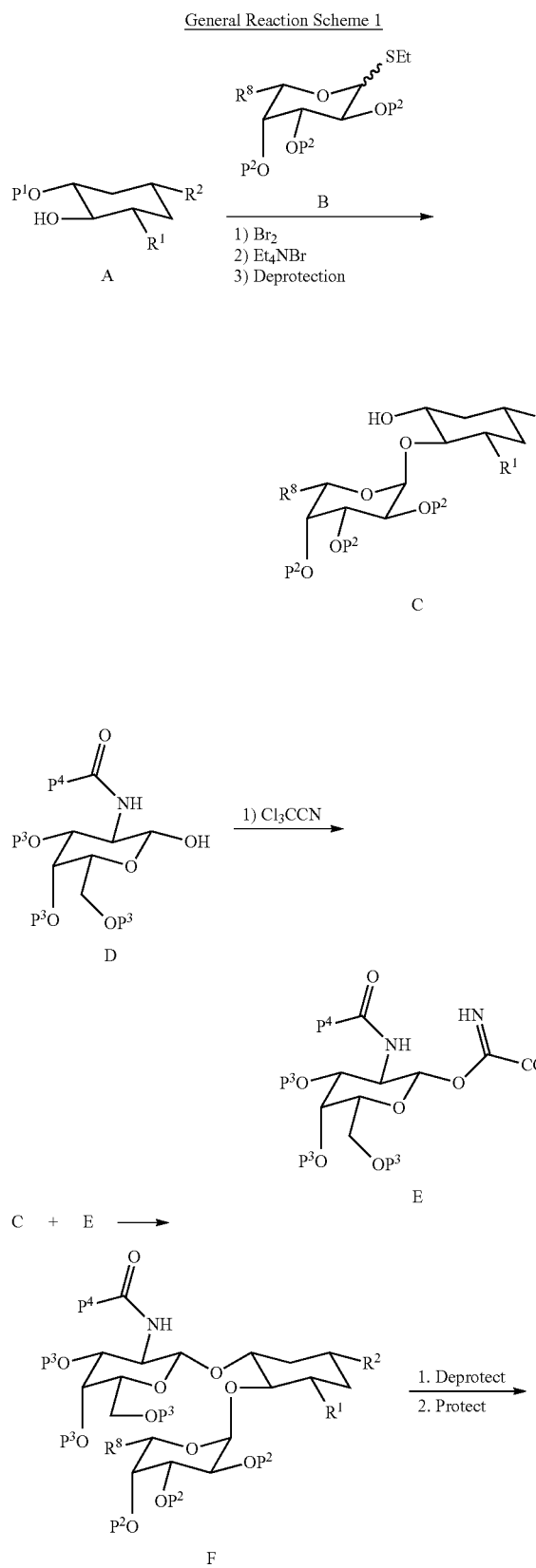

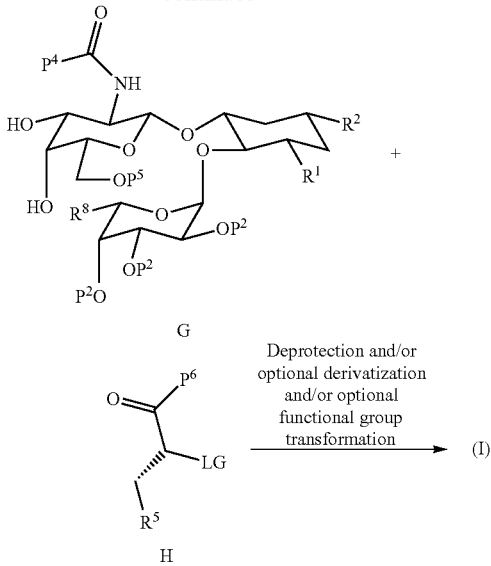

Referring to General Reaction Scheme 1, compounds of structure A, wherein $R^1$ and $R^2$ are as defined for formula (I), or are moieties which can be synthetically converted to $R^1$ or $R^2$, and $P^1$ is a suitable protecting group, can be purchased from commercial sources or prepared according to methods known in the art. Similarly, compounds of structure B, wherein $R^8$ is as defined for formula (I), or is a moiety which can be synthetically converted to $R^8$, and $P^2$ is a suitable protecting group, can be purchased from commercial sources or prepared according to methods known in the art. Reaction of A with B, under appropriate conditions (e.g., bromine followed by tetraethylamonium bromide) and subsequent selective removal of $P^1$ yields compounds of structure C.

In a parallel scheme, compound D, wherein $P^3$ is a suitable protecting group and $P^4$ is suitable protecting group or a moiety which can be synthetically manipulated to obtain $R^3$ (as defined for formula (I)), can be purchased or prepared according to known techniques. Reaction of D with a suitable activating agent (e.g., $Cl_3CCN$) yields activated compound E. Other suitable means for activating compounds of structure D are known to those of ordinary skill in the art. Coupling of C and E under appropriate conditions yields compounds of structure F.

Selective removal of $P^3$, followed by selective protection yields compounds of structure G, wherein $P^5$ is suitable protecting group. Reaction of G with H, wherein $P^6$ is suitable protecting group or a moiety which can be synthetically manipulated to obtain $R^4$ (as defined for formula (I)), $R^5$ is as defined for formula (I) and LG is a suitably activated leaving group (e.g., triflate and the like), and deprotection yields exemplary compounds of formula (I).

It will be appreciated that further synthetic manipulation may be desired to obtain certain compounds of formula (I). For example, in certain embodiments, $P^4$ may be an allyloxy group which can be transformed to obtain an alkyl amide (e.g., methyl). In other examples, $R^1$ in the above scheme may be an alkenyl moiety, and the synthetic scheme includes reduction of the alkene to an alkyl group. Various other modifications to the above General Reaction Scheme I, such as varying the starting(s) material or modifying any of the reaction products to include other non-hydroxyl moieties at $R^6$ and/or $R^7$ are possible. Methods for these and other modifications to the above exemplary scheme are well known in the art and described in more detailed in the Examples.

It will also be appreciated by those skilled in the art that in the processes described herein the functional groups of intermediate compounds may need to be protected by suitable protecting groups, even if not specifically described. Such functional groups include hydroxy, amino, mercapto and carboxylic acid. Suitable protecting groups for hydroxy include trialkylsilyl or diarylalkylsilyl (for example, t-butyldimethylsilyl, t-butyldiphenylsilyl or trimethylsilyl), tetrahydropyranyl, benzyl, and the like. Suitable protecting groups for amino, amidino and guanidino include t-butoxycarbonyl, benzyloxycarbonyl, and the like. Suitable protecting groups for mercapto include —C(O)—R" (where R" is alkyl, aryl or arylalkyl), p-methoxybenzyl, trityl and the like. Suitable protecting groups for carboxylic acid include alkyl, aryl or arylalkyl esters. Protecting groups may be added or removed in accordance with standard techniques, which are known to one skilled in the art and as described herein. The use of protecting groups is described in detail in Green, T. W. and P. G. M. Wutz, *Protective Groups in Organic Synthesis* (1999), 3rd Ed., Wiley. As one of skill in the art would appreciate, the protecting group may also be a polymer resin such as a Wang resin, Rink resin or a 2-chlorotrityl-chloride resin.

Specific and analogous reactants to those described above may also be identified through the indices of known chemicals prepared by the Chemical Abstract Service of the American Chemical Society, which are available in most public and university libraries, as well as through on-line databases (the American Chemical Society, Washington, D.C., may be contacted for more details). Chemicals that are known but not commercially available in catalogs may be prepared by custom chemical synthesis houses, where many of the standard chemical supply houses (e.g., those listed above) provide custom synthesis services. A reference for the preparation and selection of pharmaceutical salts of the present disclosure is P. H. Stahl & C. G. Wermuth "Handbook of Pharmaceutical Salts," Verlag Helvetica Chimica Acta, Zurich, 2002.

In general, the compounds used in the reactions described herein may be made according to General Reaction Scheme I, Examples 1 and 2, FIGS. 1 and 2 and/or organic synthesis techniques known to those of ordinary skill in this art, starting from commercially available chemicals and/or from compounds described in the chemical literature. "Commercially available chemicals" may be obtained from standard commercial sources including Acros Organics (Pittsburgh Pa.), Aldrich Chemical (Milwaukee Wis., including Sigma Chemical and Fluka), Apin Chemicals Ltd. (Milton Park UK), Avocado Research (Lancashire U.K.), BDH Inc. (Toronto, Canada), Bionet (Cornwall, U.K.), Chemservice Inc. (West Chester Pa.), Crescent Chemical Co. (Hauppauge N.Y.), Eastman Organic Chemicals, Eastman Kodak Company (Rochester N.Y.), Fisher Scientific Co. (Pittsburgh Pa.), Fisons Chemicals (Leicestershire UK), Frontier Scientific (Logan Utah), ICN Biomedicals, Inc. (Costa Mesa Calif.), Key Organics (Cornwall U.K.), Lancaster Synthesis (Windham N.H.), Maybridge Chemical Co. Ltd. (Cornwall U.K.), Parish Chemical Co. (Orem Utah), Pfaltz & Bauer, Inc. (Waterbury Conn.), Polyorganix (Houston Tex.), Pierce Chemical Co. (Rockford Ill.), Riedel de Haen AG (Hanover, Germany), Spectrum Quality Product, Inc. (New Brunswick, N.J.), TCI America (Portland Oreg.), Trans World Chemicals, Inc. (Rockville Md.), and Wako Chemicals USA, Inc. (Richmond Va.).

Methods known to one of ordinary skill in the art may be identified through various reference books, articles and databases. Suitable reference books and treatise that detail the synthesis of reactants useful in the preparation of compounds of the present disclosure, or provide references to articles that describe the preparation, include for example, "Synthetic Organic Chemistry," John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure," 4th Ed., Wiley-Interscience, New York, 1992. Additional suitable reference books and treatise that detail the synthesis of reactants useful in the preparation of compounds of the present disclosure, or provide references to articles that describe the preparation, include for example, Fuhrhop, J. and Penzlin G. "Organic Synthesis: Concepts, Methods, Starting Materials", Second, Revised and Enlarged Edition (1994) John Wiley & Sons ISBN: 3-527-29074-5; Hoffman, R. V. "Organic Chemistry, An Intermediate Text" (1996) Oxford University Press, ISBN 0-19-509618-5; Larock, R. C. "Comprehensive Organic Transformations: A Guide to Functional Group Preparations" 2nd Edition (1999) Wiley-VCH, ISBN: 0-471-19031-4; March, J. "Advanced Organic Chemistry: Reactions, Mechanisms, and Structure" 4th Edition (1992) John Wiley & Sons, ISBN: 0-471-60180-2; Otera, J. (editor) "Modern Carbonyl Chemistry" (2000) Wiley-VCH, ISBN: 3-527-29871-1; Patai, S. "Patai's 1992 Guide to the Chemistry of Functional Groups" (1992) Interscience ISBN: 0-471-93022-9; Quin, L. D. et al. "A Guide to Organophosphorus Chemistry" (2000) Wiley-Interscience, ISBN: 0-471-31824-8; Solomons, T. W. G. "Organic Chemistry" 7th Edition (2000) John Wiley & Sons, ISBN: 0-471-19095-0; Stowell, J. C., "Intermediate Organic Chemistry" 2nd Edition (1993) Wiley-Interscience, ISBN: 0-471-57456-2; "Industrial Organic Chemicals: Starting Materials and Intermediates: An Ullmann's Encyclopedia" (1999) John Wiley & Sons, ISBN: 3-527-29645-X, in 8 volumes; "Organic Reactions" (1942-2000) John Wiley & Sons, in over 55 volumes; and "Chemistry of Functional Groups" John Wiley & Sons, in 73 volumes.

Non-Glycomimetic E-Selectin Antagonists

As noted above, in addition to the compounds of formula I described herein, other agents are provided that bind at or near the binding site on E-selectin to which the compounds binds. The agents therefore include those that are capable of competing with a compound of formula I to inhibit E-selectin interaction with sLe$^a$ or sLe$^x$. The other agents include antibodies, polypeptides, peptides and aptamers. Such agents may be produced by a variety of means that are well known in the art. For example, the E-selectin protein is used to generate a library of antibodies. The library of antibodies is screened for one or more antibodies of interest using a compound disclosed herein as a competitive inhibitor. Alternatively, for example, the portion of E-selectin that binds the compound is identified and used to generate antibodies of interest (e.g., use of the portion as an immunogen). This portion of E-selectin may also be used to design and produce polypeptides, peptides and aptamers that compete with the compounds described herein.

In certain embodiments, a method is provided herein for mobilizing cells, for example, hematopoietic cells (e.g., hematopoietic stem cells, hematopoietic progenitor cells, leukocytes such as neutrophils) or tumor cells (e.g., hematopoietic tumor cells or malignant cells) in a subject comprising administering to the subject a pharmaceutical composition comprising a pharmaceutically acceptable excipient and an agent that is capable of competitively inhibiting binding of a compound of formula (I) to E-selectin, wherein the agent is an antibody, polypeptide, peptide or aptamer. In certain specific embodiments, the agent is capable of competitively inhibiting binding of a compound to E-selectin wherein the compound has the following structure:

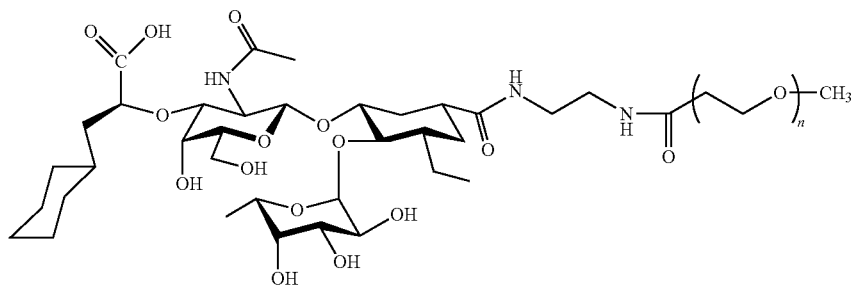

wherein n=1-100. In particular embodiments, n=8, 12, 16, 20, 24, or 28.

Antibodies and Antigen-Binding Fragments Thereof

Also provided herein are agents, which may be an antibody, polypeptide, peptide, or aptamer that that are E-selectin antagonists and may be useful for the methods and uses described herein. Such agents bind to E-selectin at or near the binding site on E-selectin to which a compound of formula (I) as provided herein binds. These agents are therefore capable of competing with a compound of formula I to bind to E-selectin and are capable of blocking (i.e., inhibiting) binding of E-selectin to an E-selectin ligand.

An agent includes an antibody, or antigen binding fragment thereof, that specifically binds to E-selectin. As described herein, the epitope to which such an antibody binds comprises amino acids at or near the binding site on E-selectin to which a compound as provided herein binds. The epitope to which such an antibody binds may include one or more amino acids contiguous with the residues to which a compound as provided herein binds and/or may include one or more amino acid residues that are non-contiguous but which interact with the compound.

As used herein, an antibody is said to be "immunospecific," "specific for" or to "specifically bind" to an antigen of interest if it reacts at a detectable level with the antigen. Affinities of antibodies and antigen binding fragments thereof can be readily determined using conventional techniques, for example, those described by Scatchard et al. (*Ann. N.Y. Acad. Sci. USA* 51:660 (1949)) and by surface plasmon resonance (SPR) (see, e.g., Wolff et al., *Cancer Res.* 53:2560-2565 (1993)). Binding properties of an antibody to an antigen may generally be determined and assessed using immunodetection methods including, for example, an enzyme-linked immunosorbent assay (ELISA), immunoprecipitation, immunoblotting, countercurrent immunoelectrophoresis, radioimmunoassays, dot blot assays, inhibition or competition assays, and the like, which may be readily performed by those having ordinary skill in the art (see, e.g., U.S. Pat. Nos. 4,376,110 and 4,486,530; Harlow et al., *Antibodies: A Laboratory Manual*, Cold Spring Harbor Laboratory (1988)).

These specific antibodies may be polyclonal or monoclonal, prepared by immunization of animals and subsequent isolation of the antibody, or cloned from specific B cells according to methods and techniques routinely practiced in the art and described herein. A variable region or one or more complementarity determining regions (CDRs) may be identified and isolated from antigen-binding fragment or peptide libraries. An antibody, or antigen-binding fragment thereof, may be recombinantly engineered and/or recombinantly produced.

An antibody may belong to any immunoglobulin class. It may be obtained from or derived from an animal, for example, fowl (e.g., chicken) and mammals, which include but are not limited to a mouse, rat, hamster, rabbit, or other rodent, a cow, horse, sheep, goat, camel, human, or other primate. The antibody may be an internalising antibody. Antibodies may generally be prepared by any of a variety of techniques known to persons having ordinary skill in the art and described herein. See, e.g., Harlow et al., *Antibodies: A Laboratory Manual*, Cold Spring Harbor Laboratory (1988); Peterson, *ILAR J.* 46:314-19 (2005); Kohler and Milstein (*Nature,* 256:495-97 (1976); *Eur. J. Immunol.* 6:511-19 (1975); Coligan et al. (eds.), *Current Protocols in Immunology,* 1:2.5.1-2.6.7 (John Wiley & Sons 1991)).

Human monoclonal anti-E-selectin antibodies may be generated by any number of techniques with which those having ordinary skill in the art will be familiar (see, e.g., U.S. Pat. No. 4,464,456; Lonberg et al., *Nature* 368:856 (1994); U.S. Pat. No. 5,877,397; Bruggemann et al., *Curr. Opin. Biotechnol.* 8:455-58 (1997); Jakobovits et al., *Ann. N. Y. Acad. Sci.* 764:525-35 (1995)); (WO 92/02551; U.S. Pat. No. 5,627,052; Babcook et al., *Proc. Natl. Acad. Sci. USA* 93:7843-48 (1996); or other procedures as known in the art). Chimeric antibodies, specific for the portion of E-selectin of interest, including humanized chimeric antibodies, may also be generated. See, e.g., Morrison et al., *Proc. Natl. Acad. Sci. USA,* 81:6851-55 (1984); Shin et al., *Methods Enzymol.* 178:459-76 (1989)). Strategies for designing humanized antibodies are routinely practiced in the art (see, e.g., Jones et al., *Nature* 321:522-25 (1986); Riechmann et al., *Nature* 332:323-27 (1988); Padlan et al., *FASEB* 9:133-39 (1995); Chothia et al., *Nature,* 342:377-83 (1989); Bajorath et al., *Ther. Immunol.* 2:95-103 (1995)).

For particular uses, antigen-binding fragments of antibodies may be desired. Antibody fragments, F(ab')$_2$, Fab, Fab', Fv, and Fd, can be obtained, for example, by proteolytic hydrolysis of the antibody (see, e.g., Weir, *Handbook of Experimental Immunology*, Blackwell Scientific, Boston (1986)), or may be synthetically prepared or genetically engineered. Antibody fragments include recombinant single chain polypeptide molecules in which light and heavy variable regions are connected by a peptide linker (scFv proteins), and minimal recognition units (comprises at least one CDR) consisting of the amino acid residues that mimic the hypervariable region. Methods and techniques for preparing and isolating antibody fragments are described in the art (see, e.g., Larrick et al., *Methods: A Companion to Methods in Enzymology* 2:106, (1991); Courtenay-Luck, in *Monoclonal Antibodies: Production, Engineering and Clinical Application*, Ritter et al. (eds.), page 166 (Cambridge University Press 1995); and Ward et al., in *Monoclonal Antibodies: Principles and Applications*, Birch et al., (eds.), page 137 (Wiley-Liss, Inc. 1995); International Patent Application Nos. PCT/US91/08694 and PCT/US91/04666); Scott et al., *Science* 249:386 (1990); Devlin et al., *Science* 249:404 (1990); Cwirla et al., *Science* 276: 1696-99 (1997); U.S. Pat. No. 5,223,409; U.S. Pat. No. 5,733,731; U.S. Pat. No. 5,498,530; U.S. Pat. No. 5,432,018; U.S. Pat. No. 5,338,665; U.S. Pat. No. 5,922,545; International Application Publication Nos. WO 96/40987 and WO 98/15833).

Antibodies may also be identified and isolated from human, rabbit, mouse or chicken immunoglobulin phage libraries. Antibodies isolated from non-human species or non-human immunoglobulin libraries may be genetically engineered to "humanize" the antibody or fragment thereof. See, e.g., Winter et al., *Annu. Rev. Immunol.* 12:433-55 (1994); Burton et al., *Adv. Immunol.* 57:191-280 (1994); U.S. Pat. No. 5,223,409; Huse et al., *Science* 246:1275-81 (1989); Kang et al., *Proc. Natl. Acad. Sci. USA* 88:4363-66 (1991); Hoogenboom et al., *J. Molec. Biol.* 227:381-388 (1992); U.S. Pat. No. 6,703,015).

An agent that is an E-selectin antagonist also includes a peptide-immunoglobulin (Ig) constant region fusion polypeptide, which includes a peptide-IgFc fusion polypeptide. The peptide may be any naturally occurring or recombinantly prepared molecule. A peptide-Ig constant region fusion polypeptide, such as a peptide-IgFc fusion polypeptide (also referred to in the art as a peptibody (see, e.g., U.S. Pat. No. 6,660,843)), comprises a biologically active peptide or polypeptide capable of altering the sLe$^a$ or sLe$^x$ binding function of E-selectin that is fused in-frame with a portion, at least one constant region domain (e.g., CH1, CH2, CH3, and/or CH4). Antibody related sequences are provided in Kabat et al. (in *Sequences of Proteins of Immunological Interest,* 4th ed. (U.S. Dept. of Health and Human Services, U.S. Government Printing Office, 1991).

Peptides and Peptidomimetics

In certain embodiments, interaction between E-selectin and sLe$^a$ or sLe$^x$ may be inhibited (i.e., inhibited, decreased, disrupted reduced in a biologically or statistically significant manner) by a peptide or peptidomimetic of the portion of E-selectin that binds a compound provided herein. The peptide and the peptide moiety of the peptidomimetic may comprise at least 3, 4, 5, 6, 7, 8, 9, 10, 11, 12, 13, 14, 15, 16-20, 21-25, 26-30, 31-35, 36-40, 41-45, or 46-50 amino acids. Peptides and peptidomimetics typically have molecular masses less than $10^4$ daltons, less than $10^3$ daltons, or less than $10^2$ daltons.

Methods for Characterizing Therapeutic Agents

Characterizing at least one biological activity of a therapeutic agent described herein may be determined by performing one or more in vitro and in vivo studies routinely practiced in the art and described herein or in the art. In vitro assays include without limitation binding assays, immunoassays, competitive binding assays and cell based activity assays. Animal model studies may also be performed, which are typically rodent animal studies described in the art or routinely developed or adapted by a person skilled in the art to characterize an agent, including determining efficacy, in vivo. By way of example, mouse animal models are used in the art for determining mobilization of cells, including hematopoietic cells, such as hematopoietic stem cells and hematopoietic progenitor cells, mature white blood cells, or tumor cells. The numbers of hematopoietic cells over time can be readily determining using macroscopic analysis and assays (e.g., immunoassays to detect particular markers present on different types of hematopoietic cells). Non-human primate animal models may be used in pre-clinical studies that precede clinical studies; however, these animal models are not typically employed in the same routine manner as rodent animal studies designed for assessing the effectiveness or other characteristics of a therapeutic. Persons skilled in the art of design and execution of animal studies can also readily determine the appropriate control groups to include with the studies as well as determine the appropriate statistical analysis or analyses for evaluating the data.

An inhibition assay may be used to screen for antagonists of E-selectin. For example, an assay may be performed to characterize the capability of a compound or other agent described herein to inhibit (i.e., reduce, block, decrease, or prevent in a statistically or biologically significant manner) interaction of E-selectin with sLe$^a$ or sLe$^x$. The inhibition assay may be a competitive binding assay, which allows the determination of IC$_{50}$ values. By way of example, the method comprises immobilizing E-selectin/Ig chimera onto a matrix (e.g., a multi-well plate, which are typically made from a polymer, such as polystyrene; a test tube, and the like); adding a composition to reduce nonspecific binding (e.g., a composition comprising non-fat dried milk or bovine serum albumin or other blocking buffer routinely used by a person skilled in the art); contacting the immobilized E-selectin with the candidate agent in the presence of sLe$^a$ comprising a reporter group under conditions and for a time sufficient to permit sLe$^a$ to bind to the immobilized E-selectin; washing the immobilized E-selectin; and detecting the amount of sLe$^a$ bound to immobilized E-selectin. Variations of such steps can be readily and routinely accomplished by a person of ordinary skill in the art.

Conditions for a particular assay include temperature, buffers (including salts, cations, media), and other components that maintain the integrity of any cell used in the assay and the compound, which a person of ordinary skill in the art will be familiar and/or which can be readily determined. A person of ordinary skill in the art also readily appreciates that appropriate controls can be designed and included when performing the in vitro methods and in vivo methods described herein.

The source of an agent that is characterized by one or more assays and techniques described herein and in the art may be a biological sample that is obtained from a subject who has been treated with the agent. The cells that may be used in the assay may also be provided in a biological sample. A "biological sample" may include a sample from a subject, and may be a blood sample (from which serum or plasma may be prepared), a biopsy specimen, one or more body fluids (e.g., lung lavage, ascites, mucosal washings, synovial fluid, urine), bone marrow, lymph nodes, tissue explant, organ culture, or any other tissue or cell preparation from the subject or a biological source. A biological sample may further refer to a tissue or cell preparation in which the morphological integrity or physical state has been disrupted, for example, by dissection, dissociation, solubilization, fractionation, homogenization, biochemical or chemical extraction, pulverization, lyophilization, sonication, or any other means for processing a sample derived from a subject or biological source. In certain embodiments, the subject or biological source may be a human or non-human animal, a primary cell culture (e.g., immune cells), or culture adapted cell line, including but not limited to, genetically engineered cell lines that may contain chromosomally integrated or episomal recombinant nucleic acid sequences, immortalized or immortalizable cell lines, somatic cell hybrid cell lines, differentiated or differentiatable cell lines, transformed cell lines, and the like.

Methods for Mobilizing Cells from the Bone Marrow

The E-selectin antagonist agents described herein, including glycomimetics, antibodies or antigen-binding fragments thereof, polypeptides, peptides and aptamers may be useful in methods for mobilizing cells from the bone marrow to the peripheral vasculature and tissues. As discussed herein, in certain embodiments, the E-selectin antagonist agents are useful for mobilizing hematopoietic cells, including hematopoietic stem cells and hematopoietic progenitor cells. As described herein, E-selectin compounds act as mobilizing agents of normal blood cell types. Accordingly, in other embodiments, the agents are used in methods for mobilizing mature white blood cells (which may also be called leukocytes herein), such as granulocytes (e.g., neutrophils, eosinophils, basophils), lymphocytes, and monocytes from the bone marrow or other immune cell compartments such as the spleen and liver. Methods are also provided for using the glycomimetic compounds described herein for mobilizing tumor cells from the bone marrow. The tumor cells may be malignant cells (e.g., tumor cells that are metastatic cancer cells, or highly invasive tumor cells) in cancers. These tumor cells may be of hematopoietic origin or may be malignant cells of another origin residing in the bone. Hematopoietic tumor cells include by way of non-limiting example, AML cells and multiple myeloma cells. Use of the glycomimetic compounds described herein may facilitate mobilization of tumor cells from the protective endothelium niches and thus render the tumor cells more susceptible to standard of care chemotherapeutic drugs or other cancer treatments. In certain embodiments, the methods and E-selectin antagonists described herein are therefore useful for treating hematologic malignancies and metastatic disease, particularly in combination or as an adjunct therapy with chemotherapy and/or radiation therapy.

In certain embodiments, the methods using the E-selectin antagonists described herein are useful for mobilizing hematopoietic cells, such as hematopoietic stem cells and progenitor cells and leukocytes (including granulocytes such as neutrophils), which are collected (i.e., harvested, obtained) from the subject receiving the E-selectin antagonist and at a later time are administered back into the same subject (autologous donor) or administered to a different subject (allogeneic donor). Hematopoietic stem cell replacement and hematopoietic stem cell transplantation have been successfully used for treating a number of diseases (including cancers) as described herein and in the art. By way of example, stem cell replacement therapy or transplantation follows myeloablation of a subject, such as occurs with administration of high dose chemotherapy and/or radiotherapy. Desirably, an allogeneic donor shares sufficient HLA antigens with the recipient/subject to minimize the risk of host versus graft disease in the recipient (i.e., the subject receiving the hematopoietic stem cell transplant). Obtaining the hematopoietic cells from the donor subject (autologous or allogeneic) is performed by apheresis or leukapheresis. HLA typing of a potential donor and the recipient and apheresis or leukapheresis are methods routinely practiced in the clinical art.

By way of non-limiting example, autologous or allogenic hematopoietic stem cells and progenitors cells may be used for treating a recipient subject who has certain cancers, such as Hodgkin lymphoma, non-Hodgkin lymphoma, or multiple myeloma. Allogeneic hematopoietic stem cells and progenitors cells may be used, for example, for treating a recipient subject who has acute leukemias (e.g., AML, ALL); chronic lymphocytic leukemia (CLL); amegakaryocytosis/congenital thrombocytopenia; aplastic anemia/refractory anemia; familial erythrophagocytic lymphohistiocytosis; myelodysplastic syndrome/other myelodysplastic disorders; osteopetrosis; paroxysmal nocturnal hemoglobinuria; and Wiskott-aldrich syndrome, for example. Exemplary uses for autologous hematopoietic stem cells and progenitors cells include treating a recipient subject who has amyloidosis; germ cell tumors (e.g., testicular cancer); or a solid tumor. Allogeneic hematopoietic stem cell transplants have also been investigated for use in treating solid tumors (see, e.g., Ueno et al., *Blood* 102:3829-36 (2003)).

In other embodiments of the methods described herein, the subject is not a donor of peripheral hematopoietic cells but has a disease, disorder, or condition for which mobilization of hematopoietic cells in the subject will provide clinical benefit. Stated another way, while this clinical situation is similar to autologous hematopoietic cell replacement, the mobilized hematopoeitic cells are not removed and given back to the same subject at a later time as occurs, for example, with a subject who receives myeloablation therapy. Accordingly, methods are provided for mobilizing hematopoietic cells, such as hematopoietic stem cells and progenitor cells and leukocytes (including granulocytes, such as neutrophils), by administering an E-selectin antagonist described herein. Mobilizing hematopoietic stem cells and progenitor cells may be useful for treating an inflammatory condition or for tissue repair or wound healing. See, e.g., Mimeault et al., *Clin. Pharmacol. Therapeutics* 82:252-64 (2007)).

In other embodiments, the methods described herein are useful for mobilizing hematopoietic leukocytes (white blood cells) in a subject, which methods may be used in treating diseases, disorders, and conditions for which an increase in white blood cells, such as neutrophils, eosinophils, lymphocytes, monocytes, basophils, will provide clinical benefit. For example, for cancer patients, the E-selectin antagonists described herein are beneficial for stimulating neutrophil production to compensate for hematopoietic deficits resulting from chemotherapy or radiation therapy. Other diseases, disorders, and conditions to be treated include infectious diseases and related conditions, such as sepsis. When the subject to whom at least one E-selectin inhibitor is administered is a donor, neutrophils may be collected for administration to a recipient subject who has reduced hematopoietic function, reduced immune function, reduced neutrophil count, reduced neutrophil mobilization, severe chronic neutropenia, leucopenia, thrombocytopenia, anemia, and acquired immune deficiency syndrome. Mobilization of mature white blood cells may be useful in subjects to improve or to enhance tissue repair, and to minimize or prevent vascular injury and tissue damage, for example following liver transplantation, myocardial infarction or limb ischemia. See, e.g., Pelus, *Curr. Opin. Hematol.* 15:285-92 (2008); Lemoli et al., *Haematologica* 93:321-24 (2008).

An E-selectin antagonist described herein (e.g., the compounds of formula I) may be used in combination with one or more other agents that mobilize hematopoietic cells. Such agents include, for example, G-CSF; AMD3100 or other CXCR4 antagonists; GRO-β (CXCL2) and an N-terminal 4-amino truncated form (SB-251353); IL-8SDF-1α peptide analogs, CTCE-0021 and CTCE-0214; and the SDF1 analog, Met-SDF-1β (see, e.g., Pelus, supra and references cited therein). The glycomimetic compounds of formula I described herein have low toxicity; by way of example, compound 25 is tolerated in mice at a dose of 1000 mg/kg. Therefore, combining a compound of formula I with other mobilizing agents used in the art may permit administration of a lower dose of GCSF or AMD3100, for example, than required in the absence of a compound of formula I. The appropriate therapeutic regimen for administering an E-selectin antagonist in combination with another mobilizing agent or agents can be readily determined by a person skilled in the clinical art.

As understood by a person of ordinary skill in the medical art, the terms, "treat" and "treatment," refer to medical management of a disease, disorder, or condition of a subject (i.e., patient, individual) (see, e.g., Stedman's Medical Dictionary). In general, an appropriate dose and treatment regimen provide at least one glycomimetic compound or other agent described herein in an amount sufficient to provide therapeutic and/or prophylactic benefit. Therapeutic and/or prophylactic benefit includes, for example, an improved clinical outcome, both therapeutic treatment and prophylactic or preventative measures, wherein the object is to prevent or slow or retard (lessen) an undesired physiological change or disorder, or to prevent or slow or retard (lessen) the expansion or severity of such disorder. As discussed herein, beneficial or desired clinical results from treating a subject include, but are not limited to, abatement, lessening, or alleviation of symptoms that result from or are associated with the disease, condition, or disorder to be treated; decreased occurrence of symptoms; improved quality of life; longer disease-free status (i.e., decreasing the likelihood or the propensity that a subject will present symptoms on the basis of which a diagnosis of a disease is made); diminishment of extent of disease; stabilized (i.e., not worsening) state of disease; delay or slowing of disease progression; amelioration or palliation of the disease state; and remission (whether partial or total), whether detectable or undetectable; and/or overall survival. "Treatment" can also mean prolonging survival when compared to expected survival if a subject were not receiving treatment. Subjects in need of treatment include those who already have the disease, condition, or disorder as well as subjects prone to have or at risk of developing the disease, condition, or disorder, and those in which the disease, condition, or disorder is to be prevented (i.e., decreasing the likelihood of occurrence of the disease, disorder, or condition).

In particular embodiments of the methods described herein, the subject is a human or non-human animal. A subject in need of the treatments described herein may exhibit symptoms or sequelae of cancer disease, disorder, or condition described herein or may be at risk of developing the disease, disorder, or condition. Non-human animals that may be treated include mammals, for example, non-human primates (e.g., monkey, chimpanzee, gorilla, and the like), rodents (e.g., rats, mice, gerbils, hamsters, ferrets, rabbits), lagomorphs, swine (e.g., pig, miniature pig), equine, canine, feline, bovine, and other domestic, farm, and zoo animals.

The effectiveness of a compound, agent, or composition described herein in treating or preventing a disease or disorder or condition, and determining and adjusting an appropriate dosing regimen (e.g., adjusting the amount of compound per dose and/or number of doses and frequency of dosing), can readily be determined by a person of ordinary skill in the medical and clinical arts. One or any combination of diagnostic methods, including physical examination, assessment and monitoring of clinical symptoms, and performance of analytical tests and methods described herein, may be used for monitoring the health status of the subject.

Mobilization of hematopoietic cells can be monitored using methods and techniques routinely practiced in the art the skilled person. For example, determining total white blood cell counts and differential white blood cell counts are routine clinical laboratory procedures. Hematopoietic stem cells may be identified by identifying the presence or absence of certain cell surface markers (see, e.g., Baum et al., *Proc. Natl. Acad. Sci. USA* 89:2804-2808 (1992)). For example, the presence and level of hematopoietic stem cells can be determined by methods that detect the presence of CD34 on the surface of cells (i.e., $CD34^+$ cells).

Pharmaceutical Compositions and Methods of Using Pharmaceutical Compositions

Also provided herein are pharmaceutical compositions that comprise any one or more of the E-selectin antagonist agents described herein, such as one or more of the glycomimetic compounds of formula I, substructures of formula Ia, and specific structures thereof, described herein. The isolated antibodies described herein may also be prepared for pharmaceutical use in a subject, including a human subject. The compounds described herein may be formulated in a pharmaceutical composition for use in medicaments and therapeutics for mobilizing hematopoietic cells (including hematopoietic stem cells and progenitor cells) and for treatment or preventive (or prophylactic) treatment (e.g., reducing the likelihood of occurrence or of exacerbation of a disease, or of one or more symptoms of the disease) of a disease or disorder for which mobilizing hematopoietic cells is beneficial or for which receiving a hematopoietic cell transplant or replacement is beneficial. The methods and excipients described herein are exemplary and are in no way limiting.

In pharmaceutical dosage forms, any one or more of the glycomimetic compounds of formula I, substructures and specific structures described herein may be administered in the form of a pharmaceutically acceptable derivative, such as a salt, or they may also be used alone or in appropriate association, as well as in combination, with other pharmaceutically active compounds.

An effective amount or therapeutically effective amount refers to an amount of a glycomimetic compound or a composition comprising one or more compounds; or one or more isolated antibodies (or other E-selectin antagonist described herein) that when administered to a subject, either as a single dose or as part of a series of doses, is effective to produce a desired therapeutic effect. Optimal doses may generally be determined using experimental models and/or clinical trials. Design and execution of pre-clinical and clinical studies for each of the therapeutics (including when administered for prophylactic benefit) described herein are well within the skill of a person of ordinary skill in the relevant art. The optimal dose of a therapeutic may depend upon the body mass, weight, or blood volume of the subject. In general, the amount of a compound described herein, that is present in a dose, ranges from about 0.01 μg to about 1000 μg per kg weight of the host. In general, the amount of a polypeptide or peptide, or an antibody or antigen-binding fragment thereof as described herein, present in a dose, also ranges from about 0.01 μg to about 1000 μg per kg of subject. The use of the minimum dose that is sufficient to provide effective therapy is usually preferred. Subjects may generally be monitored for therapeutic effectiveness using assays suitable for the disease or condition being treated or prevented, which assays will be familiar to those having ordinary skill in the art and are described herein. The level of a compound or polypeptide that is administered to a subject may be monitored by determining the level of the compound, peptide, antibody or antigen-binding fragment thereof, or polypeptide (or a metabolite of any of the aforementioned molecules) in a biological fluid, for example, in the blood, blood fraction (e.g., serum), and/or in the urine, and/or other biological sample from the subject. Any method practiced in the art to detect the molecule may be used to measure the level of the molecule during the course of a therapeutic regimen.

The dose of a compound, peptide, antibody or antigen-binding fragment thereof, or polypeptide described herein may depend upon the subject's condition, that is, stage of the disease, severity of symptoms caused by the disease, general health status, as well as age, gender, and weight, and other factors apparent to a person of ordinary skill in the medical art. Similarly, the dose of the therapeutic for treating a disease or disorder may be determined according to parameters understood by a person of ordinary skill in the medical art.

Pharmaceutical compositions may be administered in a manner appropriate to the disease or disorder to be treated as determined by persons of ordinary skill in the medical arts. An appropriate dose and a suitable duration and frequency of administration will be determined by such factors as discussed herein, including the condition of the patient, the type and severity of the patient's disease, the particular form of the active ingredient, and the method of administration. In general, an appropriate dose (or effective dose) and treatment regimen provides the pharmaceutical composition(s) as described herein in an amount sufficient to provide therapeutic and/or prophylactic benefit (for example, an improved clinical outcome, such as more frequent complete or partial remissions, or longer disease-free and/or overall survival, or a lessening of symptom severity or other benefit as described in detail above).

The pharmaceutical compositions described herein may be administered to a subject in need thereof by any one of several routes that effectively deliver an effective amount of the compound. Such administrative routes include, for example, topical, oral, nasal, intrathecal, enteral, buccal, sublingual, transdermal, rectal, vaginal, intraocular, subconjunctival, sublingual or parenteral administration, including subcutaneous, intravenous, intramuscular, intrasternal, intracavernous, intrameatal or intraurethral injection or infusion. Compositions administered by these routes of administration and others are described in greater detail herein.

A pharmaceutical composition may be a sterile aqueous or sterile non-aqueous solution, suspension or emulsion, which additionally comprises a physiologically acceptable excipient (pharmaceutically acceptable or suitable excipient or carrier) (i.e., a non-toxic material that does not interfere with the activity of the active ingredient). Such compositions may be in the form of a solid, liquid, or gas (aerosol). Alternatively, compositions described herein may be formulated as a lyophilizate, or compounds and polypeptides or peptides described herein may be encapsulated within liposomes using technology known in the art. Pharmaceutical compositions may also contain other components, which may be biologically active or inactive. Such components include, but are not limited to, buffers (e.g., neutral buffered saline or phosphate buffered saline), carbohydrates (e.g., glucose, mannose, sucrose or dextrans), mannitol, proteins, polypeptides or amino acids such as glycine, antioxidants, chelating agents such as EDTA or glutathione, stabilizers, dyes, flavoring agents, and suspending agents and/or preservatives.

Any suitable excipient or carrier known to those of ordinary skill in the art for use in pharmaceutical compositions may be employed in the compositions described herein. Excipients for therapeutic use are well known, and are described, for example, in *Remington: The Science and Practice of Pharmacy* (Gennaro, 21 Ed. Mack Pub. Co., Easton, Pa. (2005)). In general, the type of excipient is selected based on the mode of administration, as well as the chemical composition of the active ingredient(s). Pharmaceutical compositions may be formulated for any appropriate manner of administration, including, for example, topical, oral, nasal, intrathecal, enteral, buccal, sublingual, transdermal, rectal, vaginal, intraocular, subconjunctival, sublingual or parenteral administration, including subcutaneous, intravenous, intramuscular, intrasternal, intracavernous, intrameatal or intraurethral injection or infusion. For parenteral administration, the carrier preferably comprises water, saline, alcohol, a fat, a wax or a buffer. For oral administration, any of the above excipients or a solid excipient or carrier, such as mannitol, lactose, starch, magnesium stearate, sodium saccharine, talcum, cellulose, kaolin, glycerin, starch dextrins, sodium alginate, carboxymethylcellulose, ethyl cellulose, glucose, sucrose and/or magnesium carbonate, may be employed.

A pharmaceutical composition (e.g., for oral administration or delivery by injection) may be in the form of a liquid. A liquid pharmaceutical composition may include, for example, one or more of the following: a sterile diluent such as water for injection, saline solution, preferably physiological saline, Ringer's solution, isotonic sodium chloride, fixed oils that may serve as the solvent or suspending medium, polyethylene glycols, glycerin, propylene glycol or other solvents; antibacterial agents; antioxidants; chelating agents; buffers and agents for the adjustment of tonicity such as sodium chloride or dextrose. A parenteral preparation can be enclosed in ampoules, disposable syringes or multiple dose vials made of glass or plastic. The use of physiological saline is preferred, and an injectable pharmaceutical composition is preferably sterile.

For oral formulations, at least one of the E-selectin antagonist agents described herein can be used alone or in combination with appropriate additives to make tablets, powders, granules or capsules, for example, with any one or more conventional additives, disintegrators, lubricants, and if desired, diluents, buffering agents, moistening agents, preservatives, coloring agents, and flavoring agents. The compositions may be formulated to include a buffering agent to provide for protection of the active ingredient from low pH of the gastric environment and/or an enteric coating. A composition may be formulated for oral delivery with a flavoring agent, e.g., in a liquid, solid or semi-solid formulation and/or with an enteric coating.

Oral formulations may be provided as gelatin capsules, which may contain the active compound or biological along with powdered carriers. Similar carriers and diluents may be used to make compressed tablets. Tablets and capsules can be manufactured as sustained release products to provide for continuous release of active ingredients over a period of time. Compressed tablets can be sugar coated or film coated to mask any unpleasant taste and protect the tablet from the atmosphere, or enteric coated for selective disintegration in the gastrointestinal tract.

A pharmaceutical composition may be formulated for sustained or slow release. Such compositions may generally be prepared using well known technology and administered by, for example, oral, rectal or subcutaneous implantation, or by implantation at the desired target site. Sustained-release formulations may contain the active therapeutic dispersed in a carrier matrix and/or contained within a reservoir surrounded by a rate controlling membrane. Excipients for use within such formulations are biocompatible, and may also be biodegradable; preferably the formulation provides a relatively constant level of active component release. The amount of active therapeutic contained within a sustained release formulation depends upon the site of implantation, the rate and expected duration of release, and the nature of the condition to be treated or prevented.

The pharmaceutical compositions described herein can be formulated as suppositories by mixing with a variety of bases such as emulsifying bases or water-soluble bases. The pharmaceutical compositions may be prepared as aerosol formulations to be administered via inhalation. The compositions may be formulated into pressurized acceptable propellants such as dichlorodifluoromethane, propane, nitrogen and the like.

Any one or more of the E-selectin antagonists described herein may be administered topically (e.g., by transdermal administration). Topical formulations may be in the form of a transdermal patch, ointment, paste, lotion, cream, gel, and the like. Topical formulations may include one or more of a penetrating agent or enhancer (also call permeation enhancer), thickener, diluent, emulsifier, dispersing aid, or binder. Physical penetration enhancers include, for example, electrophoretic techniques such as iontophoresis, use of ultrasound (or "phonophoresis"), and the like. Chemical penetration enhancers are agents administered either prior to, with, or immediately following administration of the therapeutic, which increase the permeability of the skin, particularly the stratum corneum, to provide for enhanced penetration of the drug through the skin. Additional chemical and physical penetration enhancers are described in, for example, Transdermal Delivery of Drugs, A. F. Kydonieus (ED) 1987 CRL Press; Percutaneous Penetration Enhancers, eds. Smith et al. (CRC Press, 1995); Lenneräs et al., *J. Pharm. Pharmacol.* 54:499-508 (2002); Karande et al., *Pharm. Res.* 19:655-60 (2002); Vaddi et al., *Int. J. Pharm.* 91:1639-51 (2002); Ventura et al., *J. Drug Target* 9:379-93 (2001); Shokri et al., *Int. J. Pharm.* 228 (1-2):99-107 (2001); Suzuki et al., *Biol. Pharm. Bull.* 24:698-700 (2001); Alberti et al., *J. Control Release* 71:319-27 (2001); Goldstein et al., *Urology* 57:301-5 (2001); Kiijavainen et al., *Eur. J. Pharm. Sci.* 10:97-102 (2000); and Tenjarla et al., *Int. J. Pharm.* 192:147-58 (1999).

Kits with unit doses of one or more of the compounds, polypeptides, peptides, aptamers, antibodies and antigen binding fragments thereof described herein, usually in oral or injectable doses, are provided. Such kits may include a container containing the unit dose, an informational package insert describing the use and attendant benefits of the therapeutic in treating the pathological condition of interest, and optionally an appliance or device for delivery of the composition.

EXAMPLES

Example 1

Synthesis of E-Selectin Inhibitor

Exemplary glycomimetic compounds of formula I were synthesized as described in this Example and as shown in the exemplary synthesis schemes set forth in FIGS. 1-2.

Synthesis of Compound 2

Compound 1 (60 g) was suspended in $H_2O$ (800 ml) and cooled to 0° C. Solid $NaHCO_3$ (120 g) was added in portion with stirring and then a solution of KI (474.3 g) and $I_2$ (127 g) in $H_2O$ (800 ml) was added with stirring. Reaction mixture was stirred at room temperature overnight in the dark. Reaction mixture was then extracted with $CH_2Cl_2$ (3×500 ml). The organic layer was washed with $Na_2S_2O_3$ solution (2×500 ml) and then the combined aqueous layers were extracted with $CH_2Cl_2$ (2×300 ml). Organic layers (2100 ml) were combined and washed with cold $H_2O$ (1×500 ml) and cold brine (1×500 ml). The organic layer was dried over $Na_2SO_4$, filtered, and concentrated to dryness to give compound 2 as light yellow crystals (119 g). Purity: >95% by TLC.

Synthesis of Compound 3:

To a solution of compound 2 (119 g) in THF (1600 ml) was added DBU (119 ml) with stirring at room temperature and the reaction mixture was gently refluxed overnight with stirring. Some precipitate forms and TLC showed no starting material left. The reaction mixture was concentrated to dryness and dissolved in EtOAc (300 ml), washed with 0.5 M HCl (200 ml) until pH 2-3 of the aqueous wash, and then the organic layer was further washed with $H_2O$ (200 ml). Aqueous layers were combined and extracted with EtOAc (3×200 ml) to produce a second organic layer. Combined organic layers (900 ml) were washed with brine, dried ($Na_2SO_4$), filtered and concentrated to dryness to give compound 3 (58 g). Purity: >95% by TLC.

Synthesis of Compound 4:

To a solution of compound 3 (58 g) in MeOH (800 ml) was added $NaHCO_3$ (47 g) with stirring. The reaction mixture was stirred under gentle reflux for 3 h, cooled to room temperature, filtered and concentrated to dryness. The residue was dissolved in EtOAc (300 ml) and washed with $H_2O$. Aqueous layer was extracted with EtOAc (3×100 ml). Combined organic layers (600 ml) were washed with 0.5M HCl (200 ml), $H_2O$ (100 ml), and brine (100 ml), dried ($Na_2SO_4$), filtered, and concentrated to dryness. The residue was purified by column chromatography ($SiO_2$, Hexanes-EtOAc 3:1→3:2) to give compound 4 (54 g). Purity: >95% by TLC.

Synthesis of Compound 5:

Compound 4 (31 g) was dissolved in tBuOMe (620 ml) and vinylacetate (166 ml) added with vigorous stirring. Novozyme 435 (1.4 g) was added and vigorous stirring continued for 5.5 h. The reaction mixture was filtered and stored at −20° C. After 12-18 hours, another batch of NOVOZYME 435 resin (1.4 g) was added and stirred vigorously for 8 h. Resin was filtered and concentrated to dryness. Oily residue was purified by COMBIFLASH® system (silica) using 0→50% EtOAc/Hexanes to give compound 5 (13.0 g).

Synthesis of Compound 6:

Compound 5 (13.5 g) was dissolved in $CH_2Cl_2$ (300 ml) under argon and TBDMS-Cl (26.4 g) added with stirring at room temperature under argon. DBU (32.4 ml) was added and stirring continued for overnight at room temperature under argon. MeOH (30 ml) was added and washed with cold saturated solution of $NaHCO_3$ (200 ml), brine (150 ml). The organic layer was dried (Na2SO4), filtered and concentrated to dryness. The residue was purified by COMBI-FLASH® system ($SiO_2$) using solvent EtOAc-Hexanes (0-15%) to give compound 6 (18 g). Purity >95% by TLC.

Synthesis of Compound 7:

Compound 6 (12 g) was dissolved in $CH_2Cl_2$ (400 ml) and cooled to 0° C. m-chloroperbenzoic acid (77%, 19 g) was added and the solution stirred for few hours during which the temperature of the reaction mixture reached to room temperature. The stirring was continued overnight at room temperature. $CH_2Cl_2$ (300 ml) was added and washed with cold saturated solution of $NaHCO_3$ (3×400 ml), brine (cold), dried ($Na_2SO_4$), filtered, and concentrated to dryness. The residue was purified by COMBIFLASH® system ($SiO_2$) using EtOAc-Hexanes (0→30%) to give 7 (9 g). Purity: >95% by TLC.

Synthesis of Compound 8:

All operation of this step was done in argon atmosphere. CuCN (9.42 g) was dried at 160° C. under vacuum for 40 min, cooled down to room temperature and suspended in THF (80 ml). The mixture was cooled down to −78° C. During this time, tetravinyltin (12 ml) and n-BuLi in hexane (2.5 M, 100 ml) were reacted for 30 min at 0° C. in THF (30 ml). This solution was added to the mixture of CuCN in THF, and the resulting mixture was stirred for 30 min. at −20° C. The mixture was then cooled to −78° C. and to which was added a solution of freshly distilled $BF_3.Et2O$ (6 ml) in THF (20 ml). The mixture was stirred for 20 min. at −78° C. Compound 7 (5 g) in THF (40 ml) was added and the reaction mixture was stirred at −78° C. for 5 h. MeOH (7 ml) and $Et_3N$ (3 ml) was added and the mixture was concentrated to dryness. The residue was dissolved in EtOAc (200 ml) and washed with saturated solution of $NaHCO_3$ (2×100 ml), brine (100 ml), dried ($Na_2SO_4$), filtered, and concentrated to dryness. The residue was purified by COMBIFLASH® system (SiO2) using solvent EtOAc-Hexanes (0→5%) to give compound 8 (2.5 g).

Synthesis of Compound 10:

Compound 8 (2.25 g, 7 mmol) was dissolved in toluene (7 ml) and solvent evaporated off. The process was repeated twice and finally dried under vacuum for 15 min. The residue was dissolved in anhydrous $CH_2Cl_2$ (45 ml) and DMF (45 ml) was added. The solution was stirred under argon at room temperature and molecular sieves (3 g, 4 Å, powdered and flamed dried) added. $Et_4NBr$ (3.3 g, 15.7 mmol, 2.2 equivalents, dried at 200° C. for 2 h) was added and the stirring continued for 1 h at room temperature under argon.

Compound 9 (5.13 g, 10 mmol, 1.42 equivalents) was co-evaporated with toluene (3×20 ml), dried under vacuum, and dissolved in $CH_2Cl_2$ (45 ml). The reaction mixture was placed in an ice-bath and stirred for 10 min. To this solution was added $Br_2$ (0.8 ml, 15 mmol, 1.5 equivalents) drop-wise with stirring in the ice-bath. Stirring was continued for 40 min at the same temperature. The ice-bath was removed and cyclohexene (2.1 ml) added slowly with stirring after 10 min. The reaction mixture was stirred for 10 min. and added slowly to the reaction mixture above with stirring at room temperature under argon. Stirring continued for 17 h and then pyridine (4 ml) was added, filtered and the filtrate concentrated to dryness. The residue was dissolved in $CH_2Cl_2$ (100 ml) and transferred to a separatory funnel. The organic layer was washed with cold brine (2×75 ml), dried ($Na_2SO_4$), filtered and concentrated to dryness, co-evaporated with toluene (3×50 ml), and dried under vacuum. The residue was dissolved in THF (8 ml) and a solution of TBAF (1 M in THF, 10 ml, 10 mmol, 1.42 equivalents) added with stirring at room temperature. Stirring was continued for 15 h and solvent evaporated off. The residue was dissolved in $CH_2Cl_2$ (100 ml) and transferred to a separatory funnel, washed with cold brine (2×75 ml), dried ($Na_2SO_4$), filtered, and concentrated to dryness. The residue was purified by column chromatography (Hexanes-Ethyl acetate from 100% hexanes to 70% hexanes in EtOAc) to give compound 10 (1.6 g, 2.59 mmol, 37% overall in two steps). TLC: 5% EtOAc in hexanes and 33% EtOAc in hexanes.

Synthesis of Compound 12:

Commercially available compound 11 (10 g) was dried overnight under vacuum overnight and added to a solution of NaOMe (5 M, 10 ml) in MeOH (200 ml) with stirring at room temperature under argon. Stirring was continued for overnight at room temperature argon, and $Et_3N$ (7 ml) was added followed by allylchloroformate (3.5 ml) dropwise. Stirring was continued for 6 h at room temperature under argon. The reaction mixture was concentrated to dryness and dissolved in pyridine (100 ml). $Ac_2O$ (50 ml) was added at room temperature under argon and stirred at room temperature for overnight. The reaction mixture was concentrated to dryness and purified by column chromatography on COMBIFLASH® system using EtOAc-Hexanes (0-100%). The desired fractions were collected and concentrated to dryness to give Compound 12 (10.2 g).

Synthesis of Compound 13:

Compound 12 (7.5 g) was dissolved in DMF (140 ml) to which was added $NH_4OAC$ (4.05 g) with stirring. Stirring was continued for overnight at room temperature under argon. The next day the reaction mixture was stirred at 50° C. under argon for 8 h. The reaction mixture was concentrated to dryness and the residue dissolved in EtOAc (150 ml), washed with brine (100 ml), dried ($Na_2SO_4$), filtered, and concentrated to dryness. The residue was purified by column chromatography ($SiO_2$, Hexanes-EtOAc 2:1→1:2) to give Compound 13 (6 g).

Synthesis of Compound 14:

Compound 13 (6 g) was dissolved in $CH_2Cl_2$ (50 ml) to which was added $CCl_3CN$ (6 ml) and DBU (0.5 ml). The reaction mixture was stirred at room temperature for 0.5 h, solvent was evaporated off and the residue was purified by column chromatography (silica gel) to give Compound 14 (4.5 g).

Synthesis of Compound 15:

Compound 10 (2 g) and compound 14 (2.1 g) was dissolved in $CH_2Cl_2$ (40 ml). To this solution were added molecular sieves (4 Å, 0.8 g) and stirred at room temperature for 30 min. The solution was then cooled to 0° C. and $BF_3.Et_2O$ (0.25 ml dissolved in 5 ml) is added with stirring at 0° C. The reaction mixture was stirred at 0° C. for 2 h. $Et_3N$ (0.5 ml) was added and the solvent was evaporated off. The residue was purified by column chromatography (silica gel) to give Compound 15 (1.8 g).

Synthesis of Compound 16:

Compound 15 (1.7 g) was treated with 0.01 N NaOMe in MeOH (10 ml) for 2 h and neutralized with IR-120 ($H^+$) resin, filtered, and concentrated to dryness to give Compound 16 (1.25 g).

Synthesis of Compound 17:

To a solution of compound 16 (1.2 g) in $CH_3CN$ (30 ml) was added Et3N (0.28 ml) and cooled to 0° C. To this solution was added BzCN (0.35 mg in 10 ml $CH_3CN$) dropwise during 20 min at 0° C. The reaction mixture was stirred for 1 h at 0° C. and concentrated to dryness. The residue was purified by column chromatography (silica gel) to give compound 17 (0.95 g).

Synthesis of Compound 19:

Compound 17 (0.9 g) was dissolved in MeOH (12 ml). To this solution was added $Bu_2SnO$ (0.4 g) and the mixture was refluxed for 2 h. Solvent was evaporated off and the residual solvent was co-evaporated off with toluene 3 times. The residue was dissolved in dimethoxy ethane (15 ml). To this solution was added CsF (0.8 g) and compound 18 (2.1 g, synthesized as described previously, *J. Med. Chem.* 42:4909, 1999). The reaction mixture was stirred overnight at room temperature, and the solvent was evaporated off. The residue was purified by column chromatography to give compound 19 (0.8 g).

Synthesis of Compound 20:

Compound 19 (0.7 g) was dissolved in $CH_2Cl_2$ (20 ml). To this solution was added $Pd(Ph)_4$ (0.14 g), $Bu_3SnH$ (0.15 ml), and $Ac_2O$ (0.3 ml) and the reaction mixture is stirred at room temperature for 1 h. Solvent was evaporated off and the residue was purified by column chromatography (silica gel) to give compound 20 (0.5 g).

Synthesis of Compound 21:

To a solution of compound 20 (0.45 g) in dioxane-$H_2O$—AcOH (10:2:1, 2.6 ml) was added 10% Pd—C (0.15 g), and the reaction mixture was shaken at room temperature under positive pressure (20 psi) of hydrogen for 5 h. The solid was filtered off, and the filtrate was concentrated to dryness. The residue was purified by column chromatography (silica gel) to give Compound 21 (0.3 g).

Synthesis of Compound 22:

Compound 21 (0.28 g) was treated with 0.025 N NaOMe in MeOH (5 ml) for 4 h, neutralized with IR-120 (H+) resin, filtered, and the filtrate was concentrated to dryness to give compound 22 (0.21 g).

Synthesis of Compound 23:

Compound 22 (0.18 g) was dissolved in ethylenediamine (2 ml) and stirred at 80° C. for 8 h. Solvent was evaporated off and the residue purified using Sep-pak C18 cartridges to give compound 23 (0.15 g).

Synthesis of Compound 25:

Compound 23 (200 mg) was dissolved into 2 mL DMF to which $Et_3N$ (0.1 ml) was added. To this solution was added MePEG$_{12}$NHS (206 mg) (compound 24). The reaction mixture was stirred at room temperature for 1 h. The solid residue was washed with EtOAc (3×4 ml). The solid residue was dissolved in $H_2O$ (2 ml) and the pH of the resulting solution was adjusted to 7.4 by addition of NaOH. The reaction mixture was purified by reverse-phase chromatography (Waters Sep-pak C18 cartridges) using MeOH—$H_2O$ (0-50%) as an eluent. The fractions containing the product were combined, concentrated to dryness and lyophilized to give compound 25 (280 mg). See FIG. 1D.

$^1$H-NMR (400 MHz, $D_2O$): δ 4.94 (d, J=4.0 Hz, 1H), 4.81 (dd, J=6.8 Hz, J=3.2 Hz, 1H), 4.43 (d, J=8.4 Hz, 1H), 3.90 (br t, J=9.2 Hz, 1H), 3.81-3.78 (m, 3H), 3.75-3.71 (m, 2H), 3.70-3.67 (m, 2H), 3.65-3.58 (m, 46H), 3.54-3.52 (m, 2H), 3.48 (br t, J=6.0 Hz, 1H), 3.36 (br d, J=9.6 Hz, 1H), 3.29 (s, 3H), 3.27-3.18 (m, 5H), 2.43 (t, J=6.0 Hz, 2H), 2.25 (bt, J=12.4 Hz, 1H), 2.08-2.05 (m, 1H), 1.97 (s, 3H), 1.79-1.76 (m, 2H), 1.68-1.21 (m, 11H), 1.19-1.04 (m, 8H), 0.86-0.76 (m, 5H); LC-MS Calculated for $C_{60}H_{108}NaN_3O_{27}$ [1326.7 (M+), 1348.7 (M+Na)]. A scan of the NMR spectrum is presented in FIGS. 3A-3D.

Synthesis of Compound 26:

Compound 26 was synthesized as described for compound 25 (see FIG. 1D) except that the PEG reactant had an n of 8 (i.e., 8 repeating PEG units) rather than 12 as for the synthesis of compound 25.

Compound 26:

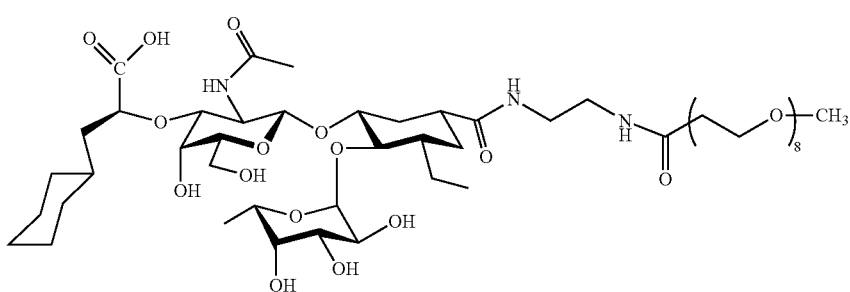

Compound 26

Synthesis of Compound 27:

Compound 27 was synthesized as described in FIG. 2.

Compound 27:

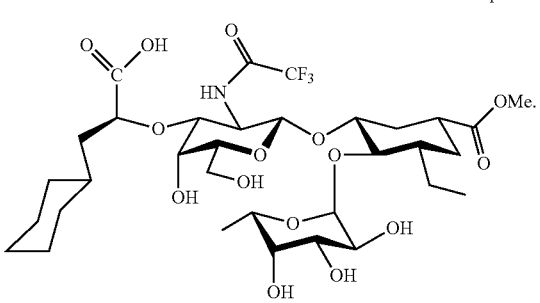

Compound 27

Synthesis of Compound 27A: Compound 19 (0.05 g) was dissolved in $CH_2Cl_2$ (10 ml). To this solution was added $Pd[(Ph_3)P]_4$ (5 mg), Bu3SnH (0.0011 ml), and $(CF_3CO)_2O$ (0.0015 ml) with stirring at room temperature. Stirring continued for 30 min at room temperature. The reaction mixture was evaporated to dryness under reduced pressure and the residue was purified by column chromatography (silica gel) to give compound 27A (0.030 g).

Compound 27A (0.025 g) was subjected to hydrogenation with 10% Pd—C exactly in same way as described for compound 21 and the solvent was evaporated off after filtering of the catalyst. The residue was treated with NaOMe in MeOH as described for compound 22, neutralized with IR-120 (H+) resin, filtered, and the solvent was evaporated off. The residue was purified by reverse phase (C18) HPLC to give compound 27 (7 mg).

Synthesis of Compound 28:
Compound 28:
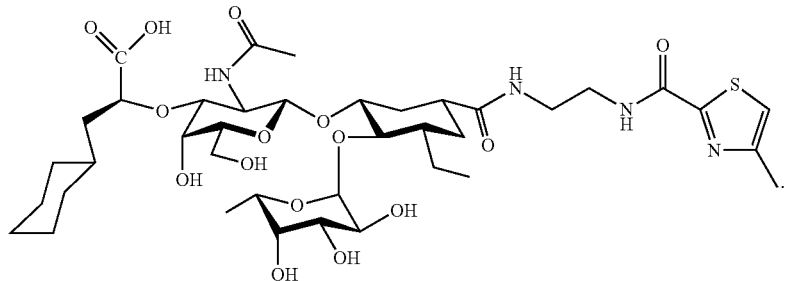
Compound 28
Synthesis Scheme for Compound 28:
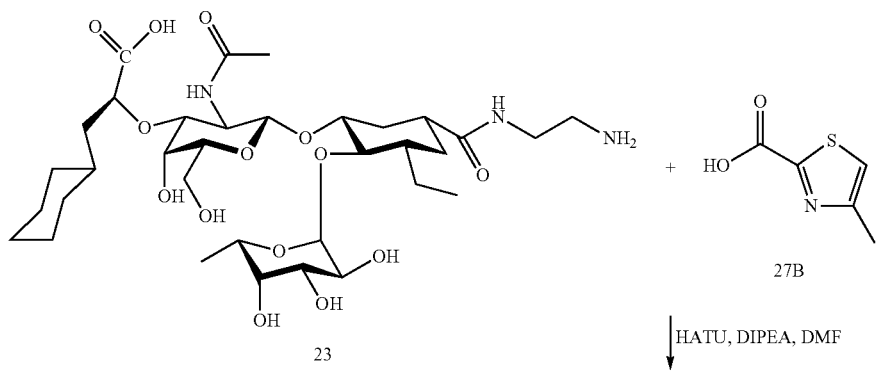
HATU, DIPEA, DMF
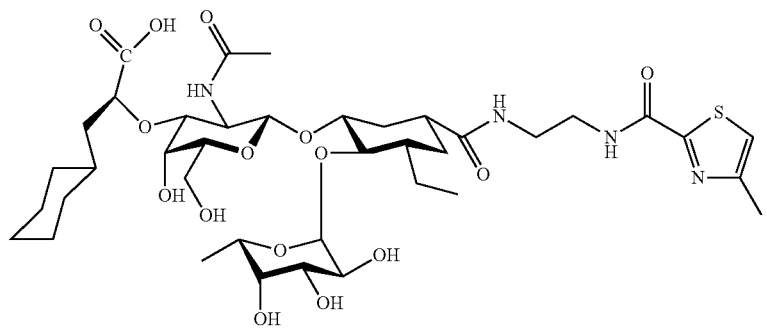

Synthesis of Compound 28: Commercially available compound 27B (0.014 g) was dissolved in DMF (1 ml). To this solution was added DIPEA (0.00175 ml) and HATU (0.038 g) and the reaction mixture was stirred for 2 min at room temperature. Compound 23 (0.035 g) was added and the reaction mixture was stirred for 1 h at room temperature. Solvent was evaporated off and the residue was purified by HPLC (C18) to give compound 28 (17 mg).

Synthesis of Compound 29:

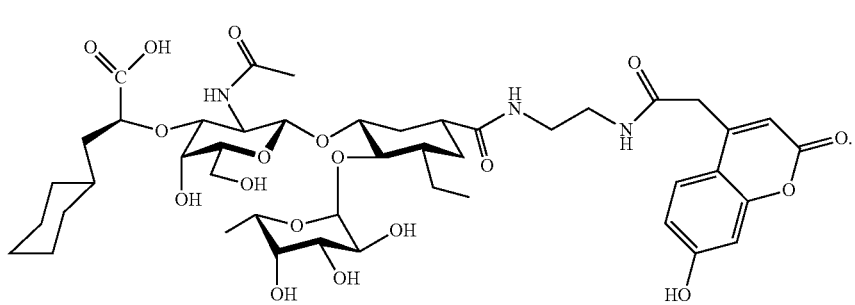

Compound 29

20

Synthesis Scheme for Compound 29:

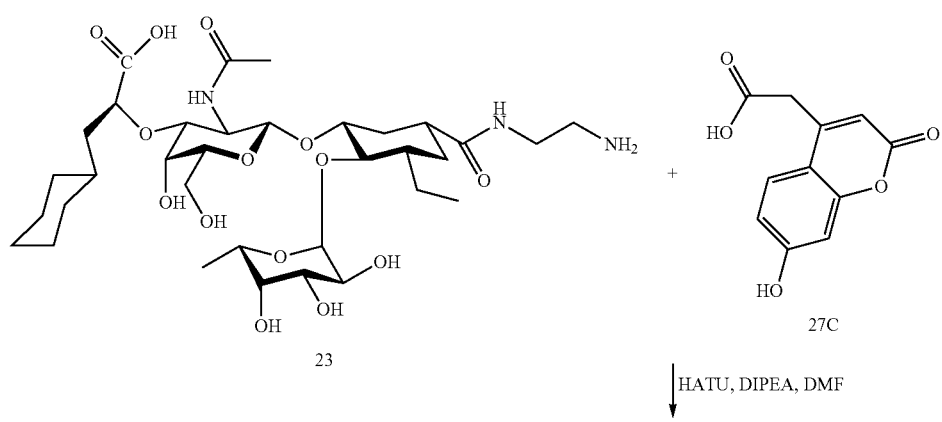

23 + 27C

HATU, DIPEA, DMF

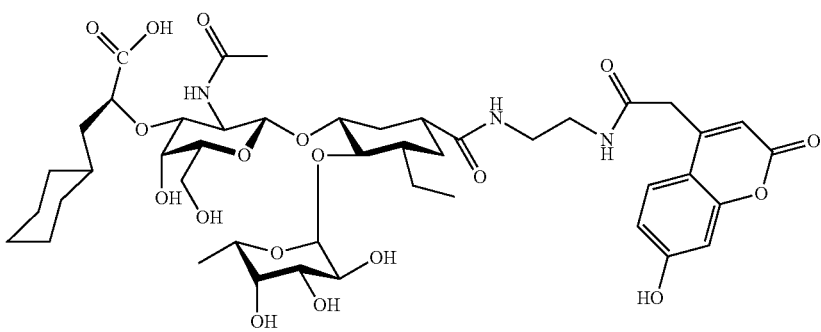

29

Commercially available compound 27C (0.021 g) was reacted with compound 23 (0.035 g) exactly in the same way as described for compound 28 and purified by HPLC (C18) to give compound 29 (0.020 g).

Example 2

E-Selectin Activity—Binding Assay

The inhibition assay to screen for and characterize glycomimetic antagonists of E-selectin is a competitive binding assay, which allows the determination of $IC_{50}$ values. E-selectin/Ig chimera was immobilized in 96 well microtiter plates by incubation at 37° C. for 2 hours. To reduce nonspecific binding, bovine serum albumin was added to each well and incubated at room temperature for 2 hours. The plate was washed and serial dilutions of the test compounds were added to the wells in the presence of conjugates of biotinylated, $sLe^a$ polyacrylamide with streptavidin/horseradish peroxidase and incubated for 2 hours at room temperature.

To determine the amount of $sLe^a$ bound to immobilized E-selectin after washing, the peroxidase substrate, 3,3',5,5' tetramethylbenzidine (TMB) was added. After 3 minutes, the enzyme reaction was stopped by the addition of $H_3PO_4$, and the absorbance of light at a wavelength of 450 nm was determined. The concentration of test compound required to inhibit binding by 50% was determined and reported as the $IC_{50}$ value for each glycomimetic E-selectin antagonist as shown in the table below. $IC_{50}$ values for exemplary compounds disclosed herein are provided in the following table.

E-Selectin Antagonist Activity of Glycomimetic Compounds

| Compound | $IC_{50}(\mu M)$ |
|---|---|
| 22 | <4.0 |
| 27 | <4.0 |
| 29 | <4.0 |
| 25 | <4.0 |
| 28 | <4.0 |
| 77* | 4.33 |

*See Example 6

In addition to reporting the absolute $IC_{50}$ value as measured above, relative $IC_{50}$ values ($rIC_{50}$) are determined by a ratio of the $IC_{50}$ measured for the test compound to that of an internal control (reference) stated for each assay.

Substitution of the methyl group at the $R^3$ position of compound 22 with a trimethylfluoro (—$CF_3$) group did not significantly alter the E-selectin antagonist activity of compound 22; however, the substitution did increase the hydrophobicity of the molecule, thereby improving the bioavailability of the glycomimetic compound.

Example 4

Mobilization of Hematopoietic Cells by an E-Selectin Antagonist

Figure 4:
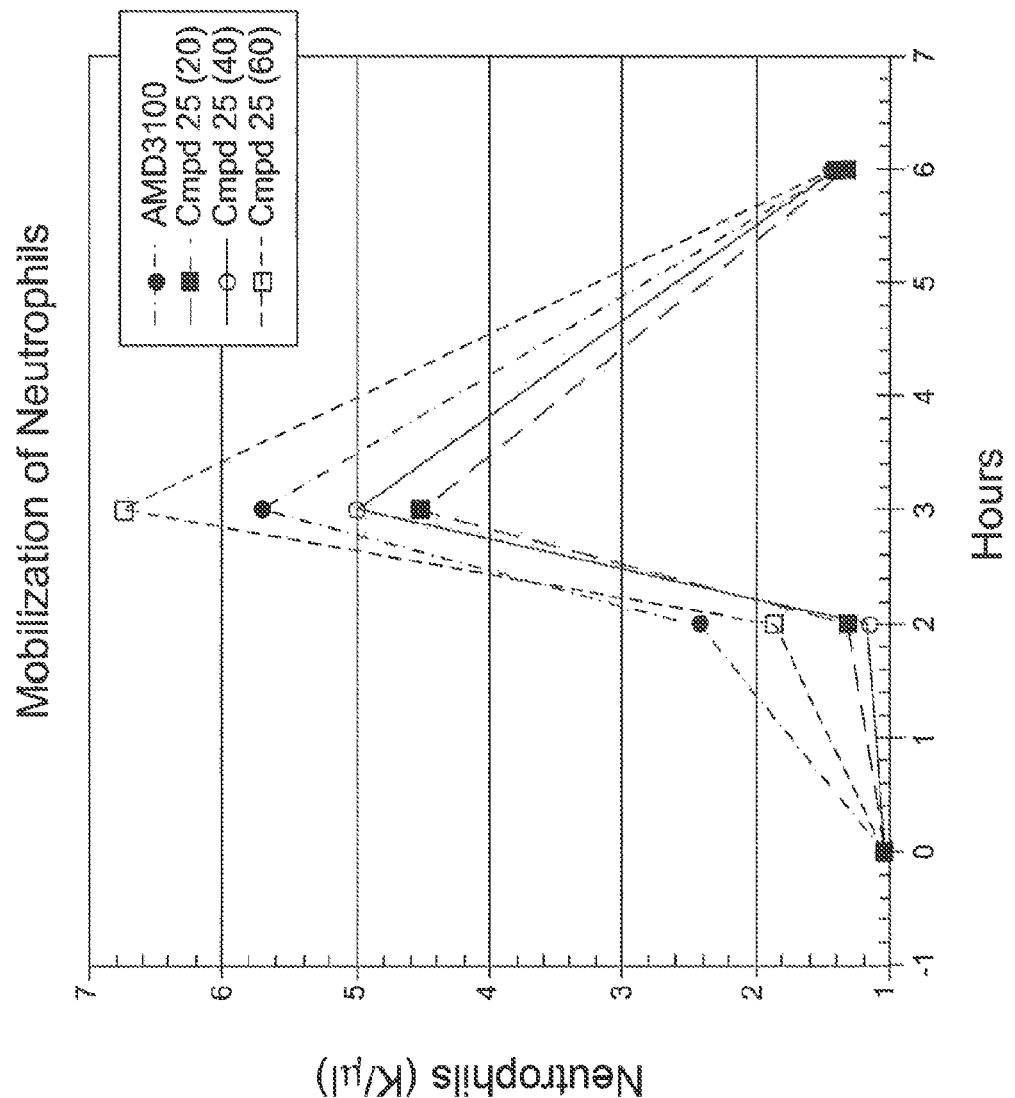
FIG. 4 illustrates mobilization of neutrophils by an exemplary E-selectin antagonist, Compound 25. Groups of animals received Compound 25 at doses of 20 mg/kg (Cmpd 25 (20)), 40 mg/kg (Cmpd 25 (40)), or 60 mg/kg (Cmpd 25 (40)). Another group of animals received 3 mg/kg of plerixafor (AMD-3100). Neutrophils were enumerated (K/μl) in blood samples taken at 2, 3, and 6 hours after dosing.
Figure 5A:
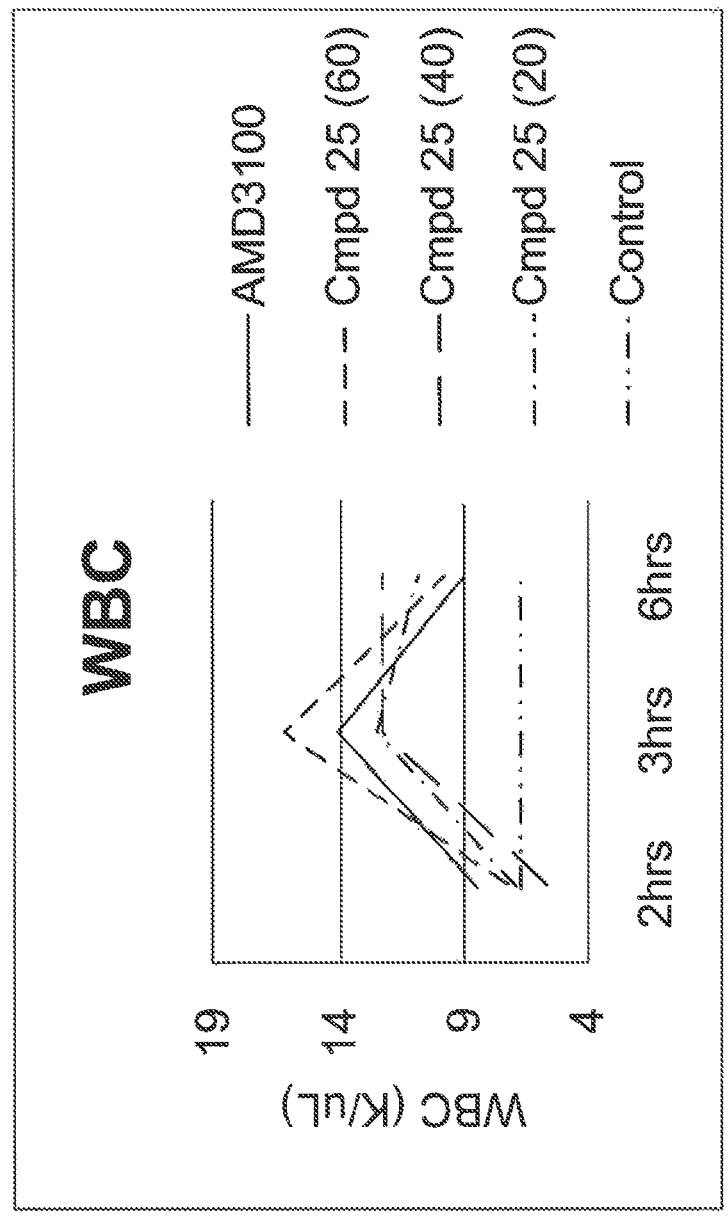
FIGS. 5A-5E shows mobilization activity of Compound 25 in CD-1 mice after a single dose of 20, 40 or 60 mg/kg of the compound injected intravenously. The mobilization activity of Compound 25 was compared to AMD3100 dosed at 3 mg/kg and to untreated controls. Blood was collected from the animals at 2, 3, and 6 hours post dosing and analyzed for levels of total white blood cells (WBC) (Figure SA), neutrophils (FIG. 5B), eosinophils (FIG. 5C), lymphocytes (FIG. 5D), monocytes (FIG. 5E).
Figure 5B:
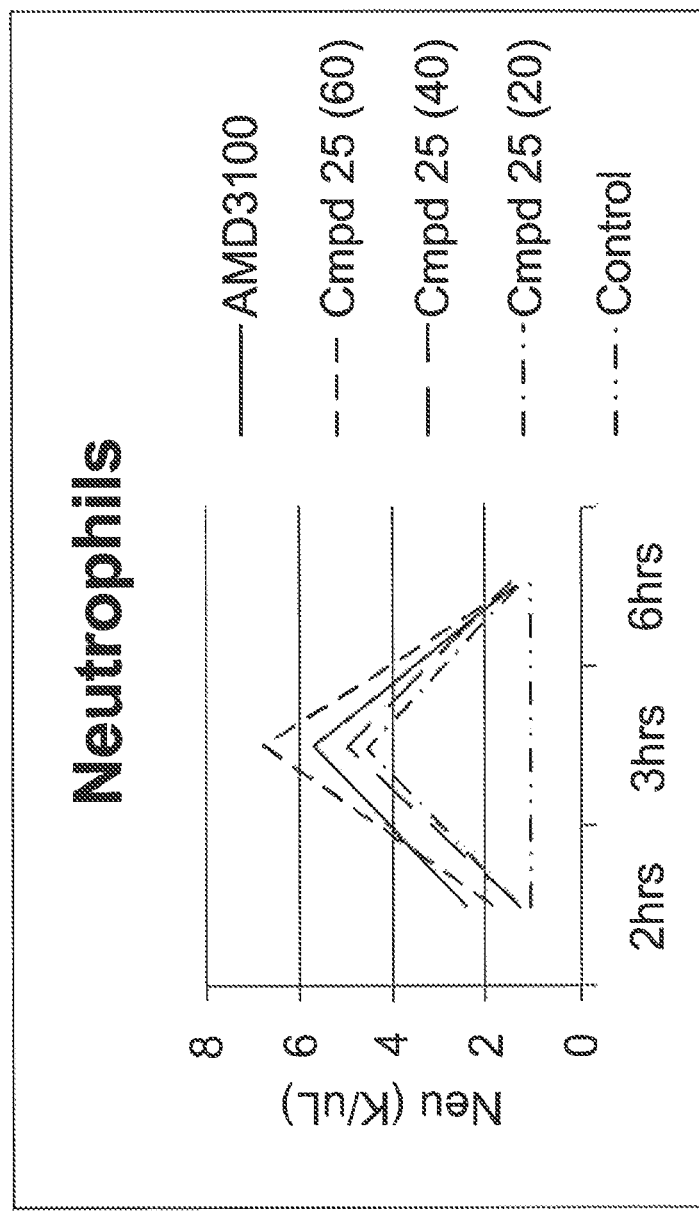
Figure 5C:
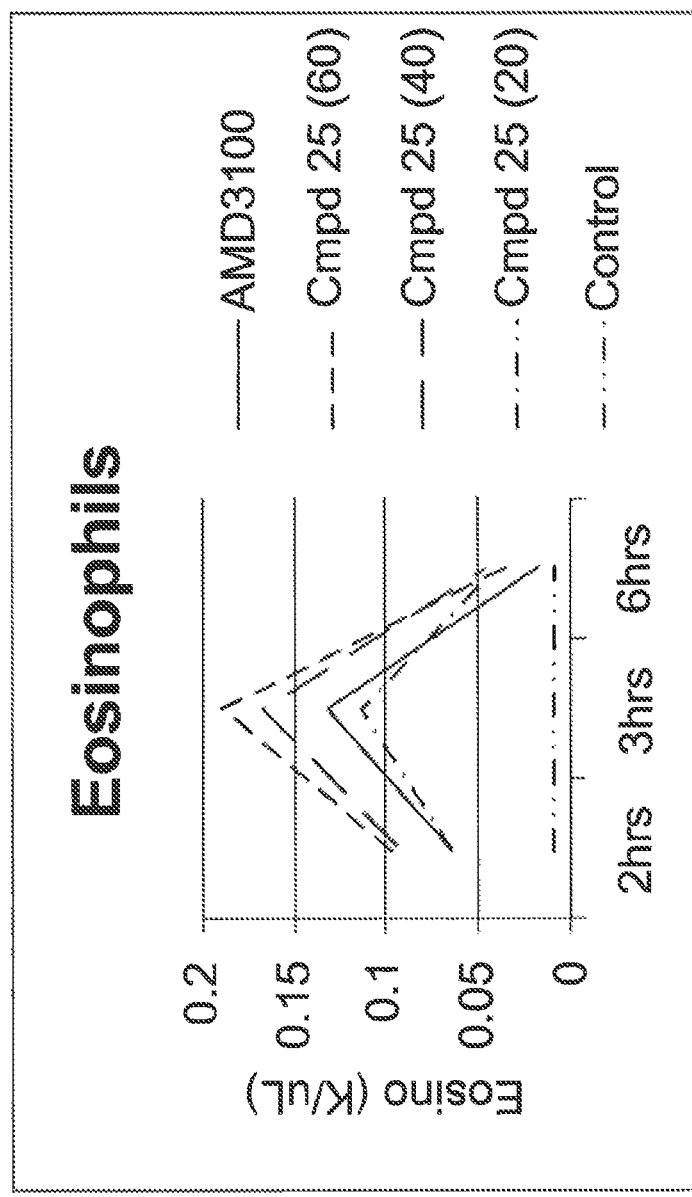
Figure 5D:
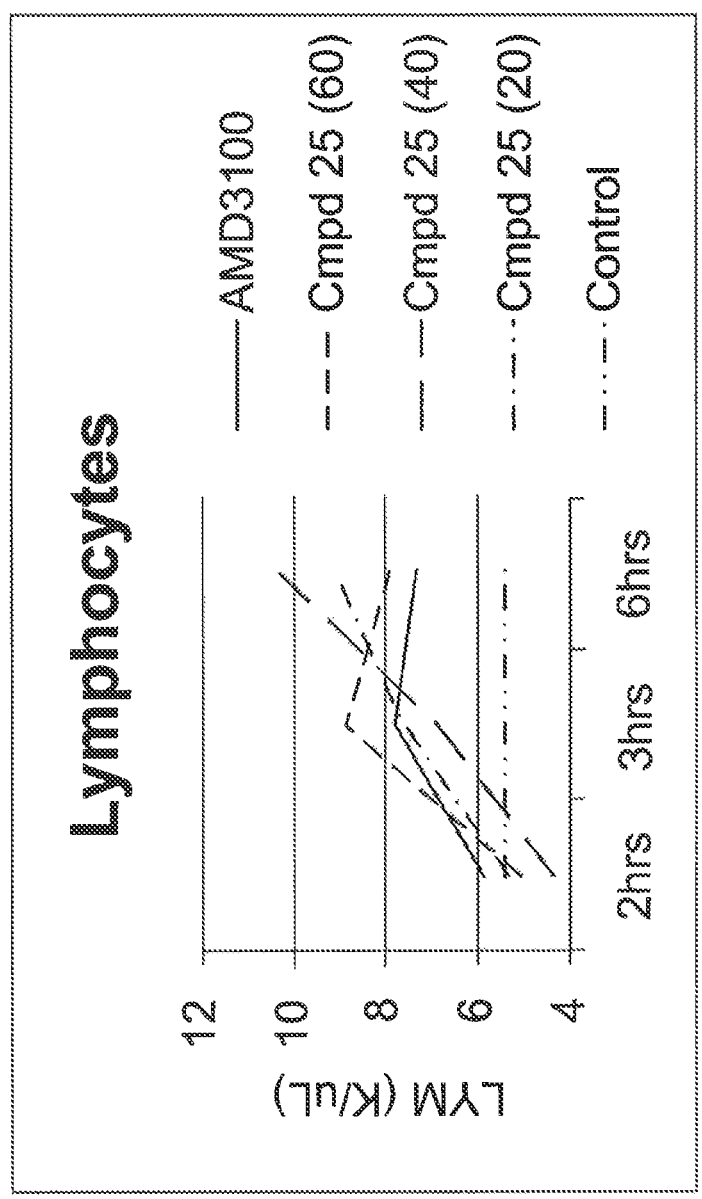
Figure 5E:
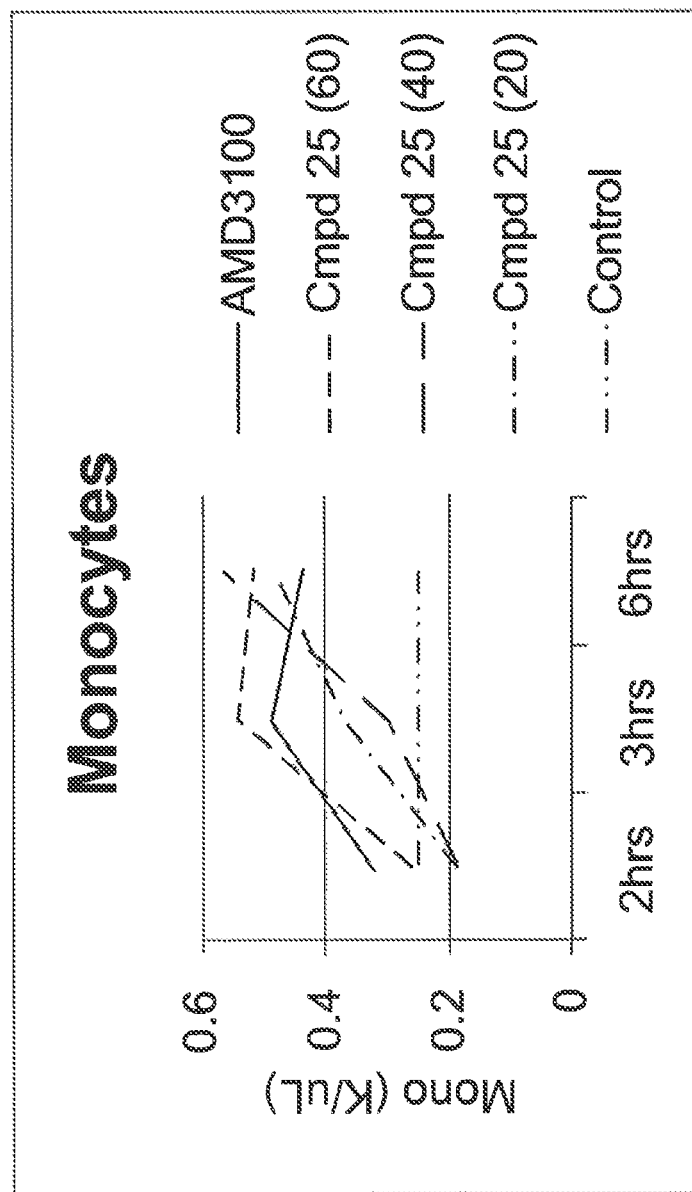

This example describes hematopoietic stem cell mobilization by an exemplary E-selectin antagonist. Groups of mice (16 mice per group) received a single dose of 20, 40, or 60 mg/kg of Compound 25 or 3 mg/kg of plerixafor (also called AMD-3100), which is a CXCR4 antagonist. These compounds were administered once intravenously. A control group of 8 animals received vehicle only. Blood samples were taken at 2, 3, and 6 hours after dosing and analyzed for complete blood count (CBC). Neutrophils were enumerated (K/µl) (i.e., 1000's per microliter) in each sample at each time point. The data are presented in FIG. 4. Administration of Compound 25 resulted in an increased number of the neutrophils in the blood (i.e., mobilization). Mobilization of neutrophils observed in animals receiving Compound 25 exhibited similar kinetics and level of increase as observed in animals receiving AMD-3100.

Example 5

Mobilization of Hematopoietic Cells by an E-Selectin Antagonist

In another experiment, the capability of an adhesion antagonist such as Compound 25 to release normal blood cells from immune compartments such as the spleen, bone marrow, and liver was examined. The mobilization activity of Compound 25 was monitored by examining the level of additional hematologic cell subtypes in circulation shortly after dosing.

Mobilization activity of Compound 25 was examined in a cohort of CD-1 mice after a single dose of 20, 40 or 60 mg/kg injected intravenously. The mobilization activity of Compound 25 was compared to AMD3100 dosed at 3 mg/kg and to untreated controls. Blood was collected from the animals at 2, 3, and 6 hours post dosing and analyzed for levels of blood cells (WBC, lymphocytes, monocytes, eosinophils, and neutrophils) by standard CBC differential analyses methods.

All dose levels of Compound 25 increased the level of total WBC, lymphocytes, monocytes, eosinophils, and neutrophils in circulation with the peak mobilization for most cell types occurring at 3 hours. The level and timing of WBC mobilization by AMD3100 was generally equivalent to that elicited by Compound 25 (FIG. 5).

Example 6

Potency of E-Selectin Antagonists

Compound 25 was evaluated for its ability to inhibit binding of an internal control E-selectin glycomimetic, Compound 77 to immobilized E-selectin in an ELISA-based assay. This inhibition assay is a competitive binding assay, which allows the determination of $IC_{50}$ values (see also Example 2). Briefly, E-selectin/Ig chimera was immobilized by incubation at 37° C. in 96-well microtiter plates. To reduce nonspecific binding, bovine serum albumin was added to each well and incubated at room temperature for 2 hours. The plates were washed, and serial dilutions of the test compounds were added to the wells in the presence of reagents capable of detecting the bound immuno-complexes (conjugates of biotinylated, SLea polyacrylamide with streptavidin/horseradish peroxidase). To determine the amount of SLea reagent bound to immobilized E-selectin after washing, the peroxidase substrate, 3,3',5,5' tetramethylbenzidin (TMB) was added. After 10 minutes, the enzyme reaction was stopped by the addition of $H_3PO_4$, and the absorbance of light at a wavelength of 450 nm was determined. The concentration of test compound required to inhibit binding by 50% was determined and reported as the $IC_{50}$ value for each glycomimetic E-selectin antagonist. In addition to reporting the absolute $IC_{50}$ value as measured above, relative $IC_{50}$ values were determined by a ratio of the $IC_{50}$ measured for the test compound to that of an internal control (reference) stated for each assay. Compound 25 was measured against the internal control, Compound 77.

Compound 25 with an average $IC_{50}$ of 2.4 µM showed competitive inhibition of E-selectin at concentrations substantially lower than the reference compound, Compound 77, which had an average $IC_{50}$ of 4.33 µM. Compound 25 selectively and potently inhibits the binding of E-selectin.

The various embodiments described above can be combined to provide further embodiments. All U.S. patents, U.S. patent application publications, U.S. patent applications, non-U.S. patents, non-U.S. patent applications, and non-patent publications referred to in this specification and/or listed in the Application Data Sheet are incorporated herein by reference, in their entirety. Aspects of the embodiments can be modified, if necessary, to employ concepts of the various patents, applications, and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

I claim the following:

1. A method for mobilizing cells from the bone marrow in a subject comprising administering to the subject a pharmaceutical composition comprising a pharmaceutically acceptable excipient and a compound of formula (I):

or a pharmaceutically acceptable salt, isomer, tautomer, hydrate or solvate thereof, wherein:
- $R^1$ is $C_1$-$C_8$ alkyl, $C_2$-$C_8$ alkenyl, $C_2$-$C_8$ alkynyl, $C_1$-$C_8$ haloalkyl, $C_2$-$C_8$ haloalkenyl or $C_2$-$C_8$ haloalkynyl;
- $R^2$ is a linker-non-glycomimetic moiety, wherein the non-glycomimetic moiety comprises polyethylene glycol;
- $R^3$ is $C_1$-$C_8$ alkyl, $C_2$-$C_8$ alkenyl, $C_2$-$C_8$ alkynyl, $C_1$-$C_8$ haloalkyl, $C_2$-$C_8$ haloalkenyl, $C_2$-$C_8$ haloalkynyl or cyclopropyl;
- $R^4$ is —OH or —$NZ^1Z^2$, wherein $Z^1$ and $Z^2$ are each independently H, $C_1$-$C_8$ alkyl, $C_2$-$C_8$ alkenyl, $C_2$-$C_8$ alkynyl, $C_1$-$C_8$ haloalkyl, $C_2$-$C_8$ haloalkenyl or $C_2$-$C_8$ haloalkynyl or wherein $Z^1$ and $Z^2$ join to form a ring;
- $R^5$ is $C_3$-$C_8$ cycloalkyl;
- $R^6$ is —OH, $C_1$-$C_8$ alkyl, $C_2$-$C_8$ alkenyl, $C_2$-$C_8$ alkynyl, $C_1$-$C_8$ haloalkyl, $C_2$-$C_8$ haloalkenyl or $C_2$-$C_8$ haloalkynyl;
- $R^7$ is —$CH_2OH$, $C_1$-$C_8$ alkyl, $C_2$-$C_8$ alkenyl, $C_2$-$C_8$ alkynyl, $C_1$-$C_8$ haloalkyl, $C_2$-$C_8$ haloalkenyl or $C_2$-$C_8$ haloalkynyl; and
- $R^8$ is $C_1$-$C_8$ alkyl, $C_2$-$C_8$ alkenyl, $C_2$-$C_8$ alkynyl, $C_1$-$C_8$ haloalkyl, $C_2$-$C_8$ haloalkenyl or $C_2$-$C_8$ haloalkynyl.

2. The method of claim 1, wherein the compound has the formula:

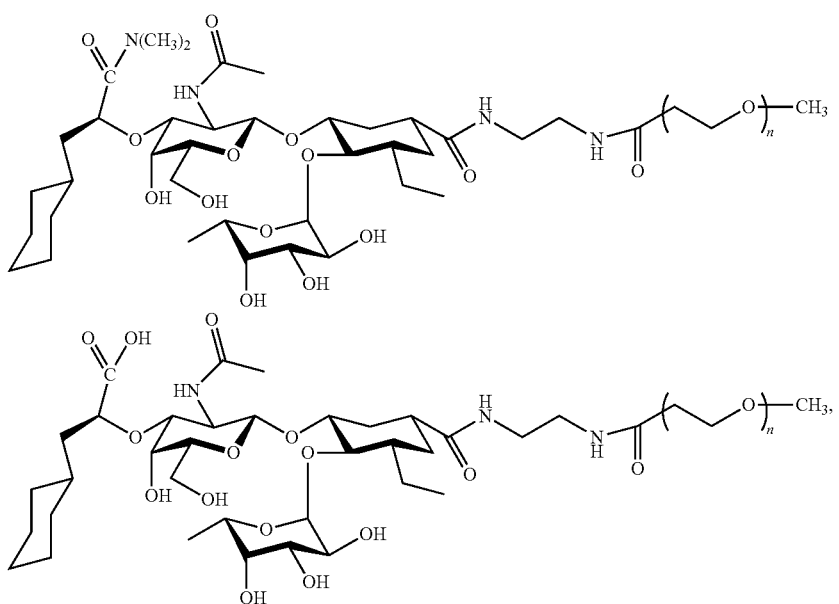

wherein n is 1 to 100.

3. The method of claim 2, wherein n is 4, 8, 12, 16, 20, 24, or 28.
4. The method of claim 1, wherein the compound has the formula:
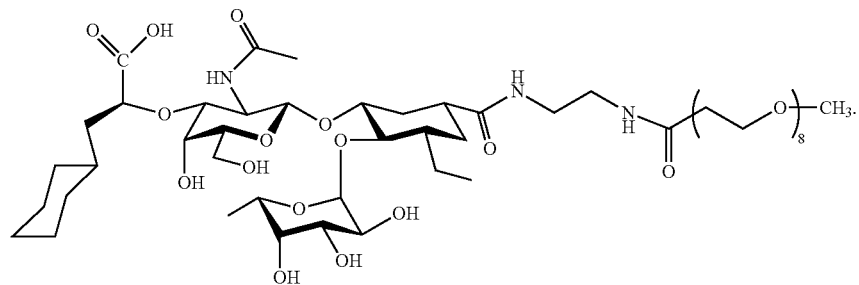
5. The method of claim 1, wherein the compound has the formula:
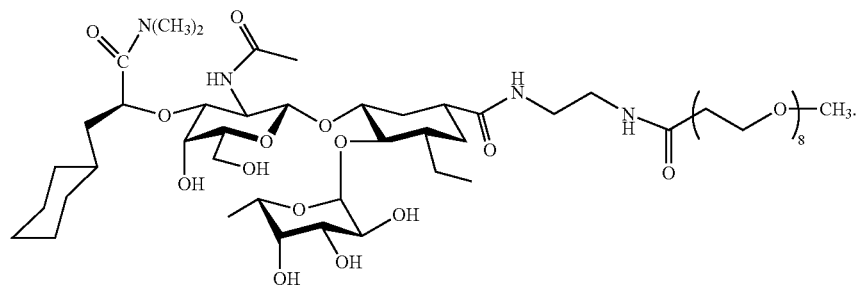
6. The method of claim 1, wherein the compound has the formula:
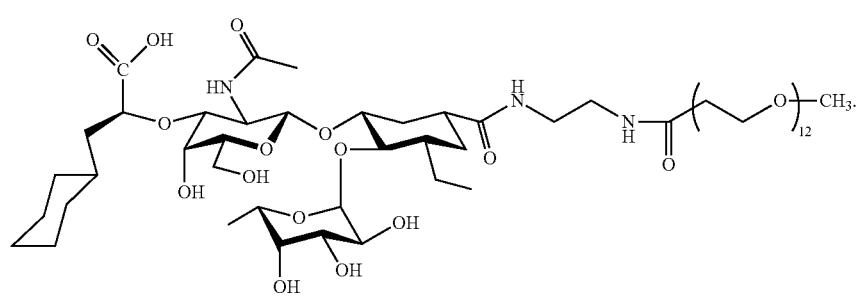
7. The method of claim 1, wherein the compound has the formula:
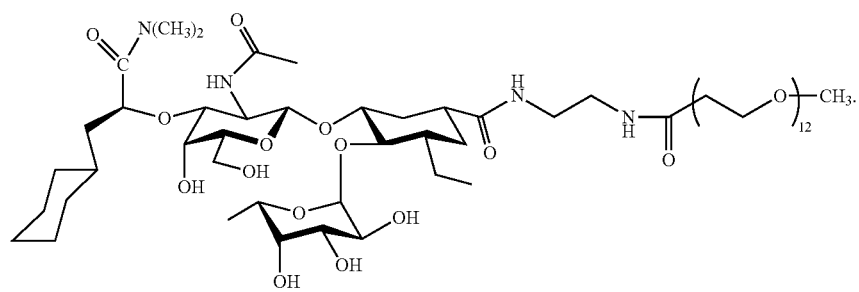

8. The method of claim 1, wherein the cells are hematopoietic cells.

9. The method of claim 8, wherein the hematopoietic cells are hematopoietic stem cells and hematopoietic progenitor cells.

10. The method of claim 8, wherein the hematopoietic cells are mature white blood cells.

11. The method of claim 1, wherein the cells are tumor cells.

12. The method of claim 11, wherein the tumor cells are hematologic tumor cells.

13. The method of claim 11, wherein the tumor cells are malignant cells.

\* \* \* \* \*